000
United States Patent
Collin et al.

(10) Patent No.: US 9,598,416 B2
(45) Date of Patent: *Mar. 21, 2017

(54) SUBSTITUTED BENZOTHIENYL-PYRROLOTRIAZINES AND USES THEREOF IN THE TREATMENT CANCER

(71) Applicants: Bayer Intellectual Property GmbH, Monheim (DE); BAYER PHARMA AKTIENGESELLSCHAFT, Berlin (DE)

(72) Inventors: Marie-Pierre Collin, Wuppertal (DE); Dirk Brohm, Mettmann (DE); Mélanie Héroult, Berlin (DE); Mario Lobell, Wuppertal (DE); Walter Hübsch, Wuppertal (DE); Klemens Lustig, Wuppertal (DE); Sylvia Grünewald, Berlin (DE); Ulf Bömer, Glienicke (DE); Verena Vöhringer, Wolfegg (DE); Niels Lindner, Wuppertal (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/365,024

(22) PCT Filed: Dec. 11, 2012

(86) PCT No.: PCT/EP2012/075127
§ 371 (c)(1),
(2) Date: Jun. 12, 2014

(87) PCT Pub. No.: WO2013/087647
PCT Pub. Date: Jun. 20, 2013

(65) Prior Publication Data
US 2015/0080371 A1    Mar. 19, 2015

(30) Foreign Application Priority Data

Dec. 15, 2011 (EP) .................................... 11193839

(51) Int. Cl.
| | | |
|---|---|---|
| *C07D 487/04* | (2006.01) | |
| *C07D 409/04* | (2006.01) | |
| *C07D 409/14* | (2006.01) | |
| *A61K 31/53* | (2006.01) | |
| *A61K 31/382* | (2006.01) | |
| *A61P 35/00* | (2006.01) | |
| *A61K 31/5377* | (2006.01) | |
| *A61K 31/541* | (2006.01) | |
| *A61K 31/551* | (2006.01) | |
| *A61K 31/553* | (2006.01) | |

(52) U.S. Cl.
CPC ............ *C07D 487/04* (2013.01); *A61K 31/53* (2013.01); *A61K 31/5377* (2013.01); *A61K 31/541* (2013.01); *A61K 31/551* (2013.01); *A61K 31/553* (2013.01); *C07D 409/04* (2013.01); *C07D 409/14* (2013.01)

(58) Field of Classification Search
CPC .. C07D 487/04; C07D 409/04; C07D 409/14; A61K 31/53; A61K 31/382
USPC .................................. 544/183, 163; 514/243
See application file for complete search history.

(56) References Cited

FOREIGN PATENT DOCUMENTS

| WO | 0071129 A1 | 11/2000 |
|---|---|---|
| WO | 0119828 A2 | 3/2001 |
| WO | 2005037836 A2 | 4/2005 |
| WO | 2005097800 A1 | 10/2005 |
| WO | 2005121147 A1 | 12/2005 |
| WO | 2007056170 A2 | 5/2007 |
| WO | 2007061737 A2 | 5/2007 |
| WO | 2007061882 A2 | 5/2007 |
| WO | 2007064883 A2 | 6/2007 |
| WO | 2007064931 A2 | 6/2007 |
| WO | 2007064932 A2 | 6/2007 |
| WO | 2007079164 A2 | 7/2007 |
| WO | 2009042543 A1 | 4/2009 |

(Continued)

OTHER PUBLICATIONS

Hynes et al., Cancer Res. Jul. 1, 2010;70(13):5199-202.*

(Continued)

*Primary Examiner* — Venkataraman Balasubramanian
(74) *Attorney, Agent, or Firm* — Nixon & Vanderhye P.C.

(57) ABSTRACT

This invention relates to novel substituted 5-(1-benzothiophen-2-yl)pyrrolo[2,1-f][1,2,4]triazin-4-amine derivatives having protein tyrosine kinase inhibitory activities, to processes for the preparation of such compounds, to pharmaceutical compositions containing such compounds, and to the use of such compounds or compositions for treating proliferative disorders, in particular cancer and tumor diseases.

7 Claims, No Drawings

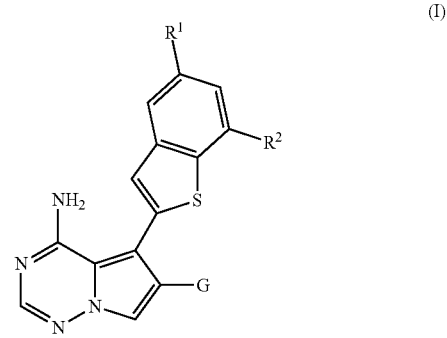

(56) References Cited

FOREIGN PATENT DOCUMENTS

| WO | 2009136966 A1 | 11/2009 |
| WO | 2010051043 A1 | 5/2010 |
| WO | 2010126960 A1 | 11/2010 |

OTHER PUBLICATIONS

Greulich et al.,Trends Mol Med. May 2011;17(5):283-92.*
Cecil Textbook of Medicine, edited by Bennet, J.C., and Plum F., 20th edition,vol. 1, 1004-101 O, 1996.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Cohen et al., Current Opinion in Chemical Biology, 3,459-465, 1999.*
Barder et al., "Catalysts for Suzuki-Miyaura Coupling Processes: Scope and Studies of the Effect of Ligand Structure," 2005, Journal of Am. Chem. Soc., 127:4685-4696.
Berge et al., "Pharmaceutical Salts," Journal of Pharm. Sciences, Jan. 1977, 66(1):1-19.
Bergers et al., "Modes of resistance to antiangiogenic therapy," Nature Reviews Cancer, Aug. 2008, 8:592-603.
Greene et al., Protective Groups in Organic Synthesis, Third Edition, "The Role of Protective Groups in Organic Synthesis," 1999, John Wiley & Sons, Inc., ISBN 0-471-22057-4 (Electronic) 1-16.
Greulich et al., "Targeting mutant fibroblast growth factor receptors in cancer," Trends in Molecular Medicine, May 2011, 17(5):283-292.
Haugsten et al., "Roles of Fibroblast Growth Factor Receptors in Carcinogenesis," American Association for Cancer Research, Molecular Cancer Research, 2010, 1439-1452.
Heinzle et al., "Targeting fibroblast-growth-factor-receptor-dependent signaling for cancer therapy," Expert Opin. Ther. Targets, 2011, 15(7):830-846.
Itoh et al., "Fibroblast growth factors: from molecular evolution to roles in development, metabolism and disease," JB Journal of Biochemistry, 2011, 149(2):121-130.
Jilek et al., "Potential Metabolites of the Neuroleptic Agent Octoclothepin; Synthesis and Pharmacology of 8-Chloro-6-Hydroxy-10-(4-Methylpiperazino)-10,11-Dihydrodibenzo[b,f]Thiepin and Some Related Compounds," Research Institute for Pharmacy and Biochemistry, 130 00 Prague 3, Collection Czechoslov Chem. Commun., 1978, 43:1747-1759.
Knapp et al., "A General Solution for Unstable Boronic Acids: Slow-Release Cross-Coupling from Air-Stable MIDA Boronates," Journal Am. Chem. Society, 2009, 131:6961-6963.
Kinzel et al., "A New Palladium Precatalyst Allows for the Fast Suzuki-Miyaura Coupling Reactions of Unstable Polyfluorophenyl and 2-Heteroaryl Boronic Acids," Journal Am. Chem. Society, 132:14073-14075.
Korc et al, "The Role of Fibroblast Growth Factors in Tumor Growth," Current Cancer Drug Targets, 2009, 9:639-651.
Kotha et al., "Recent applications of the Suzuki-Miyaura cross-coupling reaction in organic synthesis," Tetrahedron, 2002, 58:9633-9695.
Balkrishna et al, "Oxidation of α, β-Unstaturated Aldehydes," Tetrahedron, 1981, 37:2091-1096.
Plé et al., "Synthesis of Substituted Benzo[b]thiophenes by Acid-Catalyzed Cyclization of Thiophenylacetals and Ketones," J. Heterocyclic Chem., 1988, 25:1271-1272.
"Polanska et al., ""Extracellular Interactome of the FGF Receptor-Ligand System: Complexities and theRelative Simplicity of the Worm,"" Development Dynamics, 2009, 238:277-293".
Raach et al., "Sodium Chlorite-Hydrogen Peroxide—A Mild and Selective Reagent for the Oxidation of Aldehydes to Carboxylic Acids," Journal Prakt Chem., 2000, 342(6):605-608.
Swinney et al., "How were new medicines discovered?," Nature Reviews Drug Discovery, Jul. 2011, 10:507-519.
Nooy et al., "On the Use of Stable Organic Nitroxyl Radicals for the Oxidation of Primary and Secondary Alcohols," Synthesis, Oct. 1996, 1153-1174.
Venturelli et al., "Optimizing Cell Permeation of an Antibiotic Resistance Inhibitor for Improved Efficacy," Journal Med. Chem., 2007, 50:5644-5654.
Wesche et al., "Fibroblast growth factors and their receptors in cancer," Biochemical Journal, 2011, 437:199-213. Supplemental Tables S1-S3 and additional references (pp. 1-13 at the end).
Zhao et al., "Oxidation of Primary Alcohols to Carboxylic Acids with Sodium Chlorite Catalyzed by Tempo and Bleach: 4-Methoxyphenylacetic Acid (Benzeneacetic acid, 4-methoxy-," Organic Syntheses, 2005 81:195-204.
Worldwide Health Organization, Fact Sheet No. 297, Feb. 2011 updated Feb. 2014.

* cited by examiner

SUBSTITUTED BENZOTHIENYL-PYRROLOTRIAZINES AND USES THEREOF IN THE TREATMENT CANCER

This invention relates to novel substituted 5-(1-benzothiophen-2-yl)pyrrolo[2,1-f][1,2,4]triazin-4-amine derivatives having protein tyrosine kinase inhibitory activities, to processes for the preparation of such compounds, to pharmaceutical compositions containing such compounds, and to the use of such compounds or compositions for treating proliferative disorders, in particular cancer and tumor diseases.

Cancer is a leading cause of death worldwide and accounted for 7.6 million deaths (around 13% of all deaths) in 2008. Deaths from cancer are projected to continue to rise worldwide to over 11 million in 2030 (WHO source, Fact Sheet No. 297, February 2011).

There are many ways how cancers can arise which is one of the reasons why their therapy is difficult. One way that transformation of cells can occur is following a genetic alteration. The completion of the human genome project showed genomic instability and heterogeneity of human cancer genes. Recent strategies to identify these genetic alterations sped up the process of cancer-gene discovery. Gene abnormality can, for instance, lead to the overexpression of proteins, and hence to a nonphysiological activation of these proteins. One family of proteins from which a number of onco-proteins derive are tyrosine kinases and in particular receptor tyrosine kinases (RTKs). In the past two decades, numerous avenues of research have demonstrated the importance of RTK-mediated signalling in adverse cell growth leading to cancer. In recent years, promising results have been achieved in the clinic with selective small-molecule inhibitors of tyrosine kinases as a new class of anti-tumorigenic agents [Swinney and Anthony, *Nature Rev. Drug Disc.* 10 (7), 507-519 (2011)].

Fibroblast growth factors (FGFs) and their receptors (FGFRs) form part of a unique and diverse signalling system which plays a key role in a variety of biological processes which encompass various aspects of embryonic development and adult pathophysiology [Itoh and Ornitz, *J. Biochem.* 149 (2), 121-130 (2011)]. In a spatio-temporal manner, FGFs stimulate through FGFR binding a wide range of cellular functions including migration, proliferation, differentiation, and survival.

The FGF family comprises 18 secreted polypeptidic growth factors that bind to four highly conserved receptor tyrosine kinases (FGFR-1 to -4) expressed at the cell surface. In addition, FGFR-5 can bind to FGFs but does not have a kinase domain, and therefore is devoid of intracellular signalling. The specificity of the ligand/receptor interaction is enhanced by a number of transcriptional and translational processes which give rise to multiple isoforms by alternative transcriptional initiation, alternative splicing, and C-terminal truncations. Various heparan sulfate proteoglycans (e.g. syndecans) can be part of the FGF/FGFR complex and strongly influence the ability of FGFs to induce signalling responses [Polanska et al., *Developmental Dynamics* 238 (2), 277-293 (2009)]. FGFRs are cell surface receptors consisting of three extracellular immunoglobulin-like domains, a single-pass transmembrane domain, and an intracellular dimerized tyrosine kinase domain. Binding of FGF bring the intracellular kinases into close proximity, enabling them to transphosphorylate each other. Seven phosphorylation sites have been identified (e.g., in FGFR-1 Tyr463, Tyr583, Tyr585, Tyr653, Tyr654, Tyr730, and Tyr766).

Some of these phosphotyrosine groups act as docking sites for downstream signalling molecules which themselves may also be directly phosphorylated by FGFR, leading to the activation of multiple signal transduction pathways. Thus, the MAPK signalling cascade is implicated in cell growth and differentiation, the PI3K/Akt signalling cascade is involved in cell survival and cell fate determination, while the PI3K and PKC signalling cascades have a function in the control of cell polarity. Several feedback inhibitors of FGF signalling have now been identified and include members of the Spry (Sprouty) and Sef (similar expression to FGF) families. Additionally, in certain conditions, FGFR is released from pre-Golgi membranes into the cytosol. The receptor and its ligand, FGF-2, are co-transported into the nucleus by a mechanism that involves importin, and are engaged in the CREB-binding protein (CBP) complex, a common and essential transcriptional coactivator that acts as a gene activation gating factor. Multiple correlations between the immunohistochemical expression of FGF-2, FGFR-1 and FGFR-2 and their cytoplasmic and nuclear tumor cell localizations have been observed. For instance, in lung adenocarcinomas this association is also found at the nuclear level, emphasizing an active role of the complex at the nucleus [Korc and Friesel, *Curr. Cancer Drugs Targets* 5, 639-651 (2009)].

FGFs are widely expressed in both developing and adult tissues and play important roles in a variety of normal and pathological processes, including tissue development, tissue regeneration, angiogenesis, neoplastic transformation, cell migration, cellular differentiation, and cell survival. Additionally, FGFs as pro-angiogenic factors have also been implicated in the emerging phenomenon of resistance to vascular endothelial growth factor receptor-2 (VEGFR-2) inhibition [Bergers and Hanahan, *Nat. Rev. Cancer* 8, 592-603 (2008)].

Recent oncogenomic profiles of signalling networks demonstrated an important role for aberrant FGF signalling in the emergence of some common human cancers [Wesche et al., *Biochem. J.* 437 (2), 199-213 (2011)]. Ligand-independent FGFR constitutive signalling has been described in many human cancers, such as brain cancer, head and neck cancer, gastric cancer and ovarian cancer. FGFR-mutated forms as well as FGFR-intragenic translocations have been identified in malignancies such as myeloproliferative diseases. Interestingly, the same mutations discovered to be the cause of many developmental disorders are also found in tumor cells (e.g., the mutations found in achondroplasia and thanatophoric dysplasia, which cause dimerization and thus constitutive activation of FGFR-3, are also frequently found in bladder cancer). A mutation that promotes dimerization is just one mechanism that can increase ligand-independent signalling from FGFRs. Other mutations located inside or outside of the kinase domain of FGFRs can change the conformation of the domain giving rise to permanently active kinases.

Amplification of the chromosomal region 8p11-12, the genomic location of FGFR-1, is a common focal amplification in breast cancer and occurs in approximately 10% of breast cancers, predominantly in oestrogen receptor-positive cancers. FGFR-1 amplifications have also been reported in non-small cell lung squamous carcinoma and are found at a low incidence in ovarian cancer, bladder cancer and rhabdomyosarcoma. Similarly, approximately 10% of gastric cancers show FGFR-2 amplification, which is associated with poor prognosis, diffuse-type cancers. Moreover, multiple single nucleotide polymorphisms (SNPs) located in FGFR-1 to -4 were found to correlate with an increased risk of developing selective cancers, or were reported to be associated with poor prognosis (e.g., FGFR-4 G388R allele in breast cancer, colon cancer and lung adenocarcinoma). The direct role of these SNPs to promote cancer is still controversial.

In summary, a great number of in vitro and in vivo studies have been performed that validate FGFR-1 to -4 as important cancer targets, and comprehensive reviews have summarized these findings [see, for example, Heinzle et al., *Expert Opin. Ther. Targets* 15 (7), 829-846 (2011); Wesche et al., *Biochem. J.* 437 (2), 199-213 (2011); Greulich and Pollock, *Trends in Molecular Medicine* 17 (5), 283-292 (2011); Haugsten et al., *Mol. Cancer Res.* 8 (11), 1439-1452 (2010)]. Several strategies have been followed to attenuate aberrant FGFR-1 to -4 signalling in human tumors including blocking antibodies and small-molecule inhibitors, amongst others. A number of selective small-molecule FGFR inhibitors are currently in clinical development, such as AZD-4547 (AstraZeneca) and BJG-398 (Novartis).

Notwithstanding the significant advancements that have generally been achieved in cancer therapy in recent years, there is a continuing need to identify new anti-cancer compounds with improved properties, such as higher potency, greater selectivity, reduced toxicity and/or better tolerability. Therefore, the technical problem to be solved according to the present invention may be seen in providing alternative compounds having inhibitory activity on the FGFR kinases, thus offering new therapeutic options for the treatment of FGFR-mediated diseases, in particular cancer and other proliferative disorders.

Fused hetero-5,6-bicyclic kinase inhibitors bearing a 9- or a 10-membered bicyclic heteroaryl substituent have been disclosed in WO 2007/061737-A2 and WO 2005/097800-A1, respectively. These compounds were stated to be useful for the treatment of cancer and other diseases owing to their inhibitory action on the mTOR (mammalian target of Rapamycin) and/or IGF-1R (type 1 insulin-like growth factor receptor) kinases. Further hetero-5,6-bicyclic template structures associated with the inhibition of kinases have been described in, inter alia, WO 01/19828-A2, WO 2007/079164-A2 and WO 2010/051043-A1.

4-Aminopyrrolo[2,1-f][1,2,4]triazine derivatives with differing inhibition profiles against a number of protein kinases have been disclosed in, inter alia, WO 00/71129-A1, WO 2007/056170-A2, WO 2007/061882-A2, WO 2007/064932-A2, WO 2009/136966-A1, and WO 2010/126960-A1.

In WO 2005/121147-A1, WO 2007/064883-A2 and WO 2007/064931-A2, 4-aminopyrrolo[2,1-f]-[1,2,4]triazine derivatives containing a substituted diarylurea group in 5-position were described as having FGFR-1 inhibiting activity. However, other receptor tyrosine kinases, notably the VEGFR, PDGFR and Tie-2 kinases, are also significantly inhibited by this particular class of compounds. As it was hypothesized that such multi-kinase activity might lead to an augmentation of potential side effects during treatment, it was the aim of the present invention to identify new agents having an improved selectivity for the FGFR kinases, thus providing new options for a more tolerable cancer therapy.

Surprisingly, it has now been found that 4-aminopyrrolo[2,1-f][1,2,4]triazine derivatives bearing a specifically substituted benzothiophen-2-yl residue in 5-position exhibit potent and selective inhibition of FGFR kinases, notably of the FGFR-1 and FGFR-3 kinases, which renders these compounds particularly useful for the treatment of proliferative disorders, such as cancer and tumor diseases.

Thus, in one aspect, the present invention relates to 6-substituted 5-(1-benzothiophen-2-yl)pyrrolo[2,1-f][1,2,4]triazin-4-amine derivatives of the general formula (I)

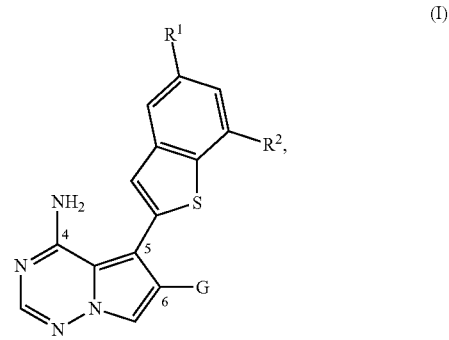

wherein
$R^1$ is hydrogen, chloro, methyl or methoxy,
$R^2$ is hydrogen or methoxy,
  with the proviso that at least one of $R^1$ and $R^2$ is other than hydrogen,
and
G represents the group —$CH_2$—$OR^3$, —C(=O)—$OR^3$, —$CH_2$—$NR^4R^5$ or —C(=O)—$NR^4R^6$, wherein
  $R^3$ is hydrogen or ($C_1$-$C_4$)-alkyl optionally substituted with cyano, hydroxy, ($C_1$-$C_4$)alkoxy, hydroxycarbonyl, ($C_1$-$C_4$)-alkoxycarbonyl, amino, mono-($C_1$-$C_4$)-alkylamino, di-($C_1$-$C_4$)-alkylamino, pyrrolidino, piperidino, morpholino, aminocarbonyl, mono-($C_1$-$C_4$)-alkylaminocarbonyl, di-($C_1$-$C_4$)-alkylaminocarbonyl or up to three fluoro atoms,
  $R^4$ is hydrogen or ($C_1$-$C_4$)-alkyl,
  $R^5$ is hydrogen, ($C_1$-$C_4$)-alkyl, ($C_1$-$C_4$)-alkylcarbonyl, ($C_3$-$C_6$)-cycloalkyl or 4- to 6-membered heterocycloalkyl, wherein
    (i) said ($C_1$-$C_4$)-alkyl is optionally substituted with cyano, hydroxy, ($C_1$-$C_4$)alkoxy, ($C_1$-$C_4$)-alkoxycarbonyl, aminocarbonyl, mono-($C_1$-$C_4$)-alkylaminocarbonyl, di-($C_1$-$C_4$)-alkylaminocarbonyl, ($C_1$-$C_4$)-alkylcarbonylamino or up to three fluoro atoms,
    and
    (ii) said ($C_3$-$C_6$)-cycloalkyl is optionally substituted with one or two substituents independently selected from the group consisting of ($C_1$-$C_4$)-alkyl, hydroxy, amino and ($C_1$-$C_4$)-alkylcarbonylamino,
    and
    (iii) said 4- to 6-membered heterocycloalkyl is optionally substituted with one or two substituents independently selected from the group consisting of ($C_1$-$C_4$)alkyl, hydroxy, oxo, amino and ($C_1$-$C_4$)-alkylcarbonylamino,
  $R^6$ is hydrogen, ($C_1$-$C_4$)-alkyl, ($C_3$-$C_6$)-cycloalkyl or 4- to 6-membered heterocycloalkyl, wherein
    (i) said ($C_1$-$C_4$)-alkyl is optionally substituted with hydroxy, ($C_1$-$C_4$)-alkoxy, ($C_1$-$C_4$)-alkoxycarbonyl, amino, aminocarbonyl, mono-($C_1$-$C_4$)-alkylaminocarbonyl, di-($C_1$-$C_4$)-alkylaminocarbonyl or ($C_1$-$C_4$)-alkylcarbonylamino,
    and
    (ii) said ($C_3$-$C_6$)-cycloalkyl is optionally substituted with one or two substituents independently selected from the group consisting of $(C_1-C_4)$-alkyl, hydroxy, amino and $(C_1-C_4)$-alkylcarbonylamino, and (iii) said 4- to 6-membered heterocycloalkyl is optionally substituted with one or two substituents independently selected from the group consisting of $(C_1-C_4)$alkyl, hydroxy, oxo, amino and $(C_1-C_4)$-alkylcarbonylamino, or $R^4$ and $R^5$, or $R^4$ and $R^6$, respectively, are joined and, taken together with the nitrogen atom to which they are attached, form a monocyclic, saturated 4- to 7-membered heterocycloalkyl ring which may contain a second ring heteroatom selected from $N(R^7)$, O, S and $S(O)_2$, and which may be substituted on ring carbon atoms with up to three substituents independently selected from the group consisting of fluoro, $(C_1-C_4)$ alkyl, oxo, hydroxy, $(C_1-C_4)$-alkoxy, amino, mono-$(C_1-C_4)$-alkylamino, di-$(C_1-C_4)$alkylamino and aminocarbonyl, and wherein $R^7$ is hydrogen, $(C_1-C_4)$-alkyl, cyclopropyl, cyclobutyl, formyl, $(C_1-C_4)$-alkyl-carbonyl or $(C_1-C_4)$-alkoxycarbonyl.

The compounds according to this invention can also be present in the form of their salts, solvates and/or solvates of the salts.

Compounds according to the invention are the compounds of the formula (I) and their salts, solvates and solvates of the salts, the compounds included in the formula (I) of the formulae (I-A) to (I-G2) mentioned in the following and their salts, solvates and solvates of the salts, and the compounds included in the formula (I) and mentioned in the following as process products and/or embodiment examples and their salts, solvates and solvates of the salts, where the compounds included in the formula (I) and mentioned in the following are not already salts, solvates and solvates of the salts.

Salts for the purposes of the present invention are preferably pharmaceutically acceptable salts of the compounds according to the invention (for example, see S. M. Berge et al., "Pharmaceutical Salts", *J. Pharm. Sci.* 1977, 66, 1-19). Salts which are not themselves suitable for pharmaceutical uses but can be used, for example, for isolation or purification of the compounds according to the invention are also included.

Pharmaceutically acceptable salts include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, formic acid, acetic acid, trifluoroacetic acid, propionic acid, lactic acid, tartaric acid, malic acid, citric acid, fumaric acid, maleic acid, and benzoic acid.

Pharmaceutically acceptable salts also include salts of customary bases, such as for example and preferably alkali metal salts (for example sodium and potassium salts), alkaline earth metal salts (for example calcium and magnesium salts), and ammonium salts derived from ammonia or organic amines, such as illustratively and preferably ethylamine, diethylamine, triethylamine, N,N-diisopropylethylamine, monoethanolamine, diethanolamine, triethanolamine, dimethylaminoethanol, diethylaminoethanol, procaine, dicyclohexylamine, dibenzylamine, N-methylmorpholine, N-methylpiperidine, arginine, lysine, and 1,2-ethylenediamine.

Solvates in the context of the invention are designated as those forms of the compounds according to the invention which form a complex in the solid or liquid state by stoichiometric coordination with solvent molecules. Hydrates are a specific form of solvates, in which the coordination takes place with water. Hydrates are preferred solvates in the context of the present invention.

The compounds of this invention may, either by nature of asymmetric centers or by restricted rotation, be present in the form of isomers (enantiomers, diastereomers). Any isomer may be present in which the asymmetric center is in the (R)-, (S)-, or (R,S)-configuration.

It will also be appreciated that when two or more asymmetric centers are present in the compounds of the invention, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the invention.

Geometric isomers by nature of substituents about a double bond or a ring may be present in cis (=Z-) or trans (=E-) form, and both isomeric forms are encompassed within the scope of this invention.

All isomers, whether separated, pure, partially pure, or in racemic mixture, of the compounds of this invention are encompassed within the scope of this invention. The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by resolution.

In addition, all possible tautomeric forms of the compounds described above are included according to the present invention.

The present invention also encompasses all suitable isotopic variants of the compounds according to the invention. An isotopic variant of a compound according to the invention is understood to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, fluorine, chlorine, bromine and iodine, such as $^2H$ (deuterium), $^3H$ (tritium), $^{13}C$, $^{14}C$, $^{15}N$, $^{17}O$, $^{18}O$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the active compound distribution in the body. Due to comparatively easy preparability and detectability, especially compounds labelled with $^3H$ or $^{14}C$ isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required. Such modifications of the compounds according to the invention may therefore in some cases also constitute a preferred embodiment of the present invention. Isotopic variants of the compounds according to the invention can be prepared by processes known to those skilled in the art, for example by the methods described below and the methods described in the working examples, by using corresponding isotopic modifications of the particular reagents and/or starting compounds therein.

In the context of the present invention, the substituents and residues have the following meaning, unless specified otherwise:

($C_1$-$C_4$)-Alkyl in the context of the invention represents a straight-chain or branched alkyl radical having 1 to 4 carbon atoms. There may be mentioned by way of example and preferably: methyl, ethyl, n-propyl, isopropyl, n-butyl, iso-butyl, sec-butyl, and tert-butyl.

($C_1$-$C_4$)-Alkoxy in the context of the invention represents a straight-chain or branched alkoxy radical having 1 to 4 carbon atoms. There may be mentioned by way of example and preferably: methoxy, ethoxy, n-propoxy, isopropoxy, n-butoxy, iso-butoxy, sec-butoxy, and tert-butoxy.

Mono-($C_1$-$C_4$)-alkylamino in the context of the invention represents an amino group with a straight-chain or branched alkyl substituent which contains 1 to 4 carbon atoms. There may be mentioned by way of example and preferably: methylamino, ethylamino, n-propylamino, isopropylamino, n-butylamino, and tert-butylamino.

Di-($C_1$-$C_4$)-alkylamino in the context of the invention represents an amino group with two identical or different straight-chain or branched alkyl substituents which each contain 1 to 4 carbon atoms. There may be mentioned by way of example and preferably: N,N-dimethylamino, N,N-diethylamino, N-ethyl-N-methylamino, N-methyl-N-n-propylamino, N-isopropyl-N-methylamino, N-isopropyl-N-n-propylamino, N,N-diisopropylamino, N-n-butyl-N-methylamino, and N-tert-butyl-N-methylamino.

($C_1$-$C_4$)-Alkylcarbonyl in the context of the invention represents a straight-chain or branched alkyl radical having 1 to 4 carbon atoms which is bonded to the rest of the molecule via a carbonyl group [—C(=O)—]. There may be mentioned by way of example and preferably: acetyl, propionyl, n-butyryl, iso-butyryl, n-pentanoyl, and pivaloyl.

($C_1$-$C_4$)-Alkoxycarbonyl in the context of the invention represents a straight-chain or branched alkoxy radical having 1 to 4 carbon atoms which is bonded to the rest of the molecule via a carbonyl group [—C(=O)—]. There may be mentioned by way of example and preferably: methoxycarbonyl, ethoxycarbonyl, n-propoxycarbonyl, isopropoxycarbonyl, n-butoxycarbonyl, and tert-butoxycarbonyl.

Mono-($C_1$-$C_4$)-alkylaminocarbonyl in the context of the invention represents an amino group which is bonded to the rest of the molecule via a carbonyl group [—C(=O)—] and which has a straight-chain or branched alkyl substituent having 1 to 4 carbon atoms. There may be mentioned by way of example and preferably: methylaminocarbonyl, ethylaminocarbonyl, n-propylaminocarbonyl, isopropylaminocarbonyl, n-butylaminocarbonyl, and tert-butylaminocarbonyl.

Di-($C_1$-$C_4$)-alkylaminocarbonyl in the context of the invention represents an amino group which is bonded to the rest of the molecule via a carbonyl group [—C(=O)—] and which has two identical or different straight-chain or branched alkyl substituents having in each case 1 to 4 carbon atoms. There may be mentioned by way of example and preferably: N,N-dimethylaminocarbonyl, N,N-diethylaminocarbonyl, N-ethyl-N-methylaminocarbonyl, N-methyl-N-n-propylaminocarbonyl, N-isopropyl-N-methylaminocarbonyl, N,N-diisopropylaminocarbonyl, N-n-butyl-N-methylaminocarbonyl, and N-tert-butyl-N-methylaminocarbonyl.

($C_1$-$C_4$)-Alkylcarbonylamino in the context of the invention represents an amino group with a straight-chain or branched alkylcarbonyl substituent which contains 1 to 4 carbon atoms in the alkyl radical and is linked to the N atom via the carbonyl group. There may be mentioned by way of example and preferably: acetylamino, propionylamino, n-butyrylamino, iso-butyrylamino, n-pentanoylamino, and pivaloylamino.

($C_3$-$C_6$)-Cycloalkyl in the context of the invention represents a monocyclic, saturated carbocycle having 3 to 6 ring carbon atoms. There may be mentioned by way of example: cyclopropyl, cyclobutyl, cyclopentyl, and cyclohexyl. Preferred are cyclopropyl and cyclobutyl.

4- to 7-membered heterocycloalkyl and 4- to 6-membered heterocycloalkyl in the context of the invention represent a monocyclic, saturated heterocycle with 4 to 7 or, respectively, 4 to 6 ring atoms in total, which contains one or two identical or different ring heteroatoms from the series N, O, S and S(O)$_2$, and which can be bonded via a ring carbon atom or via a ring nitrogen atom (if present). 4- to 6-membered heterocycloalkyl containing one ring nitrogen atom and optionally one further ring heteroatom from the series N, O or S(O)$_2$ is preferred. 5- or 6-membered heterocycloalkyl containing one ring nitrogen atom and optionally one further ring heteroatom from the series N or O is particularly preferred. There may be mentioned by way of example: azetidinyl, oxetanyl, thietanyl, pyrrolidinyl, pyrazolidinyl, imidazolidinyl, tetrahydrofuranyl, thiolanyl, 1,1-dioxidothiolanyl, 1,2-oxazolidinyl, 1,3-oxazolidinyl, 1,3-thiazolidinyl, piperidinyl, piperazinyl, tetrahydropyranyl, tetrahydrothiopyranyl, 1,3-dioxanyl, 1,4-dioxanyl, 1,2-oxazinanyl, morpholinyl, thiomorpholinyl, 1,1-dioxidothiomorpholinyl, azepanyl, 1,4-diazepanyl, and 1,4-oxazepanyl. Preferred are azetidinyl, pyrrolidinyl, pyrazolidinyl, imidazolidinyl, 1,2-oxazolidinyl, 1,3-oxazolidinyl, piperidinyl, piperazinyl, 1,2-oxazinanyl, morpholinyl, and thiomorpholinyl. Particularly preferred are pyrrolidinyl, piperidinyl, piperazinyl, and morpholinyl.

Pyrrolidino, piperidino and morpholino in the context of the invention specifically refer to an N-bonded pyrrolidin-1-yl, piperidin-1-yl and morpholin-4-yl ring, respectively.

An oxo substituent in the context of the invention represents an oxygen atom, which is bonded to a carbon atom via a double bond.

In the context of the present invention, for all the radicals which occur several times, the meaning thereof is independent of each other. If radicals in the compounds according to the invention are substituted, the radicals can be mono- or polysubstituted, unless specified otherwise. Substitution by one or by two or three identical or different substituents is preferred. Substitution by one or by two identical or different substituents is particularly preferred.

In a preferred embodiment, the present invention relates to compounds of general formula (I), wherein $R^1$ is hydrogen, chloro, methyl or methoxy,
$R^2$ is hydrogen or methoxy,
   with the proviso that at least one of $R^1$ and $R^2$ is other than hydrogen,
and
G represents the group —CH$_2$—OR$^3$, —C(=O)—OR$^3$, —CH$_2$—NR$^4$R$^5$ or —C(=O)—NR$^4$R$^6$, wherein
   $R^3$ is hydrogen or ($C_1$-$C_4$)-alkyl optionally substituted with hydroxy, ($C_1$-$C_4$)-alkoxy, hydroxycarbonyl, ($C_1$-$C_4$)-alkoxycarbonyl, amino, aminocarbonyl, mono-($C_1$-$C_4$)-alkylaminocarbonyl, di-($C_1$-$C_4$)-alkylaminocarbonyl or up to three fluoro atoms,
   $R^4$ is hydrogen or ($C_1$-$C_4$)-alkyl,
   $R^5$ is hydrogen, ($C_1$-$C_4$)-alkyl, ($C_1$-$C_4$)-alkylcarbonyl, ($C_3$-$C_6$)-cycloalkyl or 4- to 6-membered heterocycloalkyl, wherein (i) said ($C_1$-$C_4$)-alkyl is optionally substituted with hydroxy, ($C_1$-$C_4$)-alkoxy, ($C_1$-$C_4$)-alkoxycarbonyl, aminocarbonyl, mono-($C_1$-$C_4$)-alkylaminocarbonyl, di($C_1$-$C_4$)-alkylaminocarbonyl or ($C_1$-$C_4$)-alkylcarbonylamino,
and
(ii) said ($C_3$-$C_6$)-cycloalkyl is optionally substituted with one or two substituents independently selected from the group consisting of ($C_1$-$C_4$)-alkyl, hydroxy, amino and ($C_1$-$C_4$)-alkylcarbonylamino,
and
(iii) said 4- to 6-membered heterocycloalkyl is optionally substituted with one or two substituents independently selected from the group consisting of ($C_1$-$C_4$)alkyl, hydroxy, oxo, amino and ($C_1$-$C_4$)-alkylcarbonylamino, $R^6$ is hydrogen, ($C_1$-$C_4$)-alkyl, ($C_3$-$C_6$)-cycloalkyl or 4- to 6-membered heterocycloalkyl, wherein
(i) said ($C_1$-$C_4$)-alkyl is optionally substituted with hydroxy, ($C_1$-$C_4$)-alkoxy, ($C_1$-$C_4$)-alkoxycarbonyl, amino, aminocarbonyl, mono-($C_1$-$C_4$)-alkylaminocarbonyl, di-($C_1$-$C_4$)-alkylaminocarbonyl or ($C_1$-$C_4$)-alkylcarbonylamino,
and
(ii) said ($C_3$-$C_6$)-cycloalkyl is optionally substituted with one or two substituents independently selected from the group consisting of ($C_1$-$C_4$)-alkyl, hydroxy, amino and ($C_1$-$C_4$)-alkylcarbonylamino,
and
(iii) said 4- to 6-membered heterocycloalkyl is optionally substituted with one or two substituents independently selected from the group consisting of ($C_1$-$C_4$)alkyl, hydroxy, oxo, amino and ($C_1$-$C_4$)-alkylcarbonylamino,
or
$R^4$ and $R^5$, or $R^4$ and $R^6$, respectively, are joined and, taken together with the nitrogen atom to which they are attached, form a monocyclic, saturated 4- to 7-membered heterocycloalkyl ring which may contain a second ring heteroatom selected from $N(R^7)$ and O, and which may be substituted on ring carbon atoms with up to three substituents independently selected from the group consisting of ($C_1$-$C_4$)-alkyl, oxo, hydroxy, amino and aminocarbonyl, and wherein
$R^7$ is hydrogen, ($C_1$-$C_4$)-alkyl, formyl, ($C_1$-$C_4$)-alkylcarbonyl or ($C_1$-$C_4$)-alkoxycarbonyl.

In a more preferred embodiment, the present invention relates to compounds of general formula (I), wherein
$R^1$ is hydrogen, chloro, methyl or methoxy,
$R^2$ is methoxy,
and
G represents the group —$CH_2$—$OR^3$, —$CH_2$—$NR^4R^5$ or —C(=O)—$NR^4R^6$, wherein
$R^3$ is hydrogen or ($C_1$-$C_4$)-alkyl optionally substituted with hydroxy, ($C_1$-$C_4$)-alkoxycarbonyl, amino or aminocarbonyl,
$R^4$ is hydrogen or methyl,
$R^5$ is ($C_1$-$C_4$)-alkyl, ($C_1$-$C_4$)-alkylcarbonyl or 5- or 6-membered heterocycloalkyl, wherein
(i) said ($C_1$-$C_4$)-alkyl is optionally substituted with hydroxy, ($C_1$-$C_4$)-alkoxycarbonyl, aminocarbonyl, mono-($C_1$-$C_4$)-alkylaminocarbonyl or ($C_1$-$C_4$)-alkylcarbonylamino,
and
(ii) said 5- or 6-membered heterocycloalkyl is optionally substituted with oxo, $R^6$ is hydrogen or ($C_1$-$C_4$)-alkyl optionally substituted with hydroxy, amino or aminocarbonyl,
or
$R^4$ and $R^5$, or $R^4$ and $R^6$, respectively, are joined and, taken together with the nitrogen atom to which they are attached, form a monocyclic, saturated 4- to 6-membered heterocycloalkyl ring which may contain a second ring heteroatom selected from $N(R^7)$ and O, and which may be substituted on ring carbon atoms with one or two substituents independently selected from the group consisting of methyl, oxo, hydroxy, amino and aminocarbonyl, and wherein
$R^7$ is hydrogen, ($C_1$-$C_4$)-alkyl, ($C_1$-$C_4$)-alkylcarbonyl or ($C_1$-$C_4$)-alkoxycarbonyl.

In a distinct embodiment, the present invention relates to compounds of general formula (I), wherein
$R^1$ is methyl,
and
$R^2$ is methoxy.

In a further distinct embodiment, the present invention relates to compounds of general formula (I), wherein
G represents the group —$CH_2$—$OR^3$, wherein
$R^3$ is hydrogen or ($C_1$-$C_4$)-alkyl optionally substituted with hydroxy, amino or aminocarbonyl.

In another distinct embodiment, the present invention relates to compounds of general formula (I), wherein
G represents the group —$CH_2$—$NR^4R^5$, wherein
$R^4$ is hydrogen or methyl,
and
$R^5$ is ($C_1$-$C_4$)-alkyl optionally substituted with hydroxy, aminocarbonyl or methylaminocarbonyl, or is acetyl or 2-oxopyrrolidin-3-yl.

In yet another distinct embodiment, the present invention relates to compounds of general formula (I), wherein
G represents the group —$CH_2$—$NR^4R^5$, wherein
$R^4$ and $R^5$ are joined and, taken together with the nitrogen atom to which they are attached, form a monocyclic, saturated 5- or 6-membered heterocycloalkyl ring which may contain a second ring heteroatom selected from $N(R^7)$ and O, and which may be substituted on a ring carbon atom with oxo, hydroxy or aminocarbonyl, and wherein
$R^7$ is hydrogen, methyl, acetyl or tert-butoxycarbonyl.

In a particularly preferred embodiment, the present invention relates to compounds of general formula (I), wherein
$R^1$ is methyl,
$R^2$ is methoxy,
and
G represents the group —$CH_2$—$OR^3$ or —$CH_2$—$NR^4R^5$, wherein
$R^3$ is ($C_1$-$C_4$)-alkyl optionally substituted with hydroxy, amino or aminocarbonyl,
$R^4$ is hydrogen or methyl,
$R^5$ is ($C_1$-$C_4$)-alkyl substituted with hydroxy or aminocarbonyl, or is acetyl or 2-oxopyrrolidin-3-yl,
or
$R^4$ and $R^5$ are joined and, taken together with the nitrogen atom to which they are attached, form a monocyclic, saturated 5- or 6-membered heterocycloalkyl ring which may contain a second ring heteroatom selected from $N(R^7)$ and O, and which may be substituted on a ring carbon atom with oxo, hydroxy or aminocarbonyl, and wherein
$R^7$ is hydrogen or acetyl.

The definitions of residues indicated specifically in the respective combinations or preferred combinations of residues are also replaced as desired by definitions of residues of other combinations, irrespective of the particular combinations indicated for the residues. Combinations of two or more of the abovementioned preferred ranges are particularly preferred.

The compounds of the general formula (I) can be prepared by various synthetic routes which are primarily governed by the nature of the particular G group chosen (see definitions above).

Thus, in another embodiment, the present invention relates to a process for preparing the compounds of the general formula (I), characterized in that a 6-(hydroxymethyl)-substituted 4-amino-5-bromopyrrolo[2,1-f][1,2,4]triazine of formula (II)

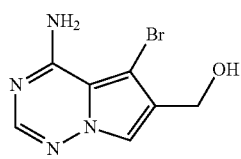
(II)

is coupled with a benzothiophen-2-yl boronate of formula (III)

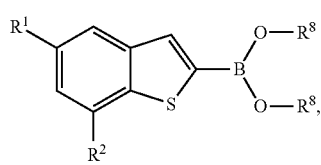
(III)

wherein $R^1$ and $R^2$ have the meanings described above, and $R^8$ represents hydrogen or $(C_1-C_4)$-alkyl, or both $R^8$ residues are linked together to form a —$(CH_2)_2$—, —$C(CH_3)_2$—$C(CH_3)_2$—, —$(CH_2)_3$—, —$CH_2$—$C(CH_3)_2$—$CH_2$— or —$C(=O)$—$CH_2$—$N(CH_3)$—$CH_2$—$C(=O)$— bridge, in the presence of a palladium catalyst and a base to yield the compound of formula (I-A)

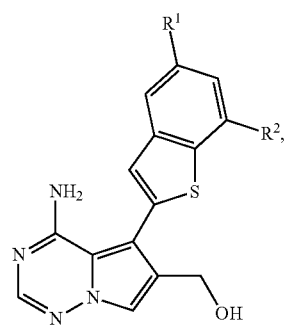
(I-A)

wherein $R^1$ and $R^2$ have the meanings described above, which optionally is either

[A] converted into the corresponding 6-(halomethyl) derivative of formula (IV)

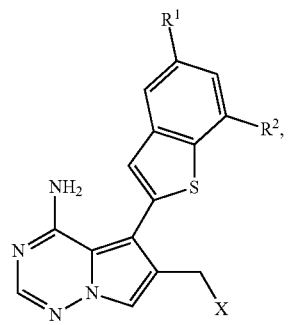
(IV)

wherein $R^1$ and $R^2$ have the meanings described above, and

X is chloro, bromo or iodo, and then reacted in the presence of a base with an alcohol of formula (V) or with an amine of formula (VII-A)

wherein $R^4$ has the meaning described above, and $R^{3A}$ and $R^{5A}$ have the meaning of $R^3$ and $R^5$, respectively, as described above, except for hydrogen, to give the target compounds of formula (I-B) and formula (I-C1), respectively,

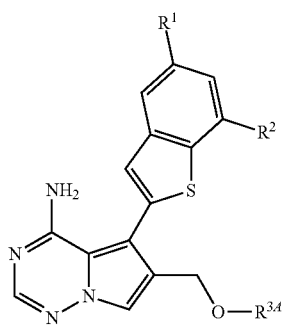
(I-B)

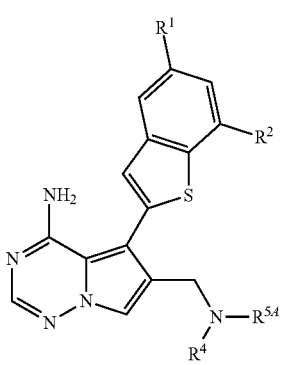
(I-C1)

wherein $R^1$, $R^2$, $R^{3A}$, $R^4$ and $R^{5A}$ have the meanings described above, or

[B] oxidized to the aldehyde of formula (VI)

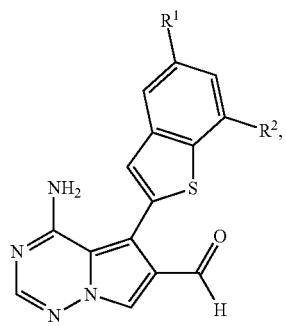

wherein R¹ and R² have the meanings described above,
and then reacted with an amine of formula (VII)

wherein R⁴ and R⁵ have the meanings described above,
in the presence of an acid and a reducing agent to give the
target compound of formula (I-C)

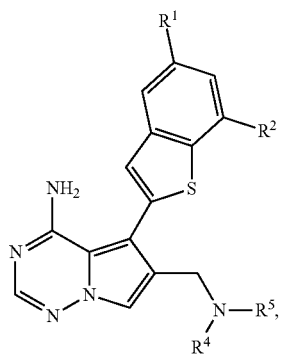

wherein R¹, R², R⁴ and R⁵ have the meanings described above, or

[C] oxidized to the carboxylic acid of formula (I-D)

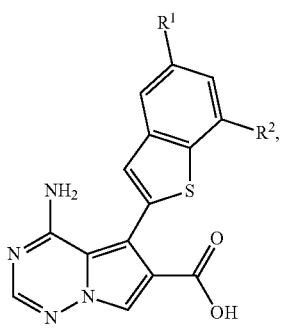

wherein R¹ and R² have the meanings described above,
and then coupled with an alcohol of formula (V) or with an amine of formula (VIII)

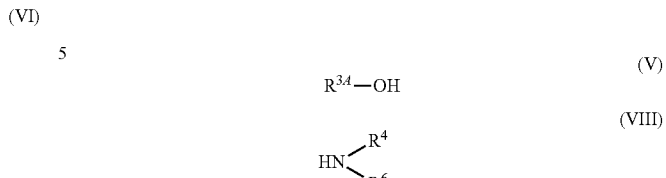

wherein $R^{3A}$, $R^4$ and $R^6$ have the meanings described above,
in the presence of a condensing agent to give the target compounds of formula (I-E) and formula (I-F), respectively,

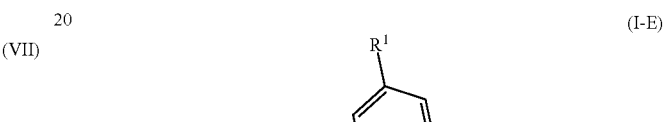

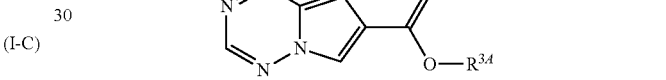

wherein $R^1$, $R^2$, $R^{3A}$, $R^4$ and $R^6$ have the meanings described above, optionally followed, where appropriate, by (i) separating the compounds of formula (I) thus obtained into their respective enantiomers and/or diastereomers, preferably using chromatographic methods, and/or (ii) converting the compounds of formula (I) into their respective hydrates, solvates, salts and/or hydrates or solvates of the salts by treatment with the corresponding solvents and/or acids or bases.

In a modification of process [B] following a reversed reaction sequence, the compounds of formula (I-C) can also be prepared by first oxidizing the 6-(hydroxymethyl)-substituted 4-amino-5-bromopyrrolo[2,1-f][1,2,4]triazine of formula (II)

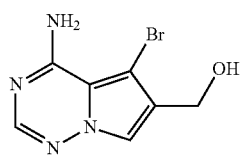
(II)

to the aldehyde of formula (IX)

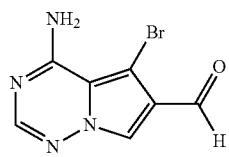
(IX)

and then reacting the latter with an amine of formula (VII)

(VII)

wherein R⁴ and R⁵ have the meanings described above, in the presence of an acid and a reducing agent to yield the compound of formula (X)

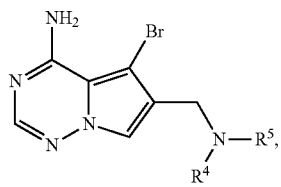
(X)

wherein R⁴ and R⁵ have the meanings described above, which is subsequently coupled with a benzothiophen-2-yl boronate of formula (III)

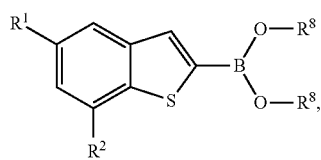
(III)

wherein $R^1$, $R^2$ and $R^8$ have the meanings described above, in the presence of a palladium catalyst and a base to give the target compound of formula (I-C)

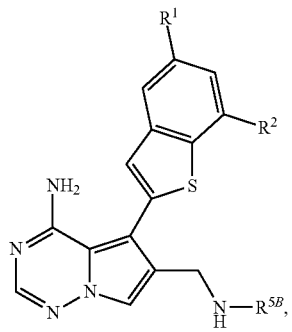
(I-C)

wherein $R^1$, $R^2$, $R^4$ and $R^5$ have the meanings described above.

Compounds of the invention having the formula (I-G)

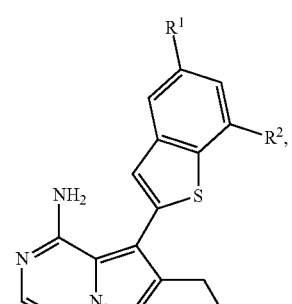
(I-G)

wherein $R^1$ and $R^2$ have the meanings described above, and $R^{5B}$ is hydrogen or ($C_1$-$C_4$)-alkylcarbonyl, can be prepared by treating the 6-(halomethyl) intermediate of formula (IV)

(IV)

wherein $R^1$, $R^2$ and X have the meanings described above, with an azide, such as sodium azide, to give the corresponding 6-(azidomethyl) derivative of formula (XI)

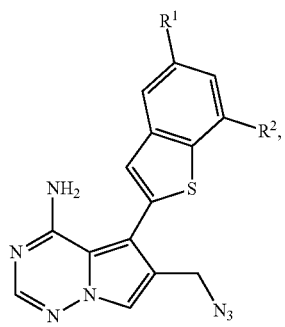

(XI)

wherein R¹ and R² have the meanings described above, which is then hydrogenated under palladium catalysis to the 6-(aminomethyl) compound of formula (I-G1)

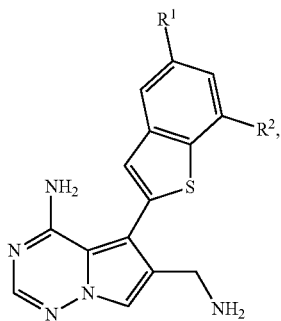

(I-G1)

wherein R¹ and R² have the meanings described above, and optionally acylated with a carboxylic acid derivative of formula (XII) or (XIII)

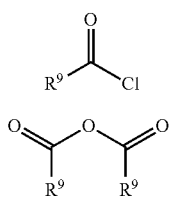

(XII)

(XIII)

wherein
R⁹ is $(C_1-C_4)$-alkyl,
to yield the target compound of formula (I-G2)

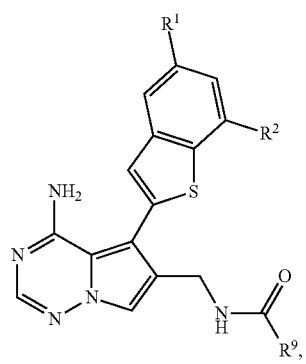

(I-G2)

wherein R¹, R² and R⁹ have the meanings described above.

The compounds of the formulae (I-A), (I-B), (I-C), (I-C1), (I-D), (I-E), (I-F), (I-G), (I-G1) and (I-G2), which can be prepared by the processes described above, each represent a particular subset of the compounds of the general formula (I).

The coupling reactions (II)+(III)→(I-A) and (X)+(III)→(I-C) ["Suzuki-Miyaura coupling"] are generally carried out in an inert solvent with the aid of a palladium catalyst and an aqueous base. Palladium catalysts suitable for this purpose include, for example, palladium(II) acetate, palladium (II) chloride, bis(triphenylphosphine)palladium(II) chloride, bis(acetonitrile)palladium(II) chloride, [1,1'-bis(diphenylphosphino)ferrocene]palladium(II) chloride, tetrakis(triphenylphosphine)palladium(0), bis(dibenzylideneacetone)palladium(0), and tris(dibenzylideneacetone)dipalladium(0), optionally in combination with other phosphine ligands such as, for example, 2-dicyclohexylphosphino-2',4',6'-triisopropylbiphenyl (X-Phos), 2-dicyclohexylphosphino-2',6'-dimethoxybiphenyl (S-Phos), 4,5-bis(diphenylphosphino)-9,9-dimethylxanthene (Xantphos), or 4-(di-tert-butylphosphino)-N,N-dimethylaniline. Also, palladium pre-catalysts from which the catalytically active species is generated under the reaction conditions, such as (2'-aminobiphenyl-2-yl)(chloro)palladium-dicyclohexyl(2',4',6'-triisopropylbiphenyl-2-yl)phosphine, can be used [see, for example, S. Kotha et al., *Tetrahedron* 58, 9633-9695 (2002); T. E. Barder et al., *J. Am. Chem. Soc.* 127 (13), 4685-4696 (2005); S. L. Buchwald et al., *J. Am. Chem. Soc.* 132 (40), 14073-14075 (2010), and further references cited therein].

Suitable bases for these coupling reactions are in particular alkali carbonates, such as sodium, potassium or caesium carbonate, alkali phosphates, such as sodium or potassium phosphate, or alkali fluorides, such as potassium or caesium fluoride. Usually, these bases are employed as aqueous solutions. The reactions are carried out in organic solvents that are inert under the reaction conditions. Preferably, water-miscible organic solvents, such as 1,2-dimethoxyethane, tetrahydrofuran, 1,4-dioxane, acetonitrile, N,N-dimethylformamide (DMF) or dimethylsulfoxide (DMSO), are employed but other inert solvents, such as dichloromethane or toluene, may also be used.

For the hydroxy-to-halogen transformation (I-A)→(IV), various standard methods and reagents that are well known in the art may be employed. Reagents of choice are thionyl chloride [for X=Cl], tetrabromomethane/triphenylphosphine [for X=Br], and iodine/triphenylphosphine [for X=I]. The preparation of 6-(chloromethyl) derivatives (IV) [X=Cl] is preferred for reasons of convenience of work-up and compound stability.

Bases suitable for the process steps (IV)+(V)→(I-B) and (IV)+(VII-A)→(I-C1) are in particular alkali carbonates such as lithium, sodium, potassium or caesium carbonate, alkali acetates such as sodium or potassium acetate, or customary tertiary amine bases such as triethylamine, N-methylmorpholine, N-methylpiperidine, N,N-diisopropylethylamine or pyridine. Preference is given to N,N-diisopropylethylamine (DIPEA). The reactions are performed in an inert solvent, such as tetrahydrofuran, or without solvent, using an excess of alcohol (V) or amine (VII-A), at a temperature ranging from +20° C. to +200° C., preferably at +50° C. to +150° C. Advantageously, these conversions are carried out by means of a microwave reactor device.

The reaction sequences (I-A)→(IV)→(I-B), (I-A)→(IV)→(I-C1) and (I-A)→(IV)→(XI) may each be carried out in two separate steps, i.e. with isolation and purification of the intermediate compound (IV), or they may be performed using a one-pot procedure, i.e. employing the crude intermediate (IV) as obtained in the preparation reaction.

Oxidizing agents that are capable of converting primary alcohols (I-A) and (II) into aldehydes (VI) and (IX), respectively, under mild conditions include 1,1,1-triacetoxy-1,1-dihydro-1,2-benziodoxol-3(1H)-one ("Dess-Martin periodinane"), 2,2,6,6-tetramethylpiperidin-1-oxyl (TEMPO) in combination with secondary oxidants such as iodosobenzene-I,I-diacetate or sodium hypochlorite, and dimethylsulfoxide (DMSO)-based oxidation systems such as DMSO/trifluoroacetic anhydride or DMSO/N,N'-dicyclohexylcarbodiimide (DCC). Preference is given to 1,1,1-triacetoxy-1,1-dihydro-1,2-benziodoxol-3(1H)-one. The oxidation reactions are carried out in an inert solvent, preferably using dichloromethane.

Reducing agents suitable for the reductive amination reactions (VI)+(VII)→(I-C) and (IX)+(VII)→(X) are customary alkali borohydrides, such as lithium borohydride, sodium borohydride, potassium borohydride, sodium cyanoborohydride or sodium triacetoxyborohydride. The transformations are generally carried out in the presence of an acid, preferably acetic acid, in an alcohol or ether solvent, such as methanol, ethanol, isopropanol, tetrahydrofuran or 1,4-dioxane, within a temperature range from 0° C. to +80° C., depending on the reactivity of the amine component (VII) and/or the particular borohydride used.

The preparation of the carboxylic acid (I-D) can be accomplished either by single-step oxidation of the alcohol (I-A) or by further oxidation of the aldehyde intermediate (VI). For the first route, sodium hypochlorite in the presence of 2,2,6,6-tetramethylpiperidin-1-oxyl (TEMPO) radical as catalyst, or stoichiometric sodium chlorite together with catalytic amounts of TEMPO and sodium hypochlorite may favourably be used as oxidant [cf. H. van Bekkum et al., *Synthesis*, 1153-1174 (1996); M. M. Zhao et al., *Org. Synth.* 81, 195-203 (2005), and references cited therein]. For the second route, oxidation with sodium chlorite in the presence of a hypochlorite scavenger such as 2-methyl-2-butene represents the method of choice [cf. H. W. Pinnick et al., *Tetrahedron* 37, 2091-2096 (1981); A. Raach and O. Reiser, *J. Prakt. Chem.* 342 (6), 605-608 (2000), and references cited therein]. In the context of the present invention, preference is given to a two-step oxidation procedure (I-A)→(VI)→(I-D).

Condensing agents suitable for process steps (I-D)+(V)→(I-E) [ester formation] and (I-D)+(VIII)→(I-F) [amide formation] include, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide (EDC), phosgene derivatives such as N,N'-carbonyldiimidazole (CDI) or isobutyl chloroformate, α-chloroenamines such as 1-chloro-2-methyl-1-dimethylamino-1-propene, phosphorus compounds such as propanephosphonic anhydride, diethyl cyanophosphonate, bis(2-oxo-3-oxazolidinyl)phosphoryl chloride, benzotriazol-1-yloxy-tris(dimethylamino)phosphonium hexafluorophosphate (BOP) or benzotriazol-1-yloxy-tris(pyrrolidino)phosphonium hexafluorophosphate (PyBOP), and uronium compounds such as O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), if appropriate in combination with further auxiliaries, such as 1-hydroxybenzotriazole (HOBt) or N-hydroxysuccinimide (HOSu), and/or bases such as alkali carbonates, for example sodium carbonate or potassium carbonate, or organic amine bases, such as triethylamine, N-methylpiperidine, N-methylmorpholine (NMM), N,N-diisopropylethylamine (DIPEA), pyridine or 4-N,N-dimethylaminopyridine (DMAP). Preference is given to using O-(7-azabenzotriazol-1-yl)-N,N,N',N'-tetramethyluronium hexafluorophosphate (HATU) or O-(benzotriazol-1-yl)-N,N,N',N'-tetramethyluronium tetrafluoroborate (TBTU) in combination with N,N-diisopropylethylamine (DIPEA) and/or 1-hydroxybenzotriazole (HOBt), as appropriate.

Inert solvents for process steps (I-D)+(V)→(I-E) and (I-D)+(VIII)→(I-F) are, for example, ethers such as diethyl ether, tert-butyl methyl ether, tetrahydrofuran, 1,4-dioxane or 1,2-dimethoxyethane, hydrocarbons such as benzene, toluene, xylene, hexane or cyclohexane, halogenated hydrocarbons such as dichloromethane, trichloromethane, carbon tetrachloride, 1,2-dichloroethane, trichloroethylene or chlorobenzene, or other solvents such as acetone, acetonitrile, ethyl acetate, pyridine, dimethylsulfoxide (DMSO), N,N-dimethylformamide (DMF), N,N'-dimethylpropyleneurea (DMPU) or N-methylpyrrolidinone (NMP). It is also possible to use mixtures of these solvents. Preference is given to using dichloromethane, tetrahydrofuran, dimethylformamide or mixtures thereof. The reactions are generally carried out at a temperature ranging from 0° C. to +60° C., preferably at +10° C. to +40° C.

In cases where a primary or secondary amine moiety forms part of the G group in the target compounds of formula (I), it may sometimes be appropriate in the preparation reactions described above to use a protected derivative of this amine as reaction component instead of the free amine. For this purpose, conventional temporary amino-protecting groups, such as acyl groups (e.g., acetyl or trifluoroacetyl) or carbamate-type protecting groups (e.g., a Boc-, Cbz- or Fmoc-group), may be employed. A Boc (tert-butoxycarbonyl) group is preferably used. Similarly, a hydroxy function being part of the G group may temporarily be blocked in precursor compounds and process intermediates, for example as a tetrahydropyranyl (THP) ether or as a silyl ether derivative, such as a trimethylsilyl or tert-butyldimethylsilyl ether.

These protecting groups may then be cleaved off concomitantly during aqueous work-up and purification procedures, or they are removed in a subsequent, separate reaction step using standard methods well known in the art. The preparation of such protected intermediates from the corresponding free amines or alcohols is likewise readily accomplished following general procedures described in the literature [see, for example, T. W. Greene and P. Wuts, *Protective Groups in Organic Synthesis*, Wiley, New York, 1999].

Certain types of protected (i.e. acylated) amine derivatives exert significant FGFR-inhibiting activity by their own. Accordingly, such compounds are also encompassed by the general formula (I) as defined above.

The preparation of the compounds of the invention may be illustrated by means of the following synthesis schemes:

Scheme 1

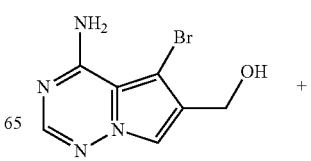
+

21
-continued
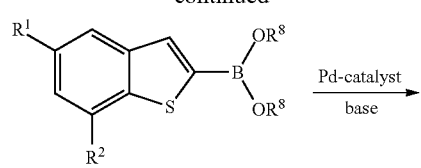
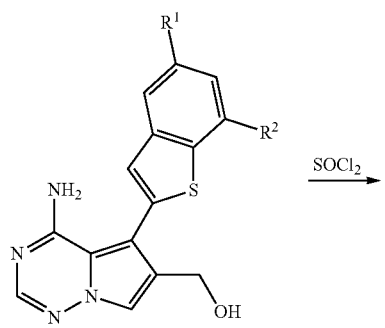
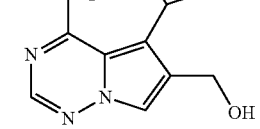
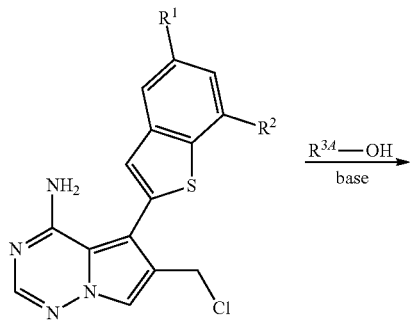
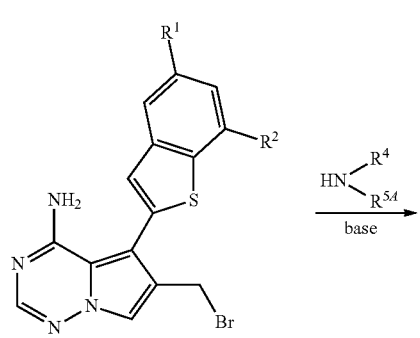
22
-continued
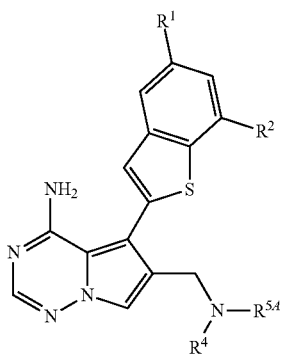
Scheme 2
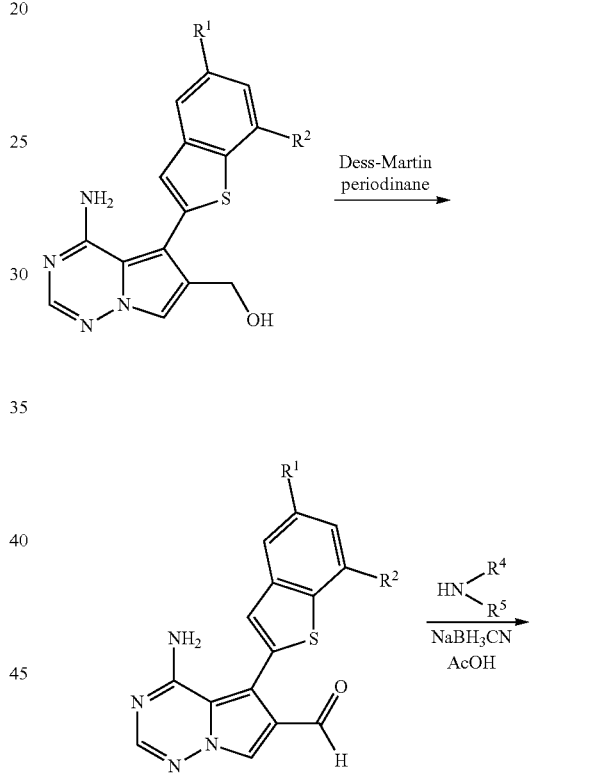
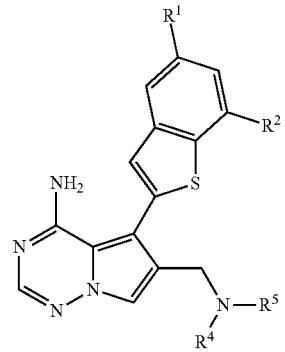

Scheme 3

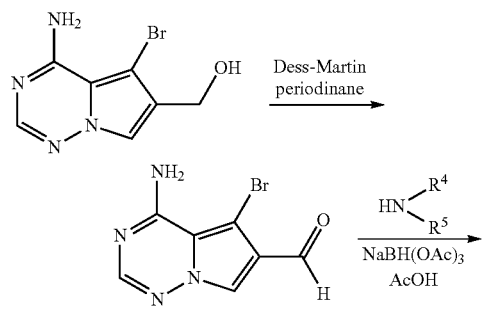

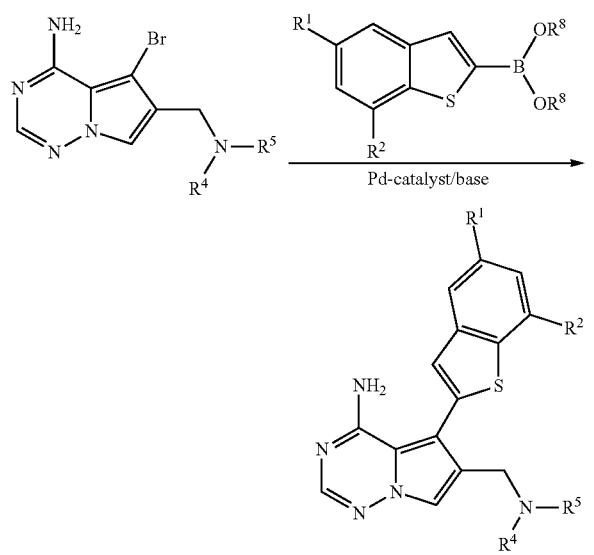

Scheme 4

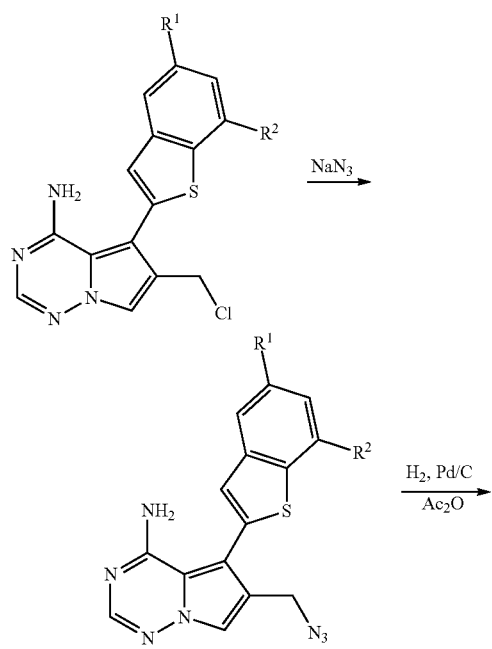

Scheme 5

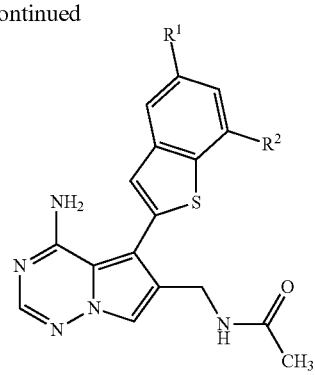

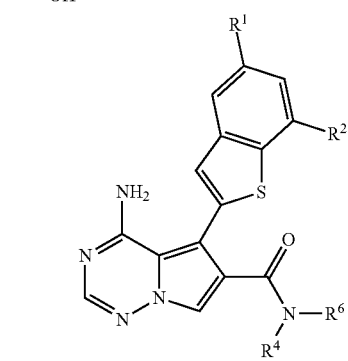

The starting compound 4-amino-5-bromo-6-(hydroxymethyl)pyrrolo[2,1-f][1,2,4]triazine of formula (II) is readily available from 4-amino-6-cyanopyrrolo[2,1-f][1,2,4]triazine (XIV) by acid-mediated alcoholysis to the ester (XV), subsequent reduction to the 6-(hydroxymethyl) derivative (XVI) using lithium triethylborohydride, dibromination with 1,3-dibromo-5,5-dimethylhydantoin, and, finally, selective debromination in 7-position by halogen-metal exchange with n-butyllithium followed by methanol quenching (see Scheme 6 below). The preparation of 4-amino-6-cyanopyrrolo[2,1-f]-[1,2,4]triazine (XIV) has been described previously [see Int. Pat. Appl. WO 2007/064883-A2 (Intermediate AX/Step 3)].

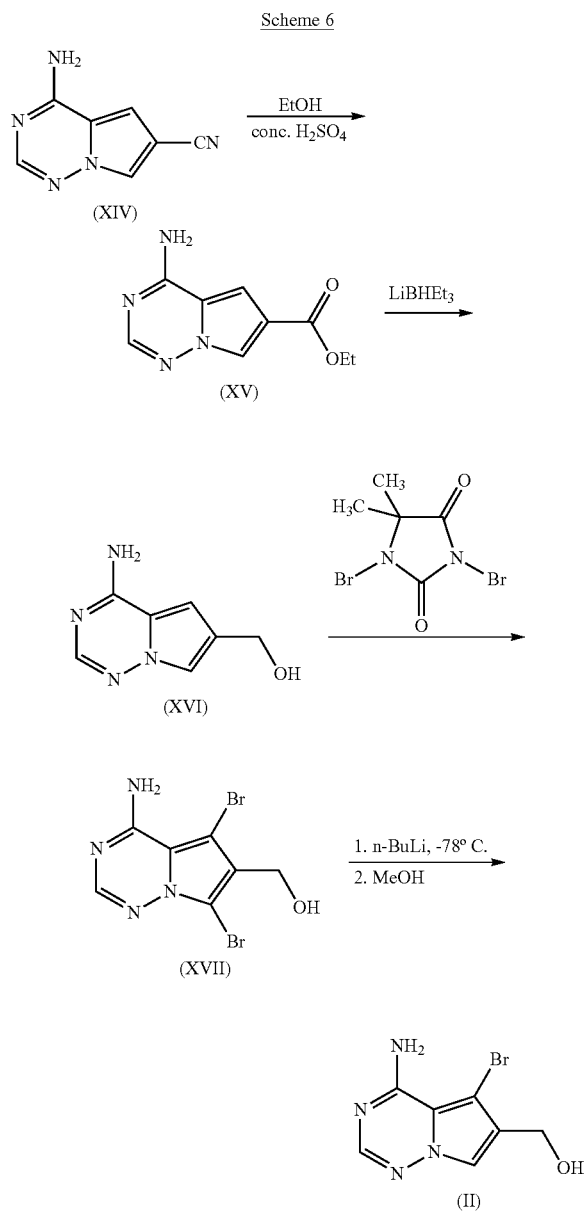

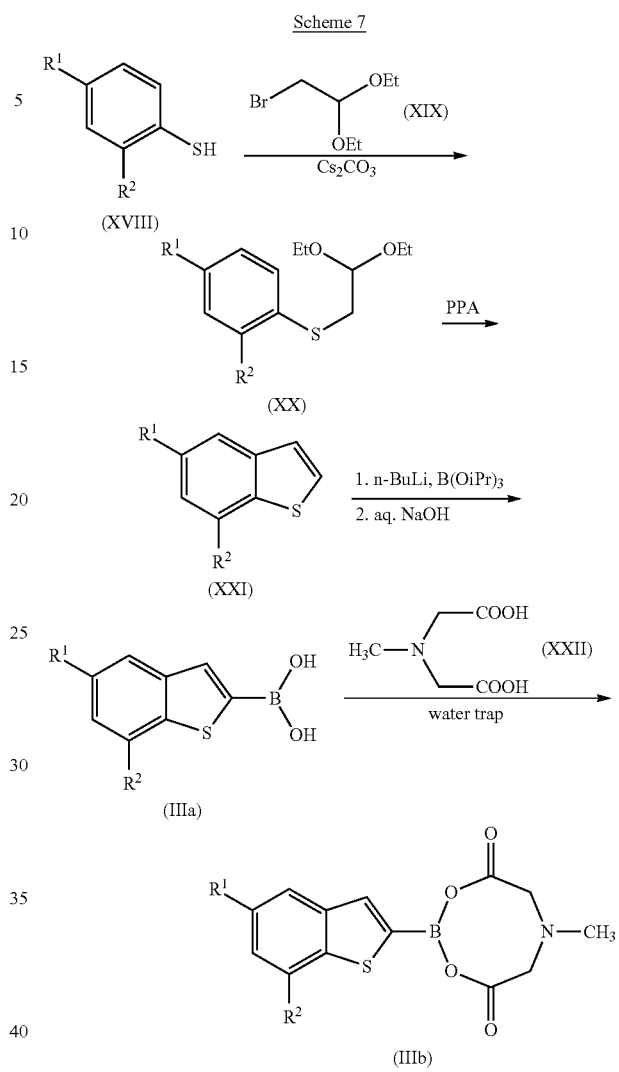

[cf. P. A. Plé and L. J. Marnett, *J. Heterocyclic Chem.* 25 (4), 1271-1272 (1988); A. Venturelli et al., *J. Med. Chem.* 50 (23), 5644-5654 (2007)].

The compounds of the formulae (V), (VII), (VII-A), (VIII), (XVIII), (XIX) and (XXII) are either commercially available, known from the literature, or can be prepared from readily available starting materials by adaptation of standard methods described in the literature. Detailed procedures and literature references for preparing the starting materials can also be found in the Experimental Part in the section on the preparation of the starting materials and intermediates.

The benzothiophen-2-yl boronates of formula (III) can conveniently be prepared starting from the substituted thiophenol derivatives of formula (XVIII) (see Scheme 7 below). Alkylation with bromoacetal (XIX) and subsequent polyphosphoric acid-mediated cyclization provides the benzothiophene intermediates of formula (XXI) which are then metalated in 2-position and reacted with a trialkyl borate. Alkaline work-up affords the free (benzothiophen-2-yl)boronic acids of formula (IIIa) which may be transformed, if desired, into cyclic boronates, e.g. so-called MIDA boronates of formula (IIIb), by standard procedures known in the art [see, for example, D. M. Knapp et al., *J. Am. Chem. Soc.* 131 (20), 6961-6963 (2009)].

The compounds of the present invention have valuable pharmacological properties and can be used for the prevention and treatment of disorders in humans and other mammals.

The compounds of the present invention are potent inhibitors of the activity or expression of receptor tyrosine kinases, particularly of the FGFR kinases, and most notably of the FGFR-1 and FGFR-3 kinases. Accordingly, in another embodiment, the present invention provides a method of treating disorders relating to or mediated by the activity of FGFR kinases in a patient in need of such treatment, comprising administering to the patient an effective amount of a compound of formula (I) as defined above. In certain embodiments, the disorders relating to the activity of FGFR kinases are proliferative disorders, in particular cancer and tumor diseases.

In the context of the present invention, the term "treatment" or "treating" includes inhibiting, delaying, relieving, mitigating, arresting, reducing, or causing the regression of a disease, disorder, condition, or state, the development and/or progression thereof, and/or the symptoms thereof. The term "prevention" or "preventing" includes reducing the risk of having, contracting, or experiencing a disease, disorder, condition, or state, the development and/or progression thereof, and/or the symptoms thereof. The term prevention includes prophylaxis. Treatment or prevention of a disorder, disease, condition, or state may be partial or complete.

The term "proliferative disorder" includes disorders involving the undesired or uncontrolled proliferation of a cell. The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, isomer, polymorph, metabolite, hydrate or solvate thereof which is effective to treat or prevent the disorder.

Throughout this document, for the sake of simplicity, the use of singular language is given preference over plural language, but is generally meant to include the plural language if not otherwise stated. For example, the expression "A method of treating a disease in a patient, comprising administering to a patient an effective amount of a compound of formula (I)" is meant to include the simultaneous treatment of more than one disease as well as the administration of more than one compound of formula (I).

Proliferative disorders that can be treated and/or prevented with the compounds of the present invention particularly include, but are not limited to, the group of cancer and tumor diseases. These are understood as meaning, in particular, the following diseases, but without being limited to them: mammary carcinomas and mammary tumors (ductal and lobular forms, also in situ), tumors of the respiratory tract (small cell and non-small cell lung carcinoma, parvicellular and non-parvicellular carcinoma, bronchial carcinoma, bronchial adenoma, pleuropulmonary blastoma), cerebral tumors (e.g. of the brain stem and of the hypothalamus, astrocytoma, glioblastoma, medulloblastoma, ependymoma, and neuro-ectodermal and pineal tumors), tumors of the digestive organs (oesophagus, stomach, gall bladder, small intestine, large intestine, rectum, anus), liver tumors (inter alia hepatocellular carcinoma, cholangiocellular carcinoma and mixed hepatocellular and cholangiocellular carcinoma), tumors of the head and neck region (larynx, hypopharynx, nasopharynx, oropharynx, lips and oral cavity), skin tumors (squamous epithelial carcinoma, Kaposi sarcoma, malignant melanoma, Merkel cell skin cancer and non-melanomatous skin cancer), tumors of soft tissue (inter alia soft tissue sarcomas, osteosarcomas, malignant fibrous histiocytomas, lymphosarcomas and rhabdomyosarcomas), tumors of the eyes (inter alia intraocular melanoma, uveal melanoma and retinoblastoma), tumors of the endocrine and exocrine glands (e.g. thyroid and parathyroid glands, pancreas and salivary gland), tumors of the urinary tract (tumors of the bladder, penis, kidney, renal pelvis and ureter), tumors of the reproductive organs (carcinomas of the endometrium, cervix, ovary, vagina, vulva and uterus in women, and carcinomas of the prostate and testicles in men), as well as distant metastases thereof. These disorders also include proliferative blood diseases in solid form and as circulating blood cells, such as lymphomas, leukaemias and myeloproliferative diseases, e.g. acute myeloid, acute lymphoblastic, chronic lymphocytic, chronic myelogenic and hairy cell leukaemia, and AIDS-related lymphomas, Hodgkin's lymphomas, non-Hodgkin's lymphomas, cutaneous T-cell lymphomas, Burkitt's lymphomas, and lymphomas in the central nervous system.

Due to their activity and selectivity profile, the compounds of the present invention are believed to be particularly suitable for the treatment of breast (mammary), lung, stomach (gastric), bladder and ovary cancer and tumor diseases. Furthermore, the compounds of the present invention may be especially suited for the prevention or suppression of tumor metastasis in general.

Other proliferative disorders that can be treated and/or prevented with the compounds and methods of the present invention include psoriasis, keloids and other hyperplasias affecting the skin, bullous disorders associated with subepidermal blister formation including bullous pemphigoid, erythema multiforme and dermatitis herpetiformis, fibrotic disorders such as lung fibrosis, atherosclerosis, restenosis and hepatic cirrhosis, renal diseases including mesangial cell proliferative disorders, glomerulopathies, glomerulonephritis, diabetic nephropathy, malignant nephrosclerosis and polycystic kidney disease, benign prostate hyperplasia (BPH), angiogenic or blood vessel proliferative disorders, and thrombotic microangiopathy syndromes.

The compounds of the present invention are also useful for the treatment and/or prevention of ophthalmological diseases such as, for example, age-related macular degeneration (AMD), dry macular degeneration, ischemic retinal vein occlusion, diabetic macula edema, diabetic retinopathy, retinopathy of prematurity, and other retinopathies.

Other conditions that may be treated and/or prevented by administering a compound of the present invention include gynaecological diseases such as endometriosis, myoma and ovarian cysts, metabolic disorders related to adipogenesis, bile metabolism, phosphate metabolism, calcium metabolism and/or bone mineralization, skeletal disorders such as, for example, dwarfism, achondrodysplasia and Pfeiffer syndrome, cartilage diseases such as osteoarthritis and polyarthritis, rheumatoid arthritis, calvities, and transplant rejection.

The diseases mentioned above have been well characterized in humans, but also exist with a comparable aetiology in other mammals, and can be treated in those with the compounds and methods of the present invention.

Thus, the present invention further relates to the use of the compounds according to the invention for the treatment and/or prevention of disorders, especially of the aforementioned disorders.

The present invention further relates to the use of the compounds according to the invention for preparing a pharmaceutical composition for the treatment and/or prevention of disorders, especially of the aforementioned disorders.

The present invention further relates to the use of the compounds according to the invention in a method for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

Compounds of the present invention may be administered as the sole pharmaceutical agent or in combination with one or more additional therapeutic agents as long as this combination does not lead to undesirable and/or unacceptable side effects. Such combination therapy includes administration of a single pharmaceutical dosage formulation which contains a compound of formula (I), as defined above, and one or more additional therapeutic agents, as well as administration of a compound of formula (I) and each additional therapeutic agent in its own separate pharmaceutical dosage formulation. For example, a compound of formula (I) and a therapeutic agent may be administered to the patient together in a single (fixed) oral dosage composition such as a tablet or capsule, or each agent may be administered in separate dosage formulations.

Where separate dosage formulations are used, the compound of formula (I) and one or more additional therapeutic agents may be administered at essentially the same time (i.e., concurrently) or at separately staggered times (i.e., sequentially).

In particular, the compounds of the present invention may be used in fixed or separate combination with other anti-cancer agents such as alkylating agents, anti-metabolites, plant-derived anti-tumor agents, hormonal therapy agents, topoisomerase inhibitors, tubulin inhibitors, kinase inhibitors, targeted drugs, antibodies, antibody-drug conjugates (ADCs), immunologicals, biological response modifiers, anti-angiogenic compounds, and other anti-proliferative, cytostatic and/or cytotoxic substances. In this regard, the following is a non-limiting list of examples of secondary agents that may be used in combination with the compounds of the present invention:

Abarelix, abiraterone, aclarubicin, afatinib, aflibercept, aldesleukin, alemtuzumab, alitretinoin, alpharadin, altretamine, aminoglutethimide, amonafide, amrubicin, amsacrine, anastrozole, andromustine, arglabin, asparaginase, axitinib, 5-azacitidine, basiliximab, belotecan, bendamustine, bevacizumab, bexarotene, bicalutamide, bisantrene, bleomycin, bortezomib, bosutinib, brivanib alaninate, buserelin, busulfan, cabazitaxel, CAL-101, calcium folinate, calcium levofolinate, camptothecin, capecitabine, carboplatin, carmofur, carmustine, catumaxomab, cediranib, celmoleukin, cetuximab, chlorambucil, chlormadinone, chlormethine, cidofovir, cisplatin, cladribine, clodronic acid, clofarabine, combretastatin, crisantaspase, crizotinib, cyclophosphamide, cyproterone, cytarabine, dacarbazine, dactinomycin, darbepoetin alfa, darinaparsin, dasatinib, daunorubicin, decitabine, degarelix, denileukin diftitox, denosumab, deslorelin, dibrospidium chloride, docetaxel, dovitinib, doxifluridine, doxorubicin, dutasteride, eculizumab, edrecolomab, eflornithine, elliptinium acetate, eltrombopag, endostatin, enocitabine, epimbicin, epirubicin, epitiostanol, epoetin alfa, epoetin beta, epothilone, eptaplatin, eribulin, erlotinib, estradiol, estramustine, etoposide, everolimus, exatecan, exemestane, exisulind, fadrozole, fenretinide, filgrastim, finasteride, flavopiridol, fludarabine, 5-fluorouracil, fluoxymesterone, flutamide, foretinib, formestane, fotemustine, fulvestrant, ganirelix, gefitinib, gemcitabine, gemtuzumab, gimatecan, gimeracil, glufosfamide, glutoxim, goserelin, histrelin, hydroxyurea, ibandronic acid, ibritumomab tiuxetan, idarubicin, ifosfamide, imatinib, imiquimod, improsulfan, intedanib, interferon alpha, interferon alpha-2a, interferon alpha-2b, interferon beta, interferon gamma, interleukin-2, ipilimumab, irinotecan, ixabepilone, lanreotide, lapatinib, lasofoxifene, lenalidomide, lenograstim, lentinan, lenvatinib, lestaurtinib, letrozole, leuprorelin, levamisole, linifanib, linsitinib, lisuride, lobaplatin, lomustine, lonidamine, lurtotecan, mafosfamide, mapatumumab, masitinib, masoprocol, medroxyprogesterone, megestrol, melarsoprol, melphalan, mepitiostane, mercaptopurine, methotrexate, methyl aminolevulinate, methyltestosterone, mifamurtide, mifepristone, miltefosine, miriplatin, mitobronitol, mitoguazone, mitolactol, mitomycin, mitotane, mitoxantrone, molgramostim, motesanib, nandrolone, nedaplatin, nelarabine, neratinib, nilotinib, nilutamide, nimotuzumab, nimustine, nitracrine, nolatrexed, ofatumumab, oprelvekin, oxaliplatin, paclitaxel, palifermin, pamidronic acid, panitumumab, pazopanib, pegaspargase, peg-epoetin beta, pegfilgastrim, peg-interferon alpha-2b, pelitrexol, pemetrexed, pemtumomab, pentostatin, peplomycin, perfosfamide, perifosine, pertuzumab, picibanil, pirambicin, pirarubicin, plerixafor, plicamycin, poliglusam, polyestradiol phosphate, ponatinib, porfimer sodium, pralatrexate, prednimustine, procarbazine, procodazole, PX-866, quinagolide, raloxifene, raltitrexed, ranibizumab, ranimustine, razoxane, regorafenib, risedronic acid, rituximab, romidepsin, romiplostim, rubitecan, saracatinib, sargramostim, satraplatin, selumetinib, sipuleucel-T, sirolimus, sizofiran, sobuzoxane, sorafenib, streptozocin, sunitinib, talaporfin, tamibarotene, tamoxifen, tandutinib, tasonermin, teceleukin, tegafur, telatinib, temoporfin, temozolomide, temsirolimus, teniposide, testolactone, testosterone, tetrofosmin, thalidomide, thiotepa, thymalfasin, tioguanine, tipifarnib, tivozanib, toceranib, tocilizumab, topotecan, toremifene, tositumomab, trabectedin, trastuzumab, treosulfan, tretinoin, triapine, trilostane, trimetrexate, triptorelin, trofosfamide, ubenimex, valrubicin, vandetanib, vapreotide, varlitinib, vatalanib, vemurafenib, vidarabine, vinblastine, vincristine, vindesine, vinflunine, vinorelbine, volociximab, vorinostat, zinostatin, zoledronic acid, and zorubicin.

Generally, the following aims may be pursued with the combination of compounds of the present invention with other anti-cancer agents:
  improved activity in slowing down the growth of a tumor, in reducing its size or even in its complete elimination compared with treatment with a single active compound;
  possibility of employing the chemotherapeutics used in a lower dosage than in monotherapy;
  possibility of a more tolerable therapy with few side effects compared with individual administration;
  possibility of treatment of a broader spectrum of cancer and tumor diseases;
  achievement of a higher rate of response to therapy;
  longer survival time of the patient compared with standard therapy.

Thus, in a further embodiment, the present invention relates to pharmaceutical compositions comprising at least one of the compounds according to the invention and one or more additional therapeutic agents for the treatment and/or prevention of disorders, especially of the aforementioned disorders.

In cancer treatment, the compounds of the present invention may also be employed in conjunction with radiation therapy and/or surgical intervention.

Furthermore, the compounds of formula (I) may be utilized, as such or in compositions, in research and diagnostics, or as analytical reference standards, and the like, which are well known in the art.

When the compounds of the present invention are administered as pharmaceuticals, to humans and other mammals, they can be given per se or as a pharmaceutical composition containing, for example, 0.1% to 99.5% (more preferably, 0.5% to 90%) of active ingredient in combination with one or more pharmaceutically acceptable excipients.

Thus, in another aspect, the present invention relates to pharmaceutical compositions comprising at least one of the compounds according to the invention, conventionally together with one or more inert, non-toxic, pharmaceutically suitable excipients, and to the use thereof for the treatment and/or prevention of disorders, especially of the aforementioned disorders.

The compounds according to the invention can act systemically and/or locally. For this purpose, they can be administered in a suitable way such as, for example, by the oral, parenteral, pulmonary, nasal, lingual, sublingual, buccal, rectal, dermal, transdermal, conjunctival, otic or topical route, or as an implant or stent.

For these application routes, the compounds of the invention can be administered in suitable application forms.

Suitable for oral administration are application forms which function according to the prior art and deliver the compounds according to the invention rapidly and/or in modified fashion, and which contain the compounds according to the invention in crystalline, amorphous and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilisates, capsules (e.g. hard or soft gelatin capsules), sugar-coated tablets, granules, pellets, powders, emulsions, suspensions, aerosols or solutions.

Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Useful parenteral application forms include injection and infusion preparations in the form of solutions, suspensions, emulsions, lyophilisates and sterile powders.

Forms suitable for other application routes include, for example, inhalatory pharmaceutical forms (e.g. powder inhalers, nebulizers), nasal drops, solutions or sprays, tablets or capsules to be administered lingually, sublingually or buccally (e.g. troches, lozenges), suppositories, ear and eye preparations (e.g. drops, ointments), vaginal capsules, aqueous suspensions (lotions, shaking mixtures), lipophilic suspensions, ointments, creams, milks, pastes, foams, dusting powders, transdermal therapeutic systems (e.g. patches), implants and stents.

In a preferred embodiment, the pharmaceutical composition comprising a compound of formula (I) as defined above is provided in a form suitable for oral administration. In another preferred embodiment, the pharmaceutical composition comprising a compound of formula (I) as defined above is provided in a form suitable for intravenous administration.

The compounds according to the invention can be converted into the recited application forms in a manner known per se by mixing with inert, non-toxic, pharmaceutically suitable excipients. These excipients include, inter alia, carriers (e.g. microcrystalline cellulose, lactose, mannitol), solvents (e.g. liquid polyethylene glycols), emulsifiers (e.g. sodium dodecyl sulfate), surfactants (e.g. poly-oxysorbitan oleate), dispersants (e.g. polyvinylpyrrolidone), synthetic and natural polymers (e.g. albumin), stabilizers (e.g. antioxidants such as, for example, ascorbic acid), colorants (e.g. inorganic pigments such as, for example, iron oxides), and taste and/or odour masking agents.

A preferred dose of the compound of the present invention is the maximum that a patient can tolerate and not develop serious side effects. Illustratively, the compound of the present invention may be administered parenterally at a dose of about 0.001 mg/kg to about 1 mg/kg, preferably of about 0.01 mg/kg to about 0.5 mg/kg of body weight. On oral administration, an exemplary dose range is about 0.01 to 100 mg/kg, preferably about 0.01 to 20 mg/kg, and more preferably about 0.1 to 10 mg/kg of body weight. Ranges intermediate to the above-recited values are also intended to be part of the invention.

Nevertheless, actual dosage levels and time course of administration of the active ingredients in the pharmaceutical compositions of the invention may be varied so as to obtain an amount of the active ingredient which is effective to achieve the desired therapeutic response for a particular patient, composition and mode of administration, without being toxic to the patient. It may therefore be necessary where appropriate to deviate from the stated amounts, in particular as a function of age, gender, body weight, diet and general health status of the patient, the bioavailability and pharmacodynamic characteristics of the particular compound and its mode and route of administration, the time or interval over which administration takes place, the dose regimen selected, the response of the individual patient to the active ingredient, the specific disease involved, the degree of or the involvement or severity of the disease, the kind of concurrent treatment (i.e., the interaction of the compound of the invention with other co-administered therapeutics), and other relevant circumstances.

Thus, it may be satisfactory in some cases to manage with less than the aforementioned minimum amount, whereas in other cases the stated upper limit must be exceeded. Treatment can be initiated with smaller dosages, which are less than the optimum dose of the compound. Thereafter, the dosage may be increased by small increments until the optimum effect under the circumstances is reached. For convenience, the total daily dosage may be divided and administered in individual portions spread over the day.

The following exemplary embodiments illustrate the invention. The invention is not restricted to the examples.

The percentages in the following tests and examples are, unless stated otherwise, by weight; parts are by weight. Solvent ratios, dilution ratios and concentrations reported for liquid/liquid solutions are each based on volume.

A. EXAMPLES

Abbreviations and Acronyms

Ac acetyl
$Ac_2O$ acetic anhydride
AcOH acetic acid
aq. aqueous (solution)
Boc tert-butoxycarbonyl
br. broad ($^1$H-NMR signal)
cat. catalytic
conc. concentrated
d doublet ($^1$H-NMR signal)
DCI direct chemical ionization (MS)
DCM dichloromethane
Dess-Martin periodinane 1,1,1-triacetoxy-1,1-dihydro-1,2-benziodoxol-3(1H)-one
DIPEA N,N-diisopropylethylamine
DMF N,N-dimethylformamide
DMSO dimethylsulfoxide
EI electron impact ionization (MS)

eq. equivalent(s)
ESI electro-spray ionization (MS)
Et ethyl
EtOAc ethyl acetate
EtOH ethanol
GC-MS gas chromatography-coupled mass spectroscopy
h hour(s)
Hal halogen
$^1$H-NMR proton nuclear magnetic resonance spectroscopy
HPLC high performance liquid chromatography
iPr isopropyl
LC-MS liquid chromatography-coupled mass spectroscopy
Me methyl
MeOH methanol
min minute(s)
MS mass spectroscopy
m/z mass-to-charge ratio (MS)
n-Bu n-butyl
of th. of theory (chemical yield)
Pd/C palladium on charcoal
Ph phenyl
PPA polyphosphoric acid
q quartet ($^1$H-NMR signal)
quant. quantitative (yield)
rac racemic
$R_f$ TLC retention factor
RP reverse phase (HPLC)
rt room temperature
$R_t$ retention time (HPLC)
s singlet ($^1$H-NMR signal)
sat. saturated (solution)
t triplet ($^1$H-NMR signal)
TBTU N-[(1H-benzotriazol-1-yloxy)(dimethylamino)methylene]-N-methylmethanaminium tetrafluoroborate
tBu tert-butyl
tert tertiary
TFA trifluoroacetic acid
THF tetrahydrofuran
TLC thin layer chromatography
LC-MS and GC-MS Methods:
Method 1 (LC-MS):
Instrument: Micromass Quattro Premier with Waters UPLC Acquity; column: Thermo Hypersil GOLD 1.9μ, 50 mm×1 mm; eluent A: 1 L water+0.5 mL 50% aq. formic acid, eluent B: 1 L acetonitrile+0.5 ml 50% aq. formic acid; gradient: 0.0 min 90% A→0.1 min 90% A→1.5 min 10% A→2.2 min 10% A; temperature: 50° C.; flow rate: 0.33 mL/min; UV detection: 210 nm.
Method 2 (LC-MS):
Instrument: Waters Acquity SQD UPLC System; column: Waters Acquity UPLC HSS T3 1.8μ, 50 mm×1 mm; eluent A: 1 L water+0.25 mL 99% formic acid, eluent B: 1 L acetonitrile+0.25 mL 99% formic acid; gradient: 0.0 min 90% A→1.2 min 5% A→2.0 min 5% A; oven: 50° C.; flow rate: 0.40 mL/min; UV detection: 210-400 nm.
Method 3 (LC-MS):
Instrument: Micromass Quattro Micro with HPLC Agilent 1100 Series; column: YMC-Triart C18 3μ, 50 mm×3 mm; eluent A: 1 L water+0.01 mol ammonium carbonate, eluent B: 1 L acetonitrile; gradient: 0.0 min 100% A→2.75 min 5% A→4.5 min 5% A; oven: 40° C.; flow rate: 1.25 mL/min; UV detection: 210 nm.
Method 4 (LC-MS):
Instrument: Waters Acquity SQD UPLC System; column: Waters Acquity UPLC HSS T3 1.8μ, 30 mm×2 mm; eluent A: 1 L water+0.25 mL 99% formic acid, eluent B: 1 L acetonitrile+0.25 mL 99% formic acid; gradient: 0.0 min 90% A→1.2 min 5% A→2.0 min 5% A; oven: 50° C.; flow rate: 0.60 mL/min; UV detection: 208-400 nm.
Method 5 (LC-MS):
Instrument: Micromass Quattro Premier with Waters UPLC Acquity; column: Thermo Hypersil GOLD 1.9μ, 50 mm×1 mm; eluent A: 1 L water+0.5 mL 50% aq. formic acid, eluent B: 1 L acetonitrile+0.5 ml 50% aq. formic acid; gradient: 0.0 min 97% A→0.5 min 97% A→3.2 min 5% A→4.0 min 5% A; temperature: 50° C.; flow rate: 0.3 mL/min; UV detection: 210 nm.
Method 6 (GC-MS):
Instrument: Micromass GCT, GC6890; column: Restek RTX-35, 15 m×200 μm×0.33 μm; constant flow with helium: 0.88 mL/min; oven: 70° C.; inlet: 250° C.; gradient: 70° C., 30° C./min→310° C. (maintain for 3 min).
Method 7 (LC-MS):
Instrument MS: Waters SQD; Instrument HPLC: Waters UPLC; column: Zorbax SB-Aq (Agilent), 50 mm×2.1 mm, 1.8 μm; eluent A: water+0.025% formic acid, eluent B: acetonitrile+0.025% formic acid; gradient: 0.0 min 98% A→0.9 min 25% A→1.0 min 5% A→1.4 min 5% A→1.41 min 98% A→1.5 min 98% A; oven: 40° C.; flow rate: 0.60 mL/min; UV detection: DAD, 210 nm.
General Purification Methods (See Table I and II Below):
Purification Method 1 (PM1):
Instrument MS: Waters; Instrument HPLC: Waters; column: Waters X-Bridge C18, 18 mm×50 mm, 5 μm; eluent A: water+0.05% triethylamine, eluent B: acetonitrile or methanol+0.05% triethylamine; gradient elution; flow rate: 40 mL/min; UV detection: DAD, 210-400 nm.
Purification Method 2 (PM2):
Instrument MS: Waters; Instrument HPLC: Waters; column: Phenomenex Luna 5μ C18(2) 100A, AXIA Tech., 50 mm×21.2 mm; eluent A: water+0.05% formic acid, eluent B: acetonitrile or methanol+0.05% formic acid; gradient elution; flow rate: 40 mL/min; UV detection: DAD, 210-400 nm Starting Materials and Intermediates Intermediate 1A 2-Methoxy-4-methylaniline

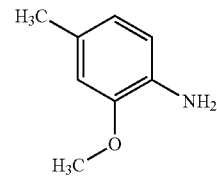

A mixture of 5-methyl-2-nitroanisol (265 g, 1.58 mol) and 10% Pd/C (39.75 g) in THF (1.32 L) was stirred overnight at rt under 1 atm of hydrogen. Filtration over kieselguhr and evaporation afforded 216.1 g of the crude product which was used in the next step without further purification.

LC-MS (method 3): $R_t$=2.39 min; MS (ESIpos): m/z=138 (M+H)$^+$ $^1$H-NMR (400 MHz, DMSO-d$_6$): δ=6.45-6.63 (m, 3H), 4.46 (s, 2H), 3.72 (s, 3H), 2.16 (s, 3H) ppm.

Intermediate 2A

2-Methoxy-4-methylbenzenethiol

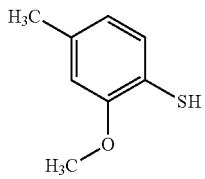

Method 1:

A solution of sodium nitrite (7 g, 101.4 mmol) in water (25 ml) was added dropwise to a cooled (0°-5° C.) solution of Intermediate 1A (13.7 g, 100 mmol) in concentrated hydrochloric acid (30 ml) and water (85 ml). After stirring at 0° C. for 10 min, sodium acetate (15 g, 182.8 mmol) was added. The resulting mixture was added dropwise to a hot solution (70°-80° C.) of potassium O-ethyl dithiocarbonate (30 g, 187.1 mmol) in water (140 ml), stirred between 70° C. and 80° C. for 1 h and then cooled to rt. The mixture was extracted twice with ethyl acetate, and the combined organic extracts were dried over sodium sulfate and evaporated. The residue was taken up in a 1.3 M solution of potassium hydroxide in ethanol (300 ml). Glucose (8 g) was added, and the resulting mixture was refluxed for 3 h. Then, the ethanol solvent was evaporated, and the residue was diluted with water and acidified with 6 N aqueous sulfuric acid. Zinc powder (15 g) was added carefully, and the resulting mixture was heated to 50° C. for 30 min. The mixture was then cooled to rt, diluted with dichloromethane and filtered. The filtrate was extracted twice with dichloromethane, and the combined organic extracts were dried over sodium sulfate and evaporated affording 14.3 g of the crude product which was used in the next step without further purification.

Method 2:

To 2.9 L of THF was added a warm solution of 355 ml (6.67 mol) concentrated sulfuric acid in 1.1 L of water. At 50° C., 293 g (1.33 mol) 2-methoxy-4-methylbenzenesulfonyl chloride were added under stirring. Then, 521 g (7.97 mol) of zinc powder were added carefully in portions (foaming), and the slightly exothermic reaction was cooled in a water bath to maintain a temperature of 50°-55° C. The mixture was subsequently stirred at 55° C. for 3 h. The progress of the reaction was monitored by TLC (silica gel, petrolether/ethyl acetate 95:5). The reaction mixture was poured into 13.6 L of water, 6.8 L dichloromethane were added, and the mixture was stirred for 5 min After decanting from remaining zinc and phase separation, the aqueous phase was extracted once more with 6.8 L dichloromethane. The combined organic phases were washed with 10% brine, dried and evaporated at 40° C. under reduced pressure yielding 237 g of crude product. This material was used in the next step without further purification. An analytical sample was obtained by silica gel chromatography with petrolether/ethyl acetate (97:3) as eluent.

LC-MS (method 1): $R_t$=1.21 min; MS (ESIneg): m/z=153 (M−H)−

$^1$H-NMR (400 MHz, DMSO-$d_6$): δ=7.17 (d, 1H), 6.81 (s, 1H), 6.66 (d, 1H), 4.63 (br. s, 1H), 3.80 (s, 3H), 2.26 (s, 3H) ppm.

Intermediate 3A

1-[(2,2-Diethoxyethyl)sulfanyl]-2-methoxy-4-methylbenzene

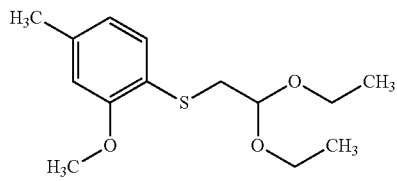 [SMILES: CCOC(CSc1ccc(C)cc1OC)OCC]

237 g crude material from Intermediate 2A, 287 g (1.46 mol) bromoacetaldehyde-diethylacetal and 862 g (2.65 mol) caesium carbonate were suspended in 2 L DMF. The reaction temperature increased initially to 40° C., then stirring was continued overnight at ambient temperature. The reaction mixture was partitioned between 10 L of water and 2.7 L of ethyl acetate. The aqueous phase was extracted with another portion of 2.7 L ethyl acetate. The combined organic phases were washed with 10% brine, dried and evaporated. The resulting oily residue was purified by silica gel chromatography with petrolether/ethyl acetate (95:5) as eluent.

Yield: 236 g of an oil (66% of th.)

GC-MS (method 6): $R_t$=6.03 min; MS (EIpos): m/z=270 (M)+

$^1$H-NMR (400 MHz, DMSO-$d_6$): δ=7.16 (d, 1H), 6.82 (s, 1H), 6.73 (d, 1H), 4.55 (t, 1H), 3.80 (s, 3H), 3.52-3.64 (m, 2H), 3.39-3.51 (m, 2H), 2.96 (d, 2H), 2.33 (s, 3H), 1.09 (t, 6H) ppm.

Intermediate 4A

7-Methoxy-5-methyl-1-benzothiophene

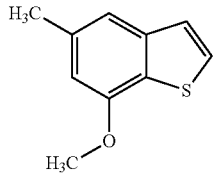

To a refluxing mixture of 13 g polyphosphoric acid and 150 ml chlorobenzene was added dropwise a solution of 5.2 g (19.2 mmol) of Intermediate 3A, and refluxing was continued overnight. After cooling, the organic layer was decanted, and the residue and flask were rinsed twice with DCM. The combined organic phases were evaporated at reduced pressure. The residue (3.76 g) was chromatographed on silica gel with isohexane/0-10% ethyl acetate as eluent.

Yield: 1.69 g of an oil (49% of th.)

GC-MS (method 6): $R_t$=5.20 min; MS (EIpos): m/z=178 (M)+

$^1$H-NMR (400 MHz, DMSO-$d_6$): δ=7.68 (d, 1H), 7.34 (d, 1H), 7.28 (s, 1H), 6.78 (s, 1H), 3.93 (s, 3H), 2.43 (s, 3H) ppm.

Intermediate 5A (7-Methoxy-5-methyl-1-benzothiophen-2-yl)boronic acid

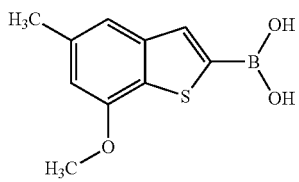

Under argon atmosphere, 26.7 g (150 mmol) of Intermediate 4A were dissolved in 270 ml of THF and cooled to −70° C. Between −70° C. and −65° C., 66 ml (165 mmol) of a 2.5 N solution of n-butyllithium in hexane were added dropwise within 20 min, resulting in formation of a white precipitate. After stirring for 1 h at −70° C., 41.5 ml (180 mmol) triisopropyl borate were added at this temperature within 10 min (resulting in a thick suspension). Stirring was continued for 1 h at −70° C., before the reaction mixture was allowed to warm up to rt overnight. Then, 400 ml of saturated aq. ammonium chloride solution were added, the layers were separated, and the aqueous layer was extracted once more with THF. The combined organic phases were evaporated under reduced pressure. To the residue thus obtained, 200 ml of water and 86 ml of 2 N aq. sodium hydroxide solution were added. The solution was washed twice with DCM, then acidified with 35 ml of 3 M sulfuric acid, and the resulting suspension was stirred vigorously for 1 h. The precipitate was filtered off by suction and dried overnight at 45° C. in vacuo.

Yield: 28.25 g of a colorless solid (94% pure by LC-MS, 80% of th.)

LC-MS (method 2): $R_t$=0.87 min; MS (ESIpos): m/z=223 (M+H)$^+$ $^1$H-NMR (400 MHz, DMSO-d$_6$): δ=7.17 (d, 1H), 6.81 (s, 1H), 6.66 (d, 1H), 4.63 (br. s, 1H), 3.80 (s, 3H), 2.26 (s, 3H) ppm.

Intermediate 6A 2-(7-Methoxy-5-methyl-1-benzothiophen-2-yl)-6-methyl-1,3,6,2-dioxazaborocane-4,8-dione

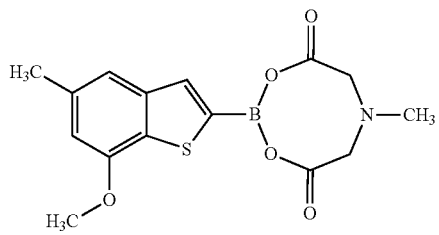

6.3 g (28.4 mmol) of Intermediate 5A and 4.2 g (28.4 mmol) 2,2'-(methylimino)diacetic acid were dissolved in a mixture of 45 ml DMSO and 400 ml toluene and refluxed for 16 h using a Dean-Stark trap. After evaporation, the residue was taken up in ethyl acetate and washed three times with water and once with brine. The organic phase was dried over magnesium sulfate and evaporated to a volume of about 200 ml. A white solid precipitated which was filtered, washed with ethyl acetate and dried in vacuo to give a first crop (5.52 g) of the title compound. A second crop (3.32 g) was obtained after evaporation of the mother liquor and flash-chromatography over a layer of silica gel using cyclohexane/0-100% ethyl acetate as the eluent.

Yield: 8.84 g (overall purity 92.5% by LC-MS, 87% of th.)

LC-MS (method 2): $R_t$=0.93 min; MS (ESIpos): m/z=334 (M+H)$^+$ $^1$H-NMR (400 MHz, DMSO-d$_6$): δ=7.42 (s, 1H), 7.26 (s, 1H), 6.76 (s, 1H), 4.40 (d, 2H), 4.17 (d, 2H), 3.92 (s, 3H), 2.63 (s, 3H), 2.42 (s, 3H) ppm.

Intermediate 7A

Ethyl 4-aminopyrrolo[2,1-f][1,2,4]triazine-6-carboxylate

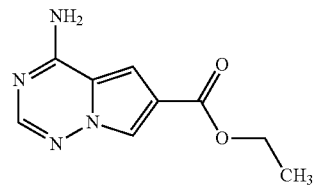

A solution of 4-aminopyrrolo[2,1-f][1,2,4]triazine-6-carbonitrile (3.9 g, 24.5 mmol; preparation described in Int. Pat. Appl. WO 2007/064883) in ethanol (124.8 ml) was stirred with concentrated sulfuric acid (62.4 ml) at 80° C. overnight. After cooling to rt, the reaction mixture was poured onto 800 g of ice and brought to pH 6-7 with concentrated aq. sodium hydroxide solution. Ethyl acetate (500 ml) and dichloromethane (500 ml) were added to the suspension, and the resulting mixture was filtered over kieselguhr. The organic layer was separated from the aqueous layer. The solid was dissolved in hot water (1 L), and the aqueous layer was extracted twice with ethyl acetate. The combined organic layers were dried over sodium sulfate and evaporated. The residue was triturated with an isopropanol/diethylether mixture, and the solid was filtered off yielding 2.5 g (49% of th.) of the title compound.

LC-MS (method 2): $R_t$=0.59 min; MS (ESIpos): m/z=206 (M+H)$^+$ $^1$H-NMR (400 MHz, DMSO-d$_6$): δ=8.11-7.97 (m, 3H), 7.88 (s, 1H), 7.34 (br. s, 1H), 4.27 (q, 2H), 1.30 (t, 3H) ppm.

Intermediate 8A (4-Aminopyrrolo[2,1-f][1,2,4]triazin-6-yl)methanol

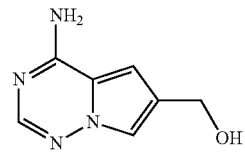 [SMILES: Nc1ncnn2cc(CO)cc12]

An ice-cooled solution of Intermediate 7A (3.0 g, 14.5 mmol) in THF (30 ml) was treated with a 1 M solution of lithium triethylborohydride in THF (58 ml) and stirred at rt for 45 min. The reaction mixture was then cooled to 0° C., quenched with methanol, warmed slowly to rt and adsorbed on kieselguhr. Purification by column chromatography over silica gel (dichloromethane/methanol 20:1→4:1 gradient) afforded 2.21 g (92.5% of th.) of the title compound.

LC-MS (method 3): $R_t$=1.46 min; MS (ESIpos): m/z=164 (M+H)$^+$ $^1$H-NMR (400 MHz, DMSO-d$_6$): δ=7.75 (s, 1H), 7.64 (br. s, 2H), 7.50 (br. d, 1H), 6.79 (br. d, 1H), 5.01 (t, 1H), 4.50 (d, 2H) ppm.

Intermediate 9A (4-Amino-5,7-dibromopyrrolo[2,1-f][1,2,4]triazin-6-yl)methanol

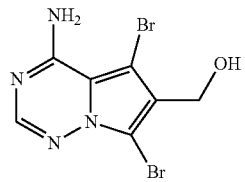 [SMILES: Nc1ncnn2c(Br)c(CO)c(Br)c12]

A solution of Intermediate 8A (5 g, 30.4 mmol) in THF (100 ml) was treated with 1,3-dibromo-5,5-dimethylhydantoin (9.58 g, 33.5 mmol) and stirred at rt for 2 h. Filtration of the precipitate afforded 6.6 g (64% of th.) of the title compound.

LC-MS (method 2): $R_t$=0.56 min; MS (ESIpos): m/z=321/323/325 (M+H)$^+$ $^1$H-NMR (400 MHz, DMSO-d$_6$): δ=8.23 (br. s, 1H), 7.96 (s, 1H), 6.94 (br. s, 1H), 5.09 (br. s, 1H), 4.43 (s, 2H) ppm.

Intermediate 10A (4-Amino-5-bromopyrrolo[2,1-f][1,2,4]triazin-6-yl)methanol

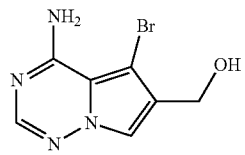 [SMILES: Nc1ncnn2cc(CO)c(Br)c12]

A suspension of Intermediate 9A (3.7 g, 11.5 mmol) in THF (800 ml) was heated under stirring until complete dissolution. The mixture was then cooled to −78° C., and a 1.6 M solution of n-butyllithium in hexanes (20 ml, 32.1 mmol) was added dropwise. After 5 min, a further portion of 1.6 M n-butyllithium solution (1.5 ml, 2.29 mmol) was added. The resulting mixture was stirred at −78° C. for 5 min, then quenched with methanol (5 ml) and warmed to rt. The reaction mixture was diluted with sat. aq. ammonium chloride solution, sat. aq. sodium hydrogencarbonate solution, sat. aq. sodium chloride solution and ethyl acetate. After phase separation, the organic layer was washed with sat. aq. sodium chloride solution. The combined aqueous layers were re-extracted with ethyl acetate. The combined organic layers were washed again with sat. aq. sodium chloride solution, dried over magnesium sulfate and evaporated to afford 2.87 g of the crude product which was used in subsequent steps without further purification.

LC-MS (method 3): $R_t$=1.73 min; MS (ESIpos): m/z=243/245 (M+H)$^+$ $^1$H-NMR (400 MHz, DMSO-d$_6$): δ=8.41-7.89 (br. s, 1H), 7.82 (s, 1H), 7.66 (s, 1H), 7.13-6.48 (br. s, 1H), 5.11 (t, 1H), 4.45 (d, 2H) ppm.

Intermediate 11A 6-(Chloromethyl)-5-(7-methoxy-5-methyl-1-benzothiophen-2-yl)pyrrolo[2,14][1,2,4]triazin-4-amine hydrochloride

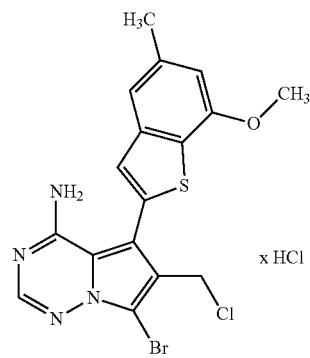 [SMILES: COc1cc(C)cc2cc(-c3c(CCl)c(Br)n4ncnc(N)c34)sc12]

A suspension of Example 32 (300 mg, purity 90%, 793 μmol) in dichloromethane (9 ml) was treated with thionyl chloride (116 μl, 1.59 mmol) and stirred at rt for 40 min. Then, the volatiles were evaporated under reduced pressure yielding 382 mg of the crude title compound which was used in subsequent steps without further purification.

LC-MS (method 2): $R_t$=1.15 min; MS (ESIpos): m/z=359/361 (M+H)$^+$ $^1$H-NMR (400 MHz, DMSO-d$_6$): δ=8.84-9.09 (br. s, 1H), 8.18 (s, 1H), 8.15 (s, 1H), 7.46 (s, 1H), 7.35 (s, 1H), 6.95-7.21 (br. s, 1H), 6.88 (s, 1H), 4.78 (s, 2H), 3.97 (s, 3H), 2.46 (s, 3H) ppm.

Intermediate 12A 6-(Azidomethyl)-5-(7-methoxy-5-methyl-1-benzothiophen-2-yl)pyrrolo[2,1-f][1,2,4]triazin-4-amine

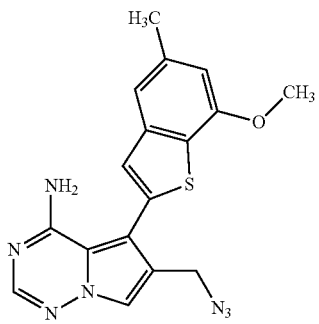 [SMILES: COc1cc(C)cc2cc(-c3c(CN=[N+]=[N-])cn4ncnc(N)c34)sc12]

A suspension of Example 32 (300 mg, 773 μmol) in dichloromethane (8.7 ml) was treated with thionyl chloride (84 μl, 1.16 mmol) and stirred at rt for 30 min After evaporation, the residue was dissolved in DMF (8.7 ml) and treated with sodium azide (1.00 g, 15.4 mmol) and sodium iodide (580 mg, 3.8 mmol). The mixture was stirred at 80° C. for 3 h. After dilution with ethyl acetate, the mixture was washed with water and sat. aq. sodium chloride solution, dried over magnesium sulfate and evaporated. Purification by column chromatography over silica gel (cyclohexane/25-100% ethyl acetate gradient) afforded 232 mg (82% of th.) of the title compound.

LC-MS (method 4): $R_t$=1.12 min; MS (ESIpos): m/z=366 (M+H)$^+$ $^1$H-NMR (400 MHz, DMSO-d$_6$): δ=7.97-7.95 (m, 2H), 7.38 (s, 1H), 7.32 (s, 1H), 6.86 (s, 1H), 4.42 (s, 2H), 3.96 (s, 3H), 2.45 (s, 3H) ppm.

Intermediate 13A

4-Amino-5-(7-methoxy-5-methyl-1-benzothiophen-2-yl)pyrrolo[2,1-f][1,2,4]triazine-6-carbaldehyde

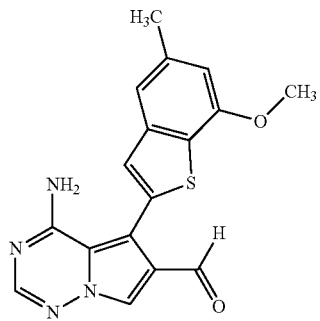 [SMILES: COc1cc(C)cc2cc(-c3c(C=O)cn4ncnc(N)c34)sc12]

A solution of Example 32 (350 mg, 902 μmol) in dichloromethane (19 ml) was treated with Dess-Martin periodinane (1,1,1-triacetoxy-1,1-dihydro-1,2-benziodoxol-3(1H)-one; 497 mg, 1.17 mmol) in portions. The reaction mixture was stirred at rt for 10 min and then quenched with a 1:1 mixture of sat. aq. sodium hydrogencarbonate solution and sat. aq. sodium thiosulfate solution. The resulting mixture was stirred for 30 min After phase separation, the aqueous layer was extracted three times with dichloromethane. The combined organic phases were dried over magnesium sulfate and evaporated. Purification by column chromatography over silica gel (cyclohexane/0-50% ethyl acetate gradient) afforded 205 mg (65% of th.) of the title compound.

LC-MS (method 5): $R_t$=2.16 min; MS (ESIpos): m/z=339 (M+H)$^+$ $^1$H-NMR (400 MHz, DMSO-d$_6$): δ=9.89 (s, 1H), 8.42-8.22 (br. s, 1H), 8.36 (s, 1H), 8.04 (s, 1H), 7.52 (s, 1H), 7.33 (s, 1H), 6.88 (s, 1H), 6.17-5.85 (br. s, 1H), 3.96 (s, 3H), 2.46 (s, 3H) ppm.

Intermediate 14A

4-Amino-5-bromopyrrolo[2,1-f][1,2,4]triazine-6-carbaldehyde

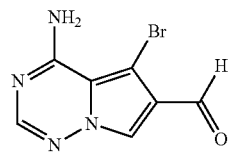 [SMILES: Nc1ncnn2cc(C=O)c(Br)c12]

A solution of Intermediate 10A (1 g, 4.11 mmol) in dichloromethane (20 ml) was treated with Dess-Martin periodinane (1,1,1-triacetoxy-1,1-dihydro-1,2-benziodoxol-3 (1H)-one; 2.26 g, 5.34 mmol) in portions. The reaction mixture was stirred at rt for 20 min and then quenched with a 1:1 mixture of sat. aq. sodium hydrogencarbonate solution and sat. aq. sodium thiosulfate solution. The resulting mixture was stirred at rt for 45 min. The precipitate was filtered off, and the aqueous phase was extracted three times with dichloromethane. The combined organic phases were dried over magnesium sulfate and evaporated. Purification by column chromatography over silica gel (cyclohexane/0-100% ethyl acetate gradient) afforded 480 mg (40% of th.) of the title compound.

LC-MS (method 2): $R_t$=0.55 min; MS (ESIpos): m/z=241/243 (M+H)$^+$ $^1$H-NMR (400 MHz, DMSO-d$_6$): δ=9.93 (s, 1H), 8.64-8.42 (br. s, 1H), 8.37 (s, 1H), 7.95 (s, 1H), 7.34-7.03 (br. s, 1H) ppm.

Intermediate 15A

4-[(4-Amino-5-bromopyrrolo[2,1-f][1,2,4]triazin-6-yl)methyl]piperazin-2-one

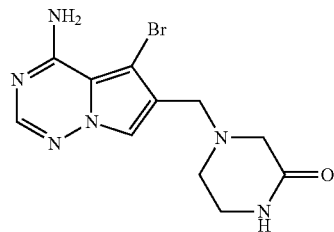 [SMILES: Nc1ncnn2cc(CN3CCNC(=O)C3)c(Br)c12]

A solution of Intermediate 14A (478 mg, 1.98 mmol) in THF (26 ml) was treated with 2-oxopiperazine (992 mg, 9.91 mmol), sodium triacetoxyborohydride (2.10 g, 9.91 mmol) and acetic acid (227 μl, 3.96 mmol). The reaction mixture was stirred at rt for 2 h. The mixture was then combined with the reaction mixture from a 65 mg test run, quenched with methanol and adsorbed on kieselguhr. Purification by column chromatography over silica gel (dichloromethane/methanol 100:9) afforded 525 mg (70% of th.) of the title compound.

LC-MS (method 3): $R_t$=1.81 min; MS (ESIpos): m/z=325/327 (M+H)$^+$ $^1$H-NMR (500 MHz, CDCl$_3$): δ=7.85 (s, 1H), 7.56 (s, 1H), 5.91 (br. s, 1H), 3.64 (s, 2H), 3.39-3.34 (m, 2H), 3.23 (s, 2H), 2.71 (t, 2H) ppm.

Intermediate 16A 2-(5-Chloro-7-methoxy-1-benzothiophen-2-yl)-6-methyl-1,3,6,2-dioxazaborocane-4,8-dione

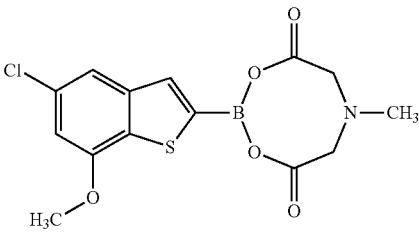 [SMILES: COc1cc(Cl)cc2cc(B3OC(=O)CN(C)CC(=O)O3)sc12]

The title compound was prepared from 4-chloro-2-methoxybenzenethiol [J. O. Jilek et al., *Collection of Czechoslovak Chemical Communications*, Vol. 43, 1978, p. 1747-1759] following the procedures described for Intermediates 3A, 4A, 5A and 6A.

LC-MS (method 2): $R_t$=0.96 min; MS (ESIpos): m/z=354 $(M+H)^+$ $^1$H-NMR (400 MHz, DMSO-$d_6$): δ=7.58 (d, 1H), 7.51 (s, 1H), 6.98 (d, 1H), 4.42 (d, 2H), 4.19 (d, 2H), 3.97 (s, 3H), 2.65 (s, 3H) ppm.

Intermediate 17A 5,7-Dimethoxy-1-benzothiophene

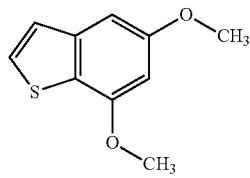

To a solution of 1-benzothiophene-5,7-diol (1.16 g, 6.98 mmol) in acetone (20 ml) under argon were added potassium carbonate (2.89 g, 20.9 mmol) and iodomethane (912 µl, 14.6 mmol). The resulting mixture was stirred under reflux for 18 h. After cooling to rt, the mixture was treated with a 7 M solution of ammonia in methanol (10 ml) for 30 min and then adsorbed on silica gel. Purification by column chromatography over silica gel (cyclohexane/ethyl acetate 40:1) afforded 0.52 g (32% of th.) of the title compound.

LC-MS (method 4): $R_t$=1.02 min; MS (ESIpos): m/z=195 $(M+H)^+$ $^1$H-NMR (400 MHz, DMSO-$d_6$): δ=7.69 (d, 1H), 7.35 (d, 1H), 7.02 (d, 1H), 6.57 (d, 1H), 3.92 (s, 3H), 3.81 (s, 3H) ppm.

Intermediate 18A (5,7-Dimethoxy-1-benzothiophen-2-yl)boronic acid

Under an argon atmosphere, a 1.6 M solution of n-butyllithium in hexane (1.84 ml, 2.95 mmol) was added dropwise to a solution of Intermediate 17A (520 mg, 2.68 mmol) in dry THF (5 ml) at −70° C. After 1 h at −70° C., triisopropyl borate (742 µl, 3.21 mmol) was added, and the mixture was stirred for 16 h while slowly warming up to rt. Dichloromethane and sat. aq ammonium chloride solution were added, and the pH value was adjusted to 6 by addition of 1 M hydrochloric acid. The organic phase was separated, and the aqueous phase was extracted with dichloromethane. The combined organic phases were dried with magnesium sulfate, filtered and evaporated. The resulting residue was purified by column chromatography over silica gel (at first eluting with dichloromethane/methanol 40:1, then methanol, finally methanol/4 M hydrogen chloride in 1,4-dioxane 10:1) yielding 631 mg (71% purity, 71% of th.) of the title compound.

LC-MS (method 4): $R_t$=0.83 min; MS (ESIpos): m/z=239 $(M+H)^+$.

Intermediate 19A 6-(Bromomethyl)-5-(7-methoxy-5-methyl-1-benzothiophen-2-yl)pyrrolo[2,1-f][1,2,4]triazin-4-amine hydrobromide

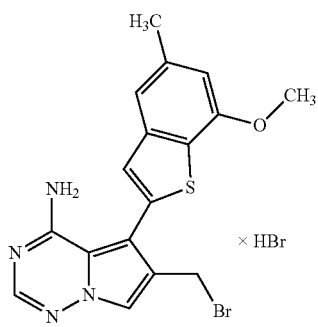 [SMILES: COc1cc(C)cc2cc(-c3c(CBr)cn4ncnc(N)c34)sc12]

A solution of Example 28 (4 g, 10.9 mmol) in dichloromethane (80 ml) was treated with a 33% solution of hydrogen bromide in acetic acid (5.62 ml, 32.6 mmol) and stirred at rt for 22 h. The volatiles were evaporated under reduced pressure yielding 5.81 g of the crude title compound which was used in subsequent steps without further purification.

$^1$H-NMR (400 MHz, DMSO-$d_6$): δ=8.68-8.94 (br. s, 1H), 8.19 (s, 1H), 8.11 (s, 1H), 7.48 (s, 1H), 7.35 (s, 1H), 6.89 (s, 1H), 6.79-7.07 (br. s, 1H), 4.71 (s, 2H), 3.97 (s, 3H), 2.46 (s, 3H) ppm.

Preparation Examples

Example 1

3-{[4-Amino-5-(7-methoxy-5-methyl-1-benzothiophen-2-yl)pyrrolo[2,1-f][1,2,4]triazin-6-yl]-methoxy}propan-1-ol hydrochloride

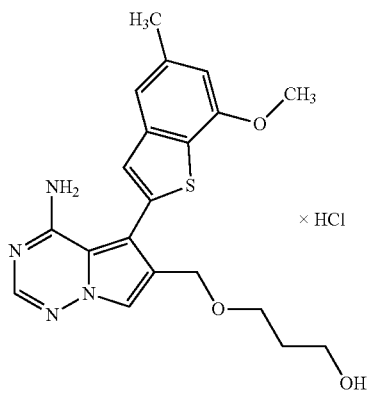 [SMILES: COc1cc(C)cc2cc(-c3c(COCCCO)cn4ncnc(N)c34)sc12]

A solution of Intermediate 11A (100 mg, 253 μmol), propane-1,3-diol (577 mg, 7.59 mmol) and DIPEA (209 μl, 1.27 mmol) in THF (2 ml) was heated to 150° C. for 15 min in a microwave reactor. Then, the reaction mixture was cooled to rt, diluted with water and extracted twice with a mixture of ethyl acetate and THF. The combined organic phases were washed with sat. aq. sodium hydrogencarbonate solution and sat. aq. sodium chloride solution, dried over magnesium sulfate and evaporated. The residue was purified by preparative RP-HPLC (Reprosil C18, gradient 50-70% acetonitrile/0.2% aq. TFA). The combined product fractions were treated with 1 M hydrochloric acid (2 ml) and finally evaporated to dryness yielding 21 mg (17% of th.) of the title compound.

LC-MS (method 4): $R_t$=0.88 min; MS (ESIpos): m/z=399 (M+H)$^+$ $^1$H-NMR (400 MHz, DMSO-d$_6$): δ=8.58-8.86 (m, 1H), 8.09 (s, 1H), 8.00 (s, 1H), 7.40 (s, 1H), 7.32 (s, 1H), 6.86 (s, 1H), 4.41 (s, 2H), 3.96 (s, 3H), 3.43 (q, 4H), 2.45 (s, 3H), 1.63 (quin, 2H) ppm.

Example 2

(2S)-1-{[4-Amino-5-(7-methoxy-5-methyl-1-benzo-thiophen-2-yl)pyrrolo[2,1-f][1,2,4]triazin-6-yl]-methoxy}propan-2-ol

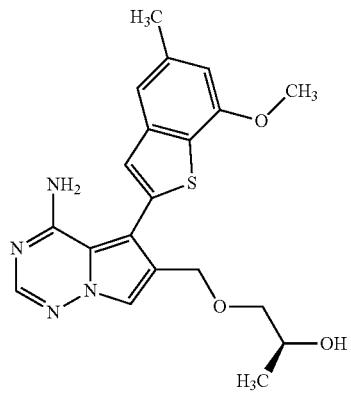 [SMILES: COc1cc(C)cc2cc(-c3c(COC[C@H](C)O)cn4ncnc(N)c34)sc12]

A solution of Intermediate 11A (80 mg, 202 μmol), (2S)-propane-1,2-diol (508 mg, 6.68 mmol) and DIPEA (100 μl, 607 μmol) in THF (1.8 ml) was heated to 150° C. for 15 min in a microwave reactor. Then, the reaction mixture was cooled to rt, diluted with water and extracted twice with a mixture of ethyl acetate and THF. The combined organic phases were washed with sat. aq. sodium hydrogencarbonate solution and sat. aq. sodium chloride solution, dried over magnesium sulfate and evaporated. The residue was purified by preparative HPLC (Daicel Chiralpak AZ-H, isohexane/ethanol 1:1) yielding 13 mg (16% of th.) of the title compound.

LC-MS (method 2): $R_t$=0.95 min; MS (ESIpos): m/z=399 (M+H)$^+$ $^1$H-NMR (400 MHz, DMSO-d$_6$): δ=7.93 (s, 1H), 7.84 (s, 1H), 7.60-8.00 (br. s, 1H), 7.38 (s, 1H), 7.30 (s, 1H), 6.84 (s, 1H), 5.57-6.11 (br. s, 1H), 4.53 (d, 1H), 4.46 (s, 2H), 3.96 (s, 3H), 3.64-3.75 (m, 1H), 3.24-3.30 (m, 1H), 3.15-3.21 (m, 1H), 2.45 (s, 3H), 0.99 (d, 3H) ppm.

Example 3

(2S)-2-{[4-Amino-5-(7-methoxy-5-methyl-1-benzo-thiophen-2-yl)pyrrolo[2,1-f][1,2,4]triazin-6-yl]-methoxy}propan-1-ol

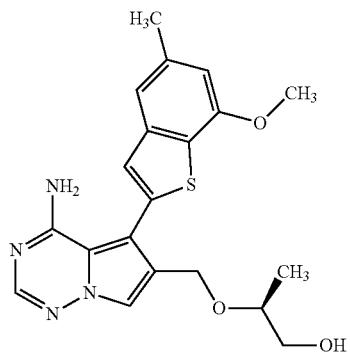 [SMILES: COc1cc(C)cc2cc(-c3c(CO[C@@H](C)CO)cn4ncnc(N)c34)sc12]

A solution of Intermediate 11A (80 mg, 202 μmol), (2S)-propane-1,2-diol (508 mg, 6.68 mmol) and DIPEA (100 μl, 607 μmol) in THF (1.8 ml) was heated to 150° C. for 15 min in a microwave reactor. Then, the reaction mixture was cooled to rt, diluted with water and extracted twice with a mixture of ethyl acetate and THF. The combined organic phases were washed with sat. aq. sodium hydrogencarbonate solution and sat. aq. sodium chloride solution, dried over magnesium sulfate and evaporated. The residue was purified by preparative HPLC (Daicel Chiralpak AZ-H, isohexane/ethanol 1:1) yielding 11 mg (13% of th.) of the title compound.

LC-MS (method 2): $R_t$=0.93 min; MS (ESIpos): m/z=399 (M+H)$^+$ $^1$H-NMR (400 MHz, DMSO-d$_6$): δ=7.92 (s, 1H), 7.82 (s, 1H), 7.54-8.11 (br. s, 1H), 7.39 (s, 1H), 7.30 (s, 1H), 6.84 (s, 1H), 5.49-6.21 (br. s, 1H), 4.45-4.57 (m, 3H), 3.96 (s, 3H), 3.40-3.49 (m, 1H), 3.33-3.40 (m, 1H), 3.22-3.30 (m, 1H), 2.45 (s, 3H), 0.99 (d, 3H) ppm.

Example 4

Ethyl {[4-amino-5-(7-methoxy-5-methyl-1-benzoth-iophen-2-yl)pyrrolo[2,1-f][1,2,4]triazin-6-yl]-methoxy}acetate

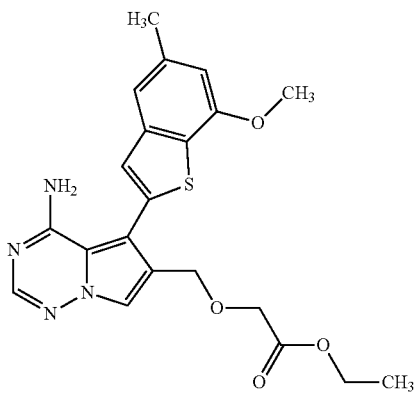 [SMILES: CCOC(=O)COCc1cn2ncnc(N)c2c1-c1cc2cc(C)cc(OC)c2s1]

A mixture of Intermediate 11A (500 mg, 1.27 mmol), ethyl glycolate (11.9 ml, 126 mmol) and DIPEA (1.05 ml, 6.32 mmol) was heated to 70° C. for 9 h. Then, the reaction mixture was cooled to rt, poured onto a silica gel column and eluted with a gradient of 0-100% ethyl acetate/cyclohexane. The product fractions were combined and evaporated under reduced pressure, and the residue was re-purified by preparative RP-HPLC (Reprosil C18, gradient 20-40% acetonitrile/0.2% aq. TFA). The product fractions were again combined and evaporated to dryness, and the residue was dissolved in methanol and filtered through an anion exchange cartridge (StratoSpheres SPE, PL-HCO$_3$ MP-resin). The cartridge was eluted with methanol, and the filtrate was evaporated yielding 23 mg (4% of th.) of the title compound.

LC-MS (method 2): $R_t$=1.06 min; MS (ESIpos): m/z=427 (M+H)$^+$ $^1$H-NMR (400 MHz, DMSO-d$_6$): δ=7.93 (s, 1H), 7.84 (s, 1H), 7.79-8.13 (br. s, 3H), 7.38 (s, 1H), 7.30 (s, 1H), 6.84 (s, 1H), 5.64-6.02 (br. s, 1H), 4.55 (s, 2H), 4.07 (s, 2H), 4.02 (q, 2H), 3.95 (s, 3H), 2.45 (s, 3H), 1.12 (t, 3H) ppm.

Example 5

{[4-Amino-5-(7-methoxy-5-methyl-1-benzothiophen-2-yl)pyrrolo[2,1-f][1,2,4]triazin-6-yl]methoxy}acetic acid

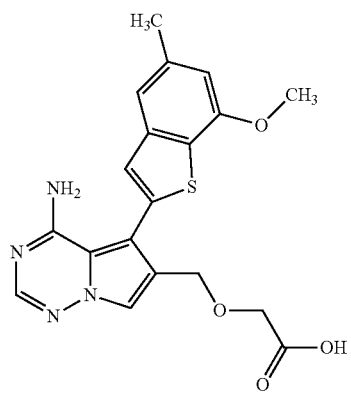 [SMILES: COc1cc(C)cc2cc(-c3c(COCC(=O)O)cn4ncnc(N)c34)sc12]

The compound from Example 4 (50 mg, purity 75%, 88 μmol) was stirred in a mixture of THF (3 ml) and 1 M aq. lithium hydroxide solution (3 ml) for 30 min at rt. Then, the mixture was acidified with 1 M aq. TFA to pH 2-3 and concentrated under reduced pressure to a volume of about 2 ml. Acetonitrile was added, and the solution was separated by preparative RP-HPLC (Reprosil C18, gradient 30-50% acetonitrile/0.2% aq. TFA). The product fractions were combined and evaporated to dryness yielding 9 mg (26% of th.) of the title compound.

LC-MS (method 2): $R_t$=0.86 min; MS (ESIpos): m/z=399 (M+H)$^+$ $^1$H-NMR (400 MHz, DMSO-d$_6$): δ=8.04-8.44 (br. s, 1H), 7.99 (s, 1H), 7.90 (s, 1H), 7.41 (s, 1H), 7.31 (s, 1H), 6.85 (s, 1H), 6.03-6.44 (br. s, 1H), 4.54 (s, 2H), 4.01 (s, 2H), 3.95 (s, 3H), 2.45 (s, 3H) ppm.

Example 6

2-{[4-Amino-5-(7-methoxy-5-methyl-1-benzothiophen-2-yl)pyrrolo[2,1-f][1,2,4]triazin-6-yl]methoxy}acetamide

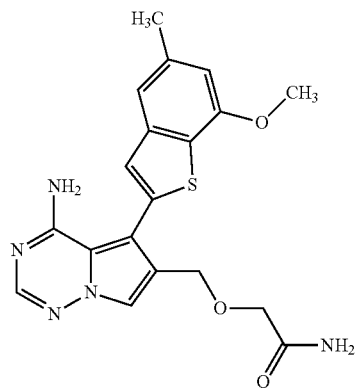 [SMILES: COc1cc(C)cc2cc(-c3c(COCC(N)=O)cn4ncnc(N)c34)sc12]

The compound from Example 4 (38 mg, 88 μmol) was dissolved in a 7 M solution of ammonia in methanol (6 ml) and heated to 135° C. for 60 min in a microwave reactor. The volatiles were then removed under reduced pressure, and the residue was purified by preparative RP-HPLC (Reprosil C18, gradient 30-50% acetonitrile/0.2% aq. TFA). The product fractions were combined and evaporated to dryness, and the residue was dissolved in methanol and filtered through an anion exchange cartridge (StratoSpheres SPE, PL-HCO$_3$ MP-resin). The cartridge was eluted with methanol, and the filtrate was evaporated. The residue was suspended in 1,4-dioxane and finally lyophilized yielding 25 mg (72% of th.) of the title compound.

LC-MS (method 2): $R_t$=0.83 min; MS (ESIpos): m/z=398 (M+H)$^+$ $^1$H-NMR (400 MHz, DMSO-d$_6$): δ=7.96 (s, 1H), 7.93 (s, 1H), 7.71-8.15 (br. s, 2H), 7.38 (s, 1H), 7.31 (s, 1H), 7.25 (br. s, 1H), 7.16 (br. s, 1H), 6.84 (s, 1H), 5.58-6.06 (br. s, 1H), 4.53 (s, 2H), 3.95 (s, 3H), 3.79 (s, 2H), 2.45 (s, 3H) ppm.

Example 7

2-{[4-Amino-5-(7-methoxy-5-methyl-1-benzothiophen-2-yl)pyrrolo[2,1-f][1,2,4]triazin-6-yl]methoxy}ethanol hydrochloride

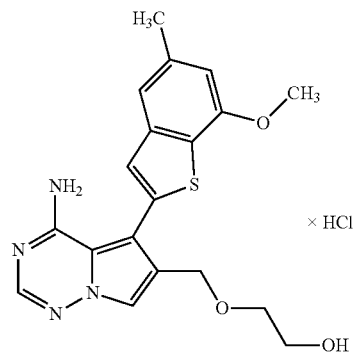 [SMILES: COc1cc(C)cc2cc(-c3c(COCCO)cn4ncnc(N)c34)sc12]

A solution of Example 32 (110 mg, 323 μmol) was treated with thionyl chloride (47 μl, 646 μmol) under stirring. The mixture was stirred at rt for further 20 min and then evaporated. The residue was dissolved in ethylene glycol/THF (1:1, 2 ml), treated with DIPEA (281 μl, 1.6 mmol) and stirred at 100° C. for 3 h. After evaporation, the residue was dissolved in ethyl acetate, and the solution was washed with sat. aq. sodium hydrogencarbonate solution and sat. aq. sodium chloride solution, dried over magnesium sulfate and evaporated. Purification by column chromatography over silica gel (ethyl acetate with 0.1% aq. ammonia) and lyophilization from a 4 N solution of hydrogen chloride in 1,4-dioxane afforded 81 mg (50% of th.) of the title compound.

LC-MS (method 2): $R_t$=0.88 min; MS (ESIpos): m/z=385 $(M+H)^+$ $^1$H-NMR (400 MHz, DMSO-$d_6$): δ=9.05-8.61 (br. s, 1H), 8.12 (s, 1H), 8.05 (s, 1H), 7.45 (s, 1H), 7.32 (s, 1H), 7.25-6.81 (br. s, 1H), 6.86 (s, 1H), 4.46 (s, 2H), 3.96 (s, 3H), 3.52-3.45 (m, 2H), 3.44-3.37 (m, 2H), 2.46 (s, 3H) ppm.

Example 8

6-[(2-Aminoethoxy)methyl]-5-(7-methoxy-5-methyl-1-benzothiophen-2-yl)pyrrolo[2,14][1,2,4]-triazin-4-amine dihydrochloride

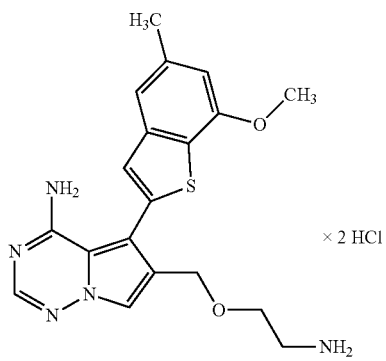 [SMILES: COc1cc(C)cc2cc(-c3c(COCCN)cn4ncnc(N)c34)sc12]

A solution of Example 32 (50 mg, 146 μmol) in dichloromethane (3 ml) was treated with thionyl chloride (21 μl, 293 μmol). The mixture was stirred at rt overnight and then evaporated. The residue was mixed with tert-butyl(2-hydroxyethyl)carbamate (2 ml) and DIPEA (213 μl, 734 μmol), and the solution was stirred for 2 h at 80° C., followed by 6 h at 100° C. After evaporation, the residue was dissolved in a 4 N solution of hydrogen chloride in 1,4-dioxane (2 ml) and stirred at rt for 2 h. The mixture was evaporated again, and the residue was purified by preparative RP-HPLC (Reprosil C18, gradient 10-95% acetonitrile/0.1% aq. formic acid). The product fractions were combined and evaporated, and the residue was lyophilized from a 4 N solution of hydrogen chloride in 1,4-dioxane affording 33 mg (43% of th.) of the title compound.

LC-MS (method 2): $R_t$=0.66 min; MS (ESIpos): m/z=384 $(M+H)^+$ $^1$H-NMR (400 MHz, DMSO-$d_6$): δ=9.00-8.44 (br. s, 1H), 8.11 (s, 2H), 7.97 (br. s, 2H), 7.41 (s, 1H), 7.33 (s, 1H), 6.96-6.50 (br. s, 1H), 6.87 (s, 1H), 4.54 (s, 2H), 3.96 (s, 3H), 3.61-3.55 (m, 2H, overlap with water peak), 3.01-2.93 (m, 2H), 2.46 (s, 3H) ppm.

Example 9

N-{[4-Amino-5-(7-methoxy-5-methyl-1-benzothiophen-2-yl)pyrrolo[2,1-f][1,2,4]triazin-6-yl]-methyl}acetamide

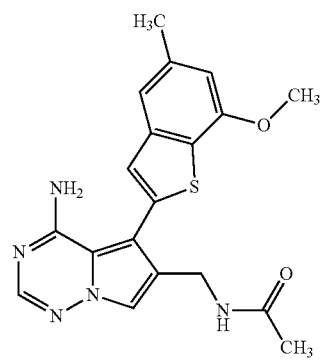 [SMILES: COc1cc(C)cc2cc(-c3c(CNC(C)=O)cn4ncnc(N)c34)sc12]

A suspension of Intermediate 12A (80 mg, 218 μmol), 10% Pd/C (80 mg) and acetic anhydride (50 μl) in methanol (10 ml) was stirred for 1 h at rt under 1 atm of hydrogen. The mixture was then filtered through kieselguhr and the filtrate evaporated. Column chromatography over silica gel (cyclohexane/50-100% ethyl acetate gradient) afforded 56 mg (67% of th.) of the title compound.

LC-MS (method 2): $R_t$=0.78 min; MS (ESIpos): m/z=382 $(M+H)^+$ $^1$H-NMR (400 MHz, DMSO-$d_6$): δ=8.18 (t, 1H), 7.92 (s, 1H), 7.70 (s, 1H), 7.36 (s, 1H), 7.31 (s, 1H), 6.85 (s, 1H), 4.21 (d, 2H), 3.95 (s, 3H), 2.45 (s, 3H), 1.81 (s, 3H) ppm.

Example 10

2-({[4-Amino-5-(7-methoxy-5-methyl-1-benzothiophen-2-yl)pyrrolo[2,1-f][1,2,4]triazin-6-yl]-methyl}amino)ethanol dihydrochloride

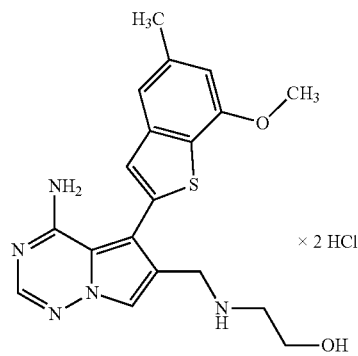 [SMILES: COc1cc(C)cc2cc(-c3c(CNCCO)cn4ncnc(N)c34)sc12]

A solution of Intermediate 13A (80 mg, 236 μmol) in THF (0.95 ml) was treated with 2-aminoethanol (71 μl, 1.18 mmol), sodium triacetoxyborohydride (250 mg, 1.18 mmol) and acetic acid (27 μl, 472 μmol), and the mixture was

Example 11

4-{[4-Amino-5-(7-methoxy-5-methyl-1-benzothiophen-2-yl)pyrrolo[2,1-f][1,2,4]triazin-6-yl]-methyl}piperazin-2-one

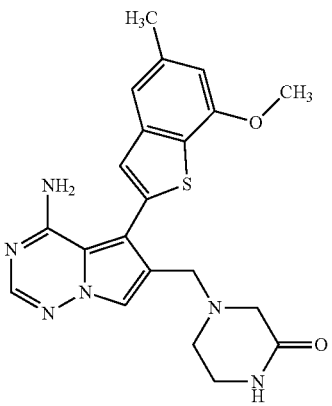 [SMILES: COc1cc(C)cc2cc(-c3c(CN4CCNC(=O)C4)cn4ncnc(N)c34)sc12]

A solution of Intermediate 13A (50 mg, 148 μmol) in THF (2 ml) was treated with piperazin-2-one (74 mg, 739 μmol), sodium triacetoxyborohydride (157 mg, 739 μmol) and acetic acid (17 μl, 296 mmol), and the mixture was stirred at 60° C. for 16 h. After this, the reaction mixture was directly separated by preparative RP-HPLC (Reprosil C18, gradient 20-40% acetonitrile/0.2% aq. TFA). The product fractions were combined and evaporated to dryness, and the residue was dissolved in methanol and filtered through an anion exchange cartridge (StratoSpheres SPE, PL-HCO₃ MP-resin). The cartridge was eluted with methanol, and the filtrate was evaporated yielding 28 mg (45% of th.) of the title compound.

LC-MS (method 2): $R_t$=0.73 min; MS (ESIpos): m/z=423 (M+H)$^+$ $^1$H-NMR (400 MHz, DMSO-d$_6$): δ=7.92 (s, 1H), 7.9 (br. s, 1H), 7.77 (s, 1H), 7.71 (s, 1H), 7.37 (s, 1H), 7.30 (s, 1H), 6.84 (s, 1H), 5.7 (br. s, 1H), 3.95 (s, 3H), 3.53 (s, 2H), 3.09 (br. s, 2H), 2.87 (s, 2H), 2.45 (s, 3H) ppm.

Example 12 rac-N²-{[4-Amino-5-(7-methoxy-5-methyl-1-benzothiophen-2-yl)pyrrolo[2,1-f][1,2,4]triazin-6-yl]-methyl}alaninamide

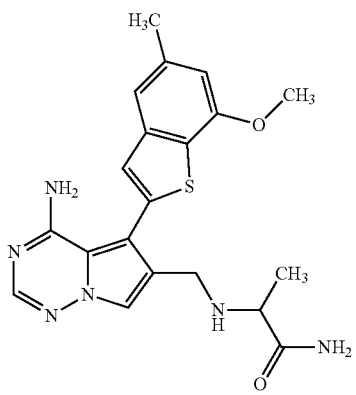 [SMILES: COc1cc(C)cc2cc(-c3c(CNC(C)C(N)=O)cn4ncnc(N)c34)sc12]

A solution of Intermediate 13A (48 mg, 142 μmol) in THF (1.9 ml) was treated with D,L-alaninamide hydrochloride (88 mg, 709 μmol), sodium triacetoxyborohydride (150 mg, 709 μmol) and acetic acid (16 μl, 284 μmol), and the mixture was stirred at 60° C. for 16 h. After this, the reaction mixture was directly separated by preparative RP-HPLC (Reprosil C18, gradient 30-50% acetonitrile/0.2% aq. formic acid). The product fractions were combined, neutralized with 1 M aq. ammonia and concentrated under reduced pressure. The remaining aqueous solution was diluted 1:1 with 1,4-dioxane and then lyophilized yielding 20 mg (35% of th.) of the title compound.

LC-MS (method 4): $R_t$=0.57 min; MS (ESIpos): m/z=411 (M+H)$^+$ $^1$H-NMR (400 MHz, methanol-d$_4$): δ=7.84 (s, 1H), 7.78 (s, 1H), 7.32 (s, 1H), 7.30 (s, 1H), 6.80 (s, 1H), 3.99 (s, 3H), 3.83-3.96 (m, 2H), 3.36 (q, 1H), 2.49 (s, 3H), 1.27 (d, 3H) ppm.

Example 13

N²-{[4-Amino-5-(7-methoxy-5-methyl-1-benzothiophen-2-yl)pyrrolo[2,1-f][1,2,4]triazin-6-yl]-methyl}-N-methylglycinamide

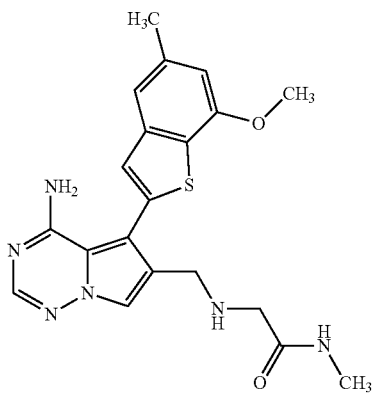 [SMILES: CNC(=O)CNCc1cn2ncnc(N)c2c1-c1cc2cc(C)cc(OC)c2s1]

A solution of Intermediate 13A (50 mg, 148 μmol) in THF (2 ml) was treated with N-methylglycinamide hydrochloride (92 mg, 739 μmol), sodium triacetoxyborohydride (157 mg, 739 μmol) and acetic acid (17 μl, 296 μmol), and the mixture was stirred at 60° C. for 16 h. After this, the reaction mixture was directly separated by preparative RP-HPLC (Reprosil C18, gradient 20-40% acetonitrile/0.2% aq. TFA). The product fractions were combined and evaporated to dryness, and the residue was dissolved in methanol and filtered through an anion exchange cartridge (StratoSpheres SPE, PL-HCO$_3$ MP-resin). The cartridge was eluted with methanol, and the filtrate was evaporated yielding 7 mg (10% of th.) of the title compound.

LC-MS (method 4): R$_t$=0.58 min; MS (ESIpos): m/z=411 (M+H)$^+$ $^1$H-NMR (400 MHz, DMSO-d$_6$): inter al. δ=7.91 (s, 1H), 7.9 (br. s, 1H), 7.83 (s, 1H), 7.60-7.66 (m, 1H), 7.35 (s, 1H), 7.30 (s, 1H), 6.84 (s, 1H), 5.7 (br. s, 1H), 3.95 (s, 3H), 3.65 (d, 2H), 3.04 (d, 2H), 2.45 (s, 3H) ppm.

Example 14

N$^2$-{[4-Amino-5-(7-methoxy-5-methyl-1-benzothiophen-2-yl)pyrrolo[2,1-f][1,2,4]triazin-6-yl]-methyl}-N$^2$-methylglycinamide

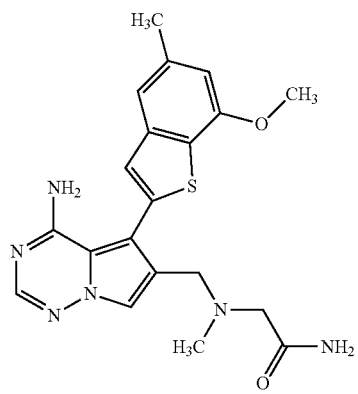 [SMILES: COc1cc(C)cc2cc(-c3c(CN(C)CC(N)=O)cn4ncnc(N)c34)sc12]

A solution of Intermediate 13A (48 mg, 142 μmol) in THF (2 ml) was treated with N$^2$-methylglycinamide hydrochloride (88 mg, 709 μmol), sodium triacetoxyborohydride (150 mg, 709 μmol) and acetic acid (16 μl, 284 μmol), and the mixture was stirred at 60° C. for 16 h. After this, the reaction mixture was directly separated by preparative RP-HPLC (Reprosil C18, gradient 30-50% acetonitrile/0.2% aq. formic acid). The product fractions were combined, neutralized with 1 M aq. ammonia and concentrated under vacuum. The remaining aqueous solution was diluted 1:1 with 1,4-dioxane and lyophilized. The product thus obtained was dissolved in ethyl acetate and washed with brine. The organic layer was dried with magnesium sulfate, filtered and evaporated to dryness. The residue was purified by preparative TLC (silica gel, dichloromethane/7 M ammonia in methanol 20:1) yielding 4 mg (6% of th.) of the title compound.

LC-MS (method 4): R$_t$=0.58 min; MS (ESIpos): m/z=411 (M+H)$^+$ $^1$H-NMR (400 MHz, DMSO-d$_6$): δ=7.92-7.94 (m, 2H), 7.36 (s, 1H), 7.30 (s, 1H), 7.09-7.14 (m, 1H), 7.04-7.09 (m, 1H), 6.84 (s, 1H), 5.7 (br. s, 1H), 3.94-3.96 (m, 5H), 3.57 (s, 2H), 2.83 (s, 2H), 2.45 (s, 3H), 2.15 (s, 3H) ppm.

Example 15

Ethyl N-{[4-amino-5-(7-methoxy-5-methyl-1-benzothiophen-2-yl)pyrrolo[2,1-f][1,2,4]triazin-6-yl]-methyl}glycinate dihydrochloride

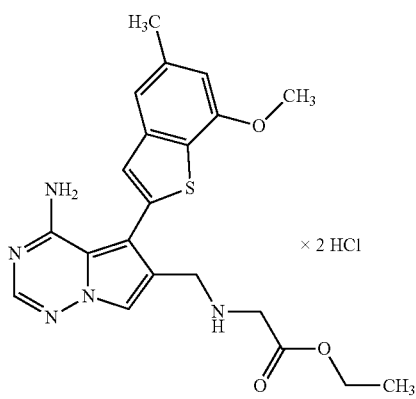 [SMILES: CCOC(=O)CNCc1cn2ncnc(N)c2c1-c1cc2cc(C)cc(OC)c2s1]

A solution of Intermediate 13A (150 mg, 443 μmol) in THF (4 ml) was treated with ethyl glycinate dihydrochloride (309 mg, 2.22 mmol), sodium triacetoxyborohydride (469 mg, 2.22 mmol) and acetic acid (51 μl, 887 μmol), and the mixture was stirred at 60° C. for 16 h. After this, the reaction mixture was directly separated by preparative RP-HPLC (Reprosil C18, gradient 30-50% acetonitrile/0.2% aq. TFA). The product fractions were combined, diluted with 1 M hydrochloric acid and evaporated to dryness yielding 38 mg (17% of th.) of the title compound.

LC-MS (method 2): R$_t$=0.69 min; MS (ESIpos): m/z=426 (M+H)$^+$ $^1$H-NMR (400 MHz, DMSO-d$_6$): δ=9.40 (br. s, 2H), 8.1 (br. s, 1H), 7.99 (s, 2H), 7.43 (s, 1H), 7.33 (s, 1H), 6.88 (s, 1H), 5.9 (br. s, 1H), 4.22 (br. s, 2H), 4.05 (q, 2H), 3.96 (s, 3H), 3.90 (br. s, 2H), 2.46 (s, 3H), 1.15 (t, 3H) ppm.

Example 16

N$^2$-{[4-Amino-5-(7-methoxy-5-methyl-1-benzothiophen-2-yl)pyrrolo[2,1-f][1,2,4]triazin-6-yl]-methyl}glycinamide

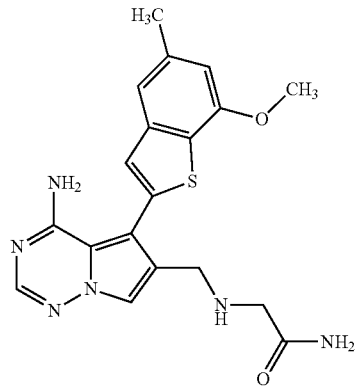 [SMILES: COc1cc(C)cc2cc(-c3c(CNCC(N)=O)cn4ncnc(N)c34)sc12]

The compound from Example 15 (32 mg, 65 μmol) was dissolved in a 7 M solution of ammonia in methanol (2 ml), and the solution was stirred for 33 h at 60° C. After this, the reaction mixture was directly separated by preparative RP-HPLC (Reprosil C18, gradient 20-40% acetonitrile/0.2% aq. TFA). The product fractions were combined and evaporated to dryness, and the residue was dissolved in methanol and filtered through an anion exchange cartridge (StratoSpheres SPE, PL-HCO$_3$ MP-resin). The cartridge was eluted with methanol, and the filtrate was evaporated yielding 4 mg (16% of th.) of the title compound.

$^1$H-NMR (400 MHz, DMSO-d$_6$): δ=7.90 (s, 1H), 7.79 (s, 1H), 7.47-7.98 (br. s, 1H), 7.35 (s, 1H), 7.30 (s, 1H), 7.22 (br. s, 1H), 6.97 (br. s, 1H), 6.84 (s, 1H), 5.73 (br. s, 1H), 3.95 (s, 3H), 3.67 (s, 2H), 3.03 (s, 2H), 2.45 (s, 3H) ppm.

Example 17

1-({[4-Amino-5-(7-methoxy-5-methyl-1-benzothiophen-2-yl)pyrrolo[2,1-f][1,2,4]triazin-6-yl]methyl}amino)-2-methylpropan-2-ol dihydrochloride

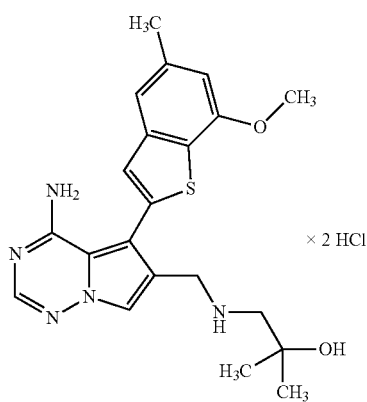 [SMILES: COc1cc(C)cc2cc(-c3c(CNCC(C)(C)O)cn4ncnc(N)c34)sc12]

A solution of Intermediate 13A (50 mg, 148 µmol) in THF (2 ml) was treated with 1-amino-2-methylpropan-2-ol hydrochloride (93 mg, 739 µmol), sodium triacetoxyborohydride (157 mg, 739 µmol) and acetic acid (17 µl, 296 µmol), and the mixture was stirred at 60° C. for 16 h. After this, the reaction mixture was directly separated by preparative RP-HPLC (Reprosil C18, gradient 30-50% acetonitrile/0.2% aq. TFA). The product fractions were combined, diluted with 1 M hydrochloric acid and evaporated to dryness yielding 30 mg (42% of th.) of the title compound.

LC-MS (method 2): R$_t$=0.70 min; MS (ESIpos): m/z=412 (M+H)$^+$ $^1$H-NMR (400 MHz, methanol-d$_4$): δ=8.24 (s, 1H), 8.14 (s, 1H), 7.53 (s, 1H), 7.51 (s, 1H), 6.87 (s, 1H), 4.33 (s, 2H), 4.00 (s, 3H), 2.83 (s, 2H), 2.50 (s, 3H), 1.20 (s, 6H) ppm.

Example 18 rac-1-{[4-Amino-5-(7-methoxy-5-methyl-1-benzothiophen-2-yl)pyrrolo[2,1-f][1,2,4]triazin-6-yl]methyl}pyrrolidin-3-ol dihydrochloride

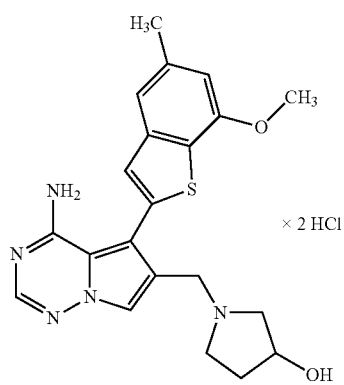 [SMILES: COc1cc(C)cc2cc(-c3c(CN4CCC(O)C4)cn4ncnc(N)c34)sc12]

A solution of Intermediate 13A (50 mg, 148 µmol) in THF (2 ml) was treated with rac-3-hydroxypyrrolidine (64 mg, 739 µmol), sodium triacetoxyborohydride (157 mg, 739 µmol) and acetic acid (17 µl, 296 µmol), and the mixture was stirred at 60° C. for 16 h. After this, the reaction mixture was directly separated by preparative RP-HPLC (Reprosil C18, gradient 30-50% acetonitrile/0.2% aq. TFA). The product fractions were combined, treated with 1 M hydrochloric acid (2 ml) and evaporated to dryness yielding 25 mg (35% of th.) of the title compound.

LC-MS (method 2): R$_t$=0.67 min; MS (ESIpos): m/z=410 (M+H)$^+$ $^1$H-NMR (400 MHz, methanol-d$_4$): δ=8.24-8.32 (m, 1H), 8.13 (s, 1H), 7.5-7.55 (m, 1H), 7.37 (s, 1H), 6.87 (s, 1H), 4.43-4.64 (m, 3H), 4.00 (s, 3H), 3.52-3.72 (m, 1H), 3.2-3.4 (s, 1H), 2.99-3.17 (m, 2H), 2.51 (s, 3H), 2.01-2.29 (m, 1H), 1.88-2.01 (m, 1H) ppm.

Example 19 rac-1-{[4-Amino-5-(7-methoxy-5-methyl-1-benzothiophen-2-yl)pyrrolo[2,1-f][1,2,4]triazin-6-yl]methyl}prolinamide dihydrochloride

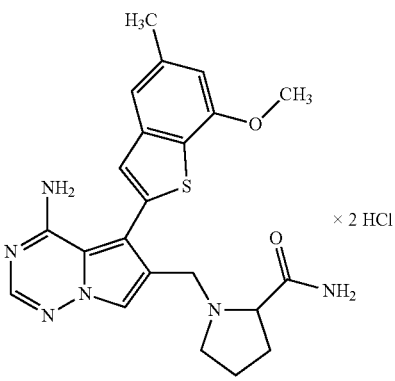 [SMILES: COc1cc(C)cc2cc(-c3c(CN4CCCC4C(N)=O)cn4ncnc(N)c34)sc12]

A solution of Intermediate 13A (50 mg, 148 µmol) in THF (2 ml) was treated with D,L-prolinamide hydrochloride (111 mg, 739 μmol), sodium triacetoxyborohydride (157 mg, 739 μmol) and acetic acid (17 μl, 296 μmol), and the mixture was stirred at 60° C. for 16 h. After this, the reaction mixture was directly separated by preparative RP-HPLC (Reprosil C18, gradient 20-40% acetonitrile/0.2% aq. TFA). The product fractions were combined, diluted with 1 M hydrochloric acid and evaporated to dryness yielding 35 mg (46% of th.) of the title compound.

LC-MS (method 4): $R_t$=0.61 min; MS (ESIpos): m/z=437 (M+H)$^+$ $^1$H-NMR (400 MHz, DMSO-d$_6$): δ=9.65 (br. s, 1H), 8.25 (br. s, 1H), 8.03 (s, 2H), 7.99 (s, 1H), 7.72 (s, 1H), 7.50 (s, 1H), 7.34 (s, 1H), 6.88 (s, 1H), 6.0 (br. s, 1H), 4.37 (m, 2H), 4.05 (m, 1H), 3.96 (s, 3H), 3.47 (br. s, 1H), 3.09 (br. s, 1H), 2.47 (s, 3H), 2.28-2.39 (m, 1H), 1.72-1.96 (m, 3H) ppm.

Example 20

3-({[4-Amino-5-(7-methoxy-5-methyl-1-benzothiophen-2-yl)pyrrolo[2,1-f][1,2,4]triazin-6-yl]methyl}amino)propan-1-ol dihydrochloride

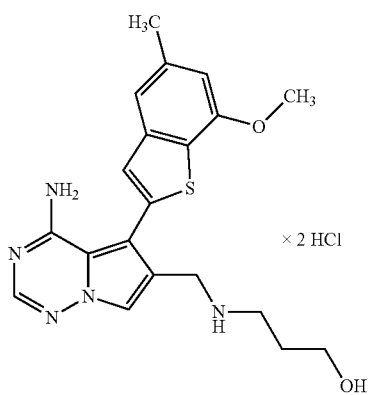 [SMILES: COc1cc(C)cc2cc(-c3c(CNCCCO)cn4ncnc(N)c34)sc12]

A solution of Intermediate 13A (50 mg, 148 μmol) in THF (2 ml) was treated with 3-amino-1-propanol (55 mg, 739 μmol), sodium triacetoxyborohydride (157 mg, 739 μmol) and acetic acid (17 μl, 296 μmol), and the mixture was stirred at 60° C. for 16 h. After this, the reaction mixture was directly separated by preparative RP-HPLC (Reprosil C18, gradient 30-50% acetonitrile/0.2% aq. TFA). The product fractions were combined, diluted with 1 M hydrochloric acid and evaporated to dryness yielding 28 mg (39% of th.) of the title compound.

LC-MS (method 4): $R_t$=0.59 min; MS (ESIpos): m/z=398 (M+H)$^+$ $^1$H-NMR (400 MHz, methanol-d$_4$): δ=8.20 (s, 1H), 8.13 (s, 1H), 7.52 (s, 1H), 7.37 (s, 1H), 6.87 (s, 1H), 4.31 (s, 2H), 4.00 (s, 3H), 3.62 (t, 2H), 3.09 (t, 2H), 2.51 (s, 3H), 1.82 (quin, 2H) ppm.

Example 21

1-(4-{[4-Amino-5-(7-methoxy-5-methyl-1-benzothiophen-2-yl)pyrrolo[2,1-f][1,2,4]triazin-6-yl]methyl}piperazin-1-yl)ethanone

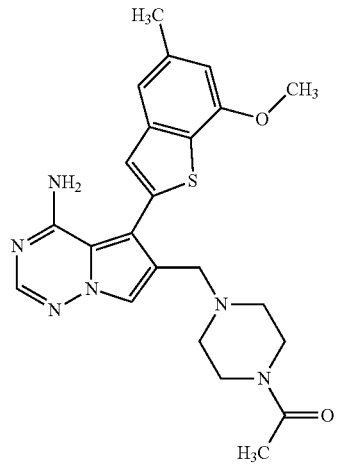 [SMILES: COc1cc(C)cc2cc(-c3c(CN4CCN(C(C)=O)CC4)cn4ncnc(N)c34)sc12]

A solution of Intermediate 13A (41 mg, 121 μmol) in THF (1.6 ml) was treated with N-acetylpiperazine (78 mg, 606 μmol), sodium triacetoxyborohydride (128 mg, 606 μmol) and acetic acid (14 μl, 242 μmol), and the mixture was stirred at 60° C. for 3 h. After this, the reaction mixture was directly separated by preparative RP-HPLC (Reprosil C18, gradient 30-50% acetonitrile/0.2% aq. TFA). The product fractions were combined and evaporated to dryness, and the residue was dissolved in methanol and filtered through an anion exchange cartridge (StratoSpheres SPE, PL-HCO$_3$ MP-resin). The cartridge was eluted with methanol, and the filtrate was evaporated yielding 31 mg (57% of th.) of the title compound.

LC-MS (method 4): $R_t$=0.61 min; MS (ESIpos): m/z=451 (M+H)$^+$ $^1$H-NMR (400 MHz, DMSO-d$_6$): δ=7.88 (s, 1H), 7.69 (s, 1H), 7.54-8.13 (m, 1H), 7.39 (s, 1H), 7.31 (s, 1H), 6.84 (s, 1H), 5.40-6.06 (m, 1H), 3.95 (s, 3H), 3.48 (s, 2H), 3.37 (br. s, 4H), 2.45 (s, 3H), 2.30-2.36 (m, 2H), 2.22-2.29 (m, 2H), 1.95 (s, 3H) ppm.

Example 22 tert-Butyl 4-{[4-amino-5-(7-methoxy-5-methyl-1-benzothiophen-2-yl)pyrrolo[2,1-f][1,2,4]triazin-6-yl]methyl}piperazine-1-carboxylate trifluoroacetate

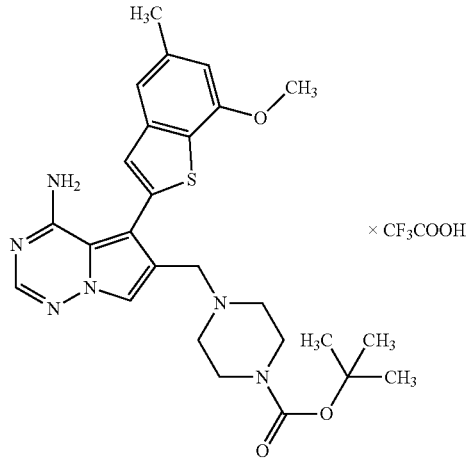 [SMILES: COc1cc(C)cc2cc(-c3c(CN4CCN(C(=O)OC(C)(C)C)CC4)cn4ncnc(N)c34)sc12]

A solution of Intermediate 13A (70 mg, 207 µmol) in methanol (2 ml) was treated with tert-butyl piperazine-1-carboxylate (116 mg, 621 µmol), sodium cyanoborohydride (65 mg, 1.03 mmol) and acetic acid (37 µl, 621 µmol). The reaction mixture was stirred at 60° C. for 16 h. After cooling to rt, the mixture was directly subjected to preparative RP-HPLC (Reprosil C18, gradient 30-50% acetonitrile/0.2% aq. TFA). The product fractions were combined and evaporated to dryness to yield 120 mg (90% of th.) of the title compound.

LC-MS (method 2): $R_t$=0.83 min; MS (ESIpos): m/z=509 (M+H)$^+$ $^1$H-NMR (400 MHz, DMSO-d$_6$): δ=9.7 (br. s, 1H), 8.1 (br. s, 1H), 8.01 (s, 1H), 8.00 (s, 1H), 7.46 (s, 1H), 7.34 (s, 1H), 6.88 (s, 1H), 5.8 (br. s, 1H), 4.33 (br. s, 2H), 3.86-4.00 (m, 2H), 3.96 (s, 3H), 3.24-3.39 (m, 2H), 2.99-3.10 (m, 2H), 2.76-2.95 (m, 2H), 2.46 (s, 3H), 1.36 (s, 9H) ppm.

Example 23

5-(7-Methoxy-5-methyl-1-benzothiophen-2-yl)-6-(morpholin-4-ylmethyl)pyrrolo[2,1-f][1,2,4]triazin-4-amine

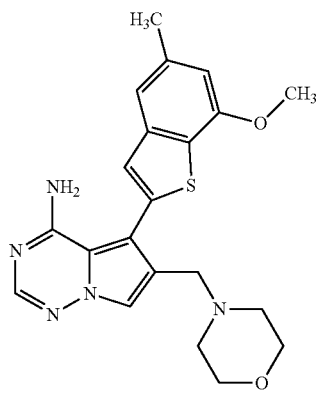 [SMILES: COc1cc(C)cc2cc(-c3c(CN4CCOCC4)cn4ncnc(N)c34)sc12]

A solution of Intermediate 13A (41 mg, 121 µmol) in THF (1.6 ml) was treated with morpholine (53 mg, 606 µmol), sodium triacetoxyborohydride (128 mg, 606 µmol) and acetic acid (14 µl, 242 µmol), and the mixture was stirred at 60° C. for 3 h. After this, the reaction mixture was directly separated by preparative RP-HPLC (Reprosil C18, gradient 30-50% acetonitrile/0.2% aq. TFA). The product fractions were combined and evaporated to dryness, and the residue was dissolved in methanol and filtered through an anion exchange cartridge (StratoSpheres SPE, PL-HCO$_3$ MP-resin). The cartridge was eluted with methanol, and the filtrate was evaporated yielding 27 mg (54% of th.) of the title compound.

LC-MS (method 4): $R_t$=0.64 min; MS (ESIpos): m/z=410 (M+H)$^+$ $^1$H-NMR (400 MHz, DMSO-d$_6$): δ=7.91 (s, 1H), 7.72 (s, 1H), 7.6-8.1 (br. s, 1H), 7.39 (s, 1H), 7.30 (s, 1H), 6.84 (s, 1H), 5.71 (br. s, 1H), 3.95 (s, 3H), 3.52 (br. t, 4H), 3.44 (s, 2H), 2.45 (s, 3H), 2.32 (br. s, 4H) ppm.

Example 24

N-[2-({[4-Amino-5-(7-methoxy-5-methyl-1-benzothiophen-2-yl)pyrrolo[2,1-f][1,2,4]triazin-6-yl]methyl}amino)ethyl]acetamide trifluoroacetate

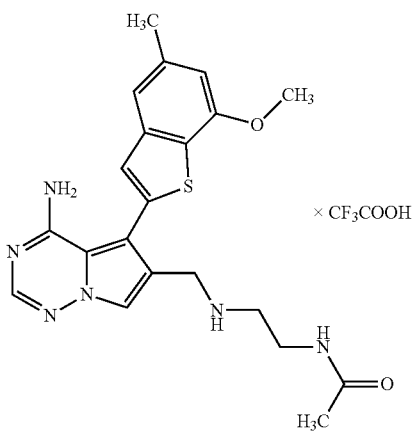 [SMILES: COc1cc(C)cc2cc(-c3c(CNCCNC(C)=O)cn4ncnc(N)c34)sc12]

A solution of Intermediate 13A (50 mg, 148 µmol) in methanol (2 ml) was treated with N-(2-aminoethyl)acetamide (23 mg, 222 µmol), sodium cyanoborohydride (46 mg, 739 µmol) and acetic acid (17 µl, 296 µmol), and the mixture was stirred at 60° C. for 16 h. After this, the reaction mixture was directly separated by preparative RP-HPLC (Reprosil C18, gradient 30-50% acetonitrile/0.2% aq. TFA). The product fractions were combined and evaporated to dryness yielding 17 mg (21% of th.) of the title compound.

LC-MS (method 2): $R_t$=0.65 min; MS (ESIpos): m/z=425 (M+H)$^+$ $^1$H-NMR (400 MHz, DMSO-d$_6$): δ=8.92 (br. s, 2H), 8.25 (br. s, 1H), 8.04-8.08 (m, 1H), 8.03 (s, 1H), 8.00 (s, 1H), 7.44 (s, 1H), 7.33 (s, 1H), 6.88 (s, 1H), 6.1 (br. s, 1H), 4.18 (br. s, 2H), 3.96 (s, 3H), 3.27 (q, 2H), 2.88-2.98 (m, 2H), 2.46 (s, 3H), 1.81 (s, 3H) ppm.

Example 25

5-(7-Methoxy-5-methyl-1-benzothiophen-2-yl)-6-(piperazin-1-ylmethyl)pyrrolo[2,1-f][1,2,4]triazin-4-amine trihydrochloride

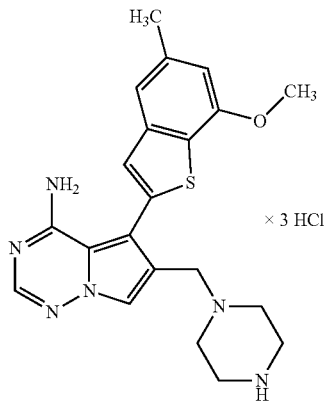 [SMILES: COc1cc(C)cc2cc(-c3c(CN4CCNCC4)cn4ncnc(N)c34)sc12]

A suspension of Example 22 (109 mg, 175 μmol) in 1,4-dioxane (2 ml) was treated with a 4 N solution of hydrogen chloride in 1,4-dioxane (4 ml). After stirring for 2 h, the suspension was evaporated to dryness yielding 98 mg (quant.) of the title compound.

LC-MS (method 2): $R_t$=0.70 min; MS (ESIpos): m/z=409 $(M+H)^+$ $^1$H-NMR (400 MHz, methanol-$d_4$): δ=8.33 (s, 1H), 8.13 (s, 1H), 7.55 (s, 1H), 7.38 (s, 1H), 6.86 (s, 1H), 4.28 (s, 2H), 4.00 (s, 3H), 3.60-3.77 (m, 4H), 3.3-3.5 (m, 4H), 2.50 (s, 3H) ppm.

Example 26 rac-1-({[4-Amino-5-(7-methoxy-5-methyl-1-benzothiophen-2-yl)pyrrolo[2,1-f][1,2,4]triazin-6-yl]methyl}amino)propan-2-ol dihydrochloride

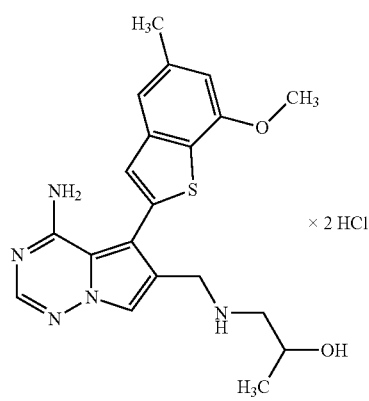 [SMILES: COc1cc(C)cc2cc(-c3c(CNCC(C)O)cn4ncnc(N)c34)sc12]

A solution of Intermediate 13A (50 mg, 148 μmol) in methanol (2 ml) was treated with rac-1-aminopropan-2-ol (33 mg, 443 μmol), sodium cyanoborohydride (46 mg, 739 μmol) and acetic acid (25 μl, 443 μmol), and the mixture was stirred at 60° C. for 16 h. After this, the reaction mixture was directly separated by preparative RP-HPLC (Reprosil C18, gradient 30-50% acetonitrile/0.2% aq. TFA). The product fractions were combined, diluted with 1 M hydrochloric acid and evaporated to dryness yielding 25 mg (36% of th.) of the title compound.

LC-MS (method 2): $R_t$=0.69 min; MS (ESIpos): m/z=398 $(M+H)^+$ $^1$H-NMR (400 MHz, DMSO-$d_6$): δ=9.22 (br. s, 1H), 9.02 (br. s, 1H), 8.4 (br. s, 1H), 8.18 (s, 1H), 8.07 (s, 1H), 7.48 (s, 1H), 7.34 (s, 1H), 6.88 (s, 1H), 6.3 (br. s, 1H), 4.10-4.17 (m, 2H), 3.96 (s, 3H), 3.81-3.90 (m, 1H), 2.79-2.88 (m, 1H), 2.59-2.69 (m, 1H), 2.46 (s, 3H), 1.03 (d, 3H) ppm.

Example 27

(3S)-3-({[4-Amino-5-(7-methoxy-5-methyl-1-benzothiophen-2-yl)pyrrolo[2,1-f][1,2,4]triazin-6-yl]methyl}amino)pyrrolidin-2-one dihydrochloride

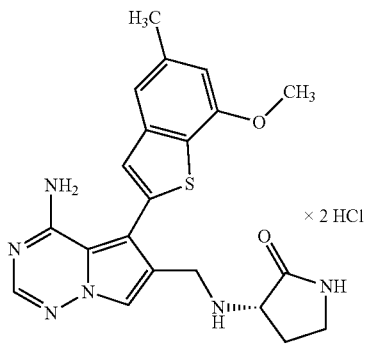 [SMILES: COc1cc(C)cc2cc(-c3c(CN[C@H]4CCNC4=O)cn4ncnc(N)c34)sc12]

A solution of Intermediate 13A (50 mg, 148 μmol) in methanol (2 ml) was treated with (3S)-3-aminopyrrolidin-2-one (44 mg, 443 μmol), sodium cyanoborohydride (46 mg, 739 μmol) and acetic acid (25 μl, 443 μmol), and the mixture was stirred at 60° C. for 16 h. After this, the reaction mixture was directly separated by preparative RP-HPLC (Reprosil C18, gradient 30-50% acetonitrile/0.2% aq. TFA). The product fractions were combined, diluted with 1 M hydrochloric acid and evaporated to dryness yielding 25 mg (36% of th.) of the title compound.

LC-MS (method 2): $R_t$=0.64 min; MS (ESIpos): m/z=423 $(M+H)^+$ $^1$H-NMR (400 MHz, methanol-$d_4$): δ=8.22 (s, 1H), 8.14 (s, 1H), 7.55 (s, 1H), 7.38 (s, 1H), 6.87 (s, 1H), 4.39-4.61 (m, 2H), 4.07 (dd, 1H), 4.00 (s, 3H), 3.25-3.41 (m, 2H), 2.50 (s, 3H), 2.32-2.44 (m, 1H), 1.98-2.11 (m, 1H) ppm.

Example 28

6-(Ethoxymethyl)-5-(7-methoxy-5-methyl-1-benzothiophen-2-yl)pyrrolo[2,1-f][1,2,4]triazin-4-amine

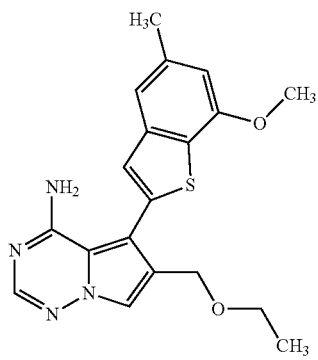 [SMILES: CCOCc1cn2ncnc(N)c2c1-c1cc2cc(C)cc(OC)c2s1]

The compound from Example 32 (200 mg, 587 μmol) in dichloromethane (5 ml) was treated with thionyl chloride (64 μl, 881 μmol). The mixture was stirred for 15 min and then evaporated. The residue was refluxed in ethanol (5 ml) for 1 h, then treated with DIPEA (204 μl, 1.17 mmol) and refluxed again overnight. The reaction mixture was evaporated, and the residue was purified by column chromatography (silica gel, dichloromethane/methanol 98:2→95:5) affording 202 mg (90% of th.) of the title compound.

LC-MS (method 5): $R_t$=2.32 min; MS (ESIpos): m/z=369 (M+H)$^+$ $^1$H-NMR (400 MHz, DMSO-d$_6$): δ=8.31-7.59 (br. s, 1H), 7.93 (s, 1H), 7.81 (s, 1H), 7.35 (s, 1H), 7.30 (s, 1H), 6.84 (s, 1H), 6.20-5.50 (br. s, 1H), 4.41 (s, 2H), 3.95 (s, 3H), 3.41 (q, 2H), 2.45 (s, 3H), 1.08 (t, 3H) ppm.

Example 29

4-{[4-Amino-5-(5-methyl-1-benzothiophen-2-yl)pyrrolo[2,1-f][1,2,4]triazin-6-yl]methyl}piperazin-2-one

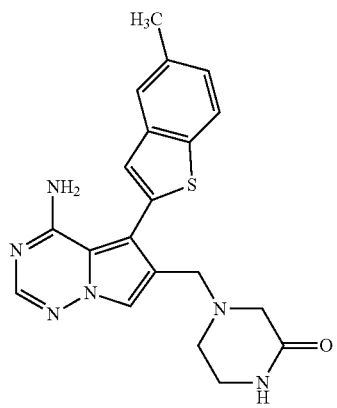 [SMILES: Cc1ccc2sc(-c3c(CN4CCNC(=O)C4)cn4ncnc(N)c34)cc2c1]

Under argon, a solution of Intermediate 15A (70 mg, 215 μmol) in degassed THF (0.43 ml) was added to (5-methyl-1-benzothiophen-2-yl)boronic acid (62 mg, 323 μmol) and (2'-aminobiphenyl-2-yl)(chloro)palladium-dicyclohexyl(2',4',6'-triisopropylbiphenyl-2-yl)phosphine (1:1; 16 mg, 22 μmol; see S. L. Buchwald et al., J. Am. Chem. Soc. 132 (40), 14073-14075 (2010)). A degassed 0.5 M aq. potassium phosphate solution (0.86 ml) was then added, and the resulting mixture was stirred at 40° C. overnight. After this, the reaction mixture was diluted with sat. aq. sodium hydrogencarbonate solution and sat. aq. sodium chloride solution (1:1). The aqueous phase was extracted three times with ethyl acetate, the combined organic phases were evaporated, and the residue was purified by preparative RP-HPLC (Reprosil C18, gradient 10-95% acetonitrile/0.1% aq. TFA). The product fractions were combined and evaporated to dryness, and the residue was dissolved in methanol and filtered through an anion exchange cartridge (StratoSpheres SPE, PL-HCO$_3$ MP-resin). The cartridge was eluted with methanol, and the filtrate was evaporated affording 25 mg (30% of th.) of the title compound.

LC-MS (method 3): $R_t$=2.31 min; MS (ESIpos): m/z=393 (M+H)$^+$ $^1$H-NMR (400 MHz, DMSO-d$_6$): δ=7.92 (s, 1H), 7.88 (d, 1H), 7.78 (s, 1H), 7.70 (br. s, 2H), 7.39 (s, 1H), 7.24 (d, 1H), 3.53 (s, 2H), 3.15-3.04 (m, 2H), 2.88 (s, 2H), 2.44 (s, 3H) ppm.

Example 30

4-{[4-Amino-5-(7-methoxy-1-benzothiophen-2-yl)pyrrolo[2,1-f][1,2,4]triazin-6-yl]methyl}piperazin-2-one

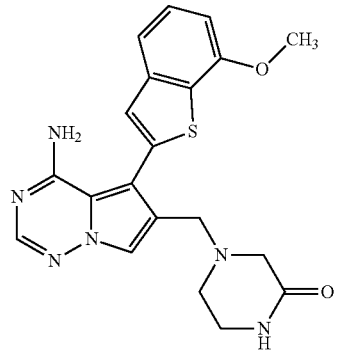 [SMILES: COc1cccc2cc(-c3c(CN4CCNC(=O)C4)cn4ncnc(N)c34)sc12]

Under argon, a solution of Intermediate 15A (50 mg, 154 μmol) in degassed THF (0.31 ml) was added to (7-methoxy-1-benzothiophen-2-yl)boronic acid [U.S. Pat. No. 6,025,382, Example 75/Part C] (47 mg, 231 μmol) and (2'-aminobiphenyl-2-yl)(chloro)palladium-dicyclohexyl(2',4',6'-triisopropylbiphenyl-2-yl)phosphine (1:1; 12 mg, 15 μmol; see S. L. Buchwald et al., J. Am. Chem. Soc. 132 (40), 14073-14075 (2010)). A degassed 0.5 M aq. potassium phosphate solution (0.62 ml) was then added, and the resulting mixture was stirred at 40° C. for 3.5 h. After this, the two phases were separated, and the aqueous phase was extracted three times with ethyl acetate. The combined organic phases were washed with sat. aq. sodium hydrogencarbonate solution, followed by sat. aq. sodium chloride solution, dried over magnesium sulfate and evaporated. The crude product was purified by preparative RP-HPLC (Reprosil C18, gradient 10-95% acetonitrile/0.1% aq. TFA). The product fractions were combined and evaporated to dryness, and the residue was dissolved in methanol and filtered through an anion exchange cartridge (StratoSpheres SPE, PL-HCO$_3$ MP-resin). The cartridge was eluted with methanol, and the filtrate was evaporated affording 21 mg (33% of th.) of the title compound.

LC-MS (method 2): $R_t$=0.68 min; MS (ESIpos): m/z=409 (M+H)$^+$ $^1$H-NMR (400 MHz, DMSO-d$_6$): δ=7.92 (s, 1H), 7.78 (s, 1H), 7.71 (br. s, 1H), 7.50 (d, 1H), 7.46 (s, 1H), 7.39 (t, 1H), 6.99 (d, 1H), 3.97 (s, 3H), 3.53 (s, 2H), 3.15-3.05 (m, 2H), 2.88 (s, 2H) ppm.

Example 31

4-{[4-Amino-5-(5-chloro-7-methoxy-1-benzothiophen-2-yl)pyrrolo[2,1-f][1,2,4]triazin-6-yl]methyl}piperazin-2-one

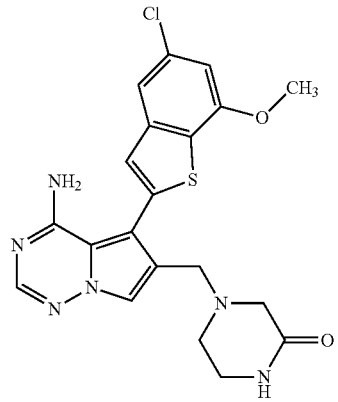 [SMILES: COc1cc(Cl)cc2cc(-c3c(CN4CCNC(=O)C4)cn4ncnc(N)c34)sc12]

Under argon, a solution of Intermediate 15A (70 mg, 215 μmol) in degassed THF (0.43 ml) was added to Intermediate 16A (114 mg, 323 μmol) and (2'-aminobiphenyl-2-yl)(chloro)palladium-dicyclohexyl(2',4',6'-triisopropylbiphenyl-2-yl)phosphine (1:1; 16 mg, 22 μmol; see S. L. Buchwald et al., *J. Am. Chem. Soc.* 132 (40), 14073-14075 (2010)). A degassed 0.5 M aq. potassium phosphate solution (0.86 ml) was then added, and the resulting mixture was stirred 1 h at 40° C., followed by 4.5 h at 60° C. After this, the reaction mixture was diluted with sat. aq. sodium hydrogencarbonate solution and sat. aq. sodium chloride solution (1:1). The aqueous phase was extracted three times with ethyl acetate, the combined organic phases were evaporated, and the residue was purified by preparative RP-HPLC (Reprosil C18, gradient 10-95% acetonitrile/0.1% aq. TFA). The product fractions were combined and evaporated to dryness, and the residue was dissolved in methanol and filtered through an anion exchange cartridge (StratoSpheres SPE, PL-HCO$_3$ MP-resin). The cartridge was eluted with methanol, and the filtrate was evaporated affording 22 mg (22% of th.) of the title compound.

LC-MS (method 3): R$_t$=2.40 min; MS (ESIpos): m/z=443 (M+H)$^+$ $^1$H-NMR (400 MHz, DMSO-d$_6$): δ=7.93 (s, 1H), 7.78 (s, 1H), 7.71 (br. s, 1H), 7.60 (d, 1H), 7.41 (s, 1H), 7.05 (d, 1H), 4.00 (s, 3H), 3.52 (s, 2H), 3.14-3.04 (m, 2H), 2.88 (s, 2H) ppm.

Example 32

[4-Amino-5-(7-methoxy-5-methyl-1-benzothiophen-2-yl)pyrrolo[2,1-f][1,2,4]triazin-6-yl]methanol

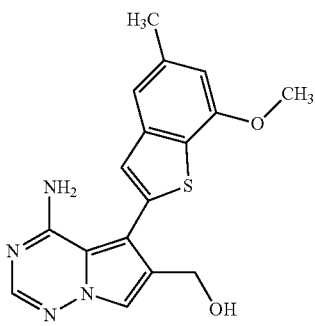 [SMILES: COc1cc(C)cc2cc(-c3c(CO)cn4ncnc(N)c34)sc12]

A suspension of Intermediate 10A (70% purity, 2.52 g, 7.26 mmol), Intermediate 6A (3.63 g, 10.9 mmol) and caesium fluoride (5.51 g, 36.3 mmol) in a THF/water mixture (10:1; 80 ml) was degassed under argon. 4-(Di-tert-butylphosphino)-N,N-dimethylaniline-dichloropalladium (2:1; 176 mg, 0.248 mmol) was added, and the resulting mixture was degassed again and stirred at 50° C. for 16 h. The reaction mixture was then washed with sat. aq. sodium chloride solution, and the organic layer was separated, dried over magnesium sulfate, filtered and evaporated. The residue was suspended in methanol, and the resulting solid was filtered off and dried in vacuo to afford 1.97 g (90% purity, 72% of th.) of the title compound.

LC-MS (method 2): R$_t$=0.85 min; MS (ESIpos): m/z=340 (M+H)$^+$ $^1$H-NMR (400 MHz, DMSO-d$_6$): δ=7.91 (s, 1H), 7.72 (s, 1H), 7.35 (s, 1H), 7.30 (s, 1H), 6.84 (s, 1H), 5.06 (t, 1H), 4.49 (d, 2H), 3.95 (s, 3H), 2.45 (s, 3H) ppm.

Example 33

4-{[4-Amino-5-(5,7-dimethoxy-1-benzothiophen-2-yl)pyrrolo[2,1-f][1,2,4]triazin-6-yl]methyl}-piperazin-2-one

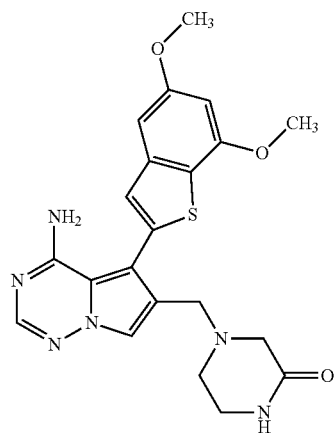 [SMILES: COc1cc(OC)c2sc(-c3c(CN4CCNC(=O)C4)cn4ncnc(N)c34)cc2c1]

To a solution of Intermediate 15A (45.5 mg, 140 μmol), Intermediate 18A (40 mg, 168 μmol) and caesium fluoride (106 mg, 700 μmol) in degassed THF/water (10:1; 2 ml) under argon was added (2'-aminobiphenyl-2-yl)(chloro)palladium-dicyclohexyl(2',4',6'-triisopropylbiphenyl-2-yl)phosphine (1:1; 7.7 mg, 9.8 μmol; see S. L. Buchwald et al., *J. Am. Chem. Soc.* 132 (40), 14073-14075 (2010)). The resulting mixture was degassed again and stirred under argon at 60° C. for 9 h. After this, the reaction mixture was separated by preparative RP-HPLC (Reprosil C18, gradient 20-40% acetonitrile/0.1% aq. TFA). The product fractions were combined and evaporated to dryness, and the residue was dissolved in methanol and filtered through an anion exchange cartridge (StratoSpheres SPE, PL-HCO$_3$ MP-resin). The cartridge was eluted with methanol, and the filtrate was evaporated affording 20 mg (31% of th.) of the title compound.

LC-MS (method 4): R$_t$=0.70 min; MS (ESIpos): m/z=439 (M+H)$^+$ $^1$H-NMR (400 MHz, DMSO-d$_6$): inter al. δ=7.92 (s, 1H), 7.76 (s, 1H), 7.36 (s, 1H), 7.05 (d, 1H), 6.62 (d, 1H), 3.94 (s, 3H), 3.84 (s, 3H), 3.54 (s, 2H), 3.07-3.13 (m, 2H), 2.88 (s, 2H) ppm.

Example 34

4-Amino-5-(7-methoxy-5-methyl-1-benzothiophen-2-yl)pyrrolo[2,1-f][1,2,4]triazine-6-carboxylic acid

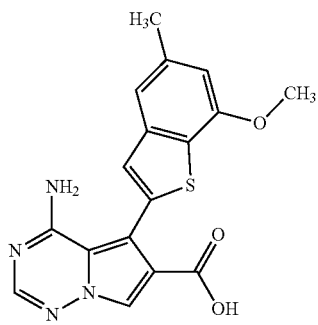 [SMILES: COc1cc(C)cc2cc(-c3c(C(=O)O)cn4ncnc(N)c34)sc12]

A solution of Intermediate 13A (1.3 g, 3.84 mmol) in a mixture of THF/water (10:1, 66 ml) was treated with a 2 M solution of 2-methyl-2-butene in THF (15.4 ml, 30.7 mmol), sodium dihydrogenphosphate (3.18 g, 23.1 mmol) and sodium chlorite (2.09 g, 23.0 mmol). The mixture was stirred at rt for 20 min. The resulting suspension was diluted with water and extracted with ethyl acetate. The organic phase was then extracted with 1 M aq. sodium hydroxide solution. The aqueous phase was acidified with 1 M hydrochloric acid to pH 3 and extracted with ethyl acetate. The organic phase was washed with brine, dried over magnesium sulfate and evaporated to yield 294 mg of the title compound (90% purity, 19% of th.).

LC-MS (method 2): $R_t$=0.87 min; MS (ESIpos): m/z=355 (M+H)$^+$ $^1$H-NMR (400 MHz, DMSO-d$_6$): δ=12.3-12.6 (br. s, 1H), 8.1-8.2 (br. s, 1H), 8.17 (s, 1H), 7.99 (s, 1H), 7.39 (s, 1H), 7.30 (s, 1H), 6.85 (s, 1H), 5.45-5.55 (br. s, 1H), 3.95 (s, 3H), 2.45 (s, 3H) ppm.

Example 35

4-Amino-5-(7-methoxy-5-methyl-1-benzothiophen-2-yl)pyrrolo[2,1-f][1,2,4]triazine-6-carboxamide

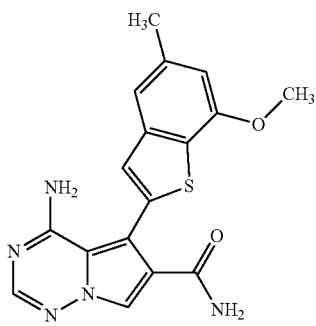

A stirred solution of Example 34 (90% purity, 55 mg, 140 μmol) in DMF (3 ml) was treated at rt with TBTU (49 mg, 154 μmol) and DIPEA (36 μl, 279 μmol). After 30 min, a 7 M solution of ammonia in methanol (0.2 ml, 1.4 mmol) was added, and the resulting mixture was stirred at rt for further 30 min. The mixture was then directly separated by preparative RP-HPLC (Reprosil C18, gradient 20-40% acetonitrile/0.2% aq. trifluoroacetic acid). The product fractions were combined and then alkalized by addition of sat. aq. sodium bicarbonate solution. The solution was extracted with ethyl acetate, and the organic phase was washed with brine, dried over magnesium sulfate and evaporated to yield 30 mg of the title compound (61% of th.).

LC-MS (method 2): $R_t$=0.80 min; MS (ESIpos): m/z=354 (M+H)$^+$ $^1$H-NMR (400 MHz, DMSO-d$_6$): δ=8.18 (s, 1H), 7.95-8.15 (br. s, 1H), 7.97 (s, 1H), 7.38-7.43 (br. s, 1H), 7.36 (s, 1H), 7.29 (s, 1H), 7.16-7.21 (br. s, 1H), 6.84 (s, 1H), 5.4-5.6 (br. s, 1H), 3.95 (s, 3H), 2.45 (s, 3H) ppm.

Example 36

4-Amino-5-(7-methoxy-5-methyl-1-benzothiophen-2-yl)-N,N-dimethylpyrrolo[2,1-f][1,2,4]triazine-6-carboxamide

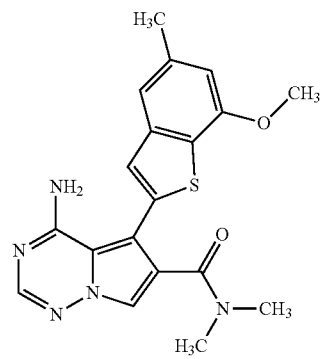 [SMILES: COc1cc(C)cc2cc(-c3c(C(=O)N(C)C)cn4ncnc(N)c34)sc12]

A stirred solution of Example 34 (90% purity, 58 mg, 148 μmol) in DMF (3 ml) was treated at rt with TBTU (58 mg, 180 μmol) and DIPEA (57 μl, 327 μmol). After 30 min, a 2 M solution of dimethylamine in THF (16 μl, 32 μmol) was added, and the resulting mixture was stirred at rt for 1 h. The mixture was then directly separated by preparative RP-HPLC (Reprosil C18, gradient 30-50% acetonitrile/0.2% aq. trifluoroacetic acid). The product fractions were combined, and acetonitrile was evaporated under reduced pressure. The product crystallized from the remaining aqueous solution over night. The crystals were filtered off and dried under high vacuum to yield 10 mg (16% of th.) of the title compound. The filtrate was alkalized by addition of sat. aq. sodium bicarbonate solution. The solution was extracted with ethyl acetate, and the organic phase was washed with brine, dried over magnesium sulfate and evaporated to yield a second batch of 8.6 mg (15% of th.) of the title compound.

LC-MS (method 2): $R_t$=0.86 min; MS (ESIpos): m/z=382 (M+H)$^+$ $^1$H-NMR (400 MHz, DMSO-d$_6$): δ=7.9-8.2 (br, 1H), 7.98 (s, 1H), 7.94 (s, 1H), 7.33 (s, 1H), 7.30 (s, 1H), 6.83 (s, 1H), 5.85-6.15 (br, 1H), 3.95 (s, 3H), 2.86 (s, 3H), 2.78 (s, 3H), 2.44 (s, 3H) ppm.

Example 37

4-Amino-N-ethyl-5-(7-methoxy-5-methyl-1-benzothiophen-2-yl)pyrrolo[2,1-f][1,2,4]triazine-6-carboxamide

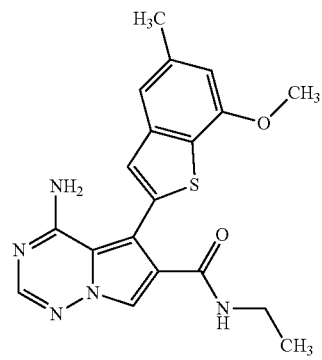 [SMILES: CCNC(=O)c1cn2ncnc(N)c2c1-c1cc2cc(C)cc(OC)c2s1]

A stirred solution of Example 34 (90% purity, 58 mg, 148 μmol) in DMF (3 ml) was treated at rt with TBTU (58 mg, 180 μmol) and DIPEA (57 μl, 327 μmol). After 30 min, a 2 M solution of ethylamine in THF (16 μl, 32 μmol) was added, and the resulting mixture was stirred at rt for 1 h. The mixture was then directly separated by preparative RP-HPLC (Reprosil C18, gradient 30-50% acetonitrile/0.2% aq. trifluoroacetic acid). The product fractions were combined and then alkalized by addition of sat. aq. sodium bicarbonate solution. The solution was extracted with ethyl acetate, and the organic phase was washed with brine, dried over magnesium sulfate and evaporated to yield 18 mg of the title compound (32% of th.).

LC-MS (method 2): $R_t$=0.89 min; MS (ESIpos): m/z=382 (M+H)$^+$ $^1$H-NMR (400 MHz, DMSO-d$_6$): δ=7.9-8.2 (br, 1H), 8.14 (s, 1H), 8.02 (t, 1H), 7.97 (s, 1H), 7.35 (s, 1H), 7.29 (s, 1H), 6.84 (s, 1H), 5.45-5.65 (br, 1H), 3.95 (s, 3H), 3.09-3.18 (quin, 2H), 2.45 (s, 3H), 1.01 (t, 3H) ppm.

Example 38

[4-Amino-5-(7-methoxy-5-methyl-1-benzothiophen-2-yl)pyrrolo[2,1-f][1,2,4]triazin-6-yl](4-methylpiperazin-1-yl)methanone

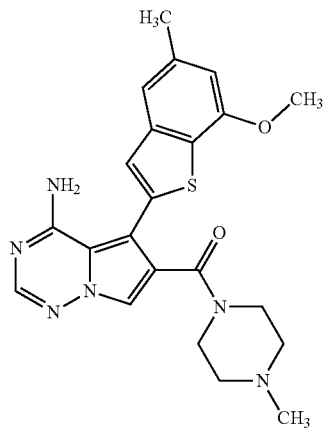 [SMILES: COc1cc(C)cc2cc(-c3c(C(=O)N4CCN(C)CC4)cn4ncnc(N)c34)sc12]

A stirred solution of Example 34 (90% purity, 58 mg, 148 μmol) in DMF (3 ml) was treated at rt with TBTU (58 mg, 180 μmol) and DIPEA (57 μl, 327 μmol). After 30 min, 1-methylpiperazine (36 μl, 33 μmol) was added, and the resulting mixture was stirred at rt for 1 h. The mixture was then directly separated by preparative RP-HPLC (Reprosil C18, gradient 10-30% acetonitrile/0.2% aq. trifluoroacetic acid). The product fractions were combined and then alkalized by addition of sat. aq. sodium bicarbonate solution. The solution was extracted with ethyl acetate, and the organic phase was washed with brine, dried over magnesium sulfate and evaporated to yield 26 mg of the title compound (40% of th.).

LC-MS (method 2): $R_t$=0.57 min; MS (ESIpos): m/z=437 (M+H)$^+$ $^1$H-NMR (400 MHz, DMSO-d$_6$): δ=7.95-8.15 (br, 1H), 7.98 (s, 1H), 7.94 (s, 1H), 7.32 (s, 1H), 7.31 (s, 1H), 6.84 (s, 1H), 5.95-6.20 (br, 1H), 3.95 (s, 3H), 3.43-3.52 (m, 1H), 3.11-3.18 (m, 1H), 2.44 (s, 3H), 2.09-2.18 (m, 1H), 1.95 (s, 3H), 1.80-1.90 (m, 1H), 1.40 (s, 4H) ppm.

Example 39

4-{[4-Amino-5-(7-methoxy-5-methyl-1-benzothiophen-2-yl)pyrrolo[2,1-f][1,2,4]triazin-6-yl]-carbonyl}piperazin-2-one

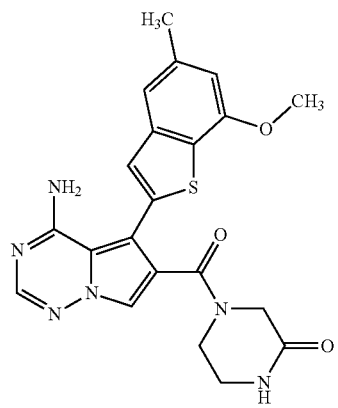 [SMILES: COc1cc(C)cc2cc(-c3c(C(=O)N4CCNC(=O)C4)cn4ncnc(N)c34)sc12]

A stirred solution of Example 34 (90% purity, 58 mg, 148 μmol) in DMF (3 ml) was treated at rt with TBTU (58 mg, 180 μmol) and DIPEA (57 μl, 327 μmol). After 30 min, 2-oxopiperazine (33 mg, 33 μmol) was added, and the resulting mixture was stirred at rt for 1 h. The mixture was then directly separated by preparative RP-HPLC (Reprosil C18, gradient 20-40% acetonitrile/0.2% aq. trifluoroacetic acid). The product fractions were combined and then alkalized by addition of sat. aq. sodium bicarbonate solution. The solution was extracted with ethyl acetate, and the organic phase was washed with brine, dried over magnesium sulfate and evaporated to yield 22 mg of the title compound (34% of th.).

LC-MS (method 2): $R_t$=0.69 min; MS (ESIpos): m/z=437 (M+H)$^+$ $^1$H-NMR (400 MHz, DMSO-d$_6$): inter al. δ=8.0-8.2 (br. s, 1H), 8.02 (s, 1H), 8.00 (s, 2H), 7.34 (s, 1H), 7.30 (s, 1H), 6.83 (s, 1H), 5.95-6.15 (br. s, 1H), 3.97 (br. s, 1H), 3.94 (s, 3H), 3.60-3.85 (br. m, 1H), 3.44 (br. s, 1H), 2.90-3.15 (br. m, 1H), 2.9 (br. s, 1H), 2.44 (s, 3H) ppm.

General Procedure for the Preparation of Examples 40-45 in Table I:

0.1 mmol of Intermediate 19A was treated with 5 eq. of the respective alcohol component and 7 eq. of DIPEA. The resulting mixture was shaken at 130° C. overnight. After cooling to room temperature, the reaction mixture was treated with 0.6 ml DMF, shaken overnight again and then filtered. The product was isolated from the filtrate by the purification method indicated.

TABLE I

| Example No. | Structure | Purification method | LC-MS data (method 7) |
|---|---|---|---|
| 40 | 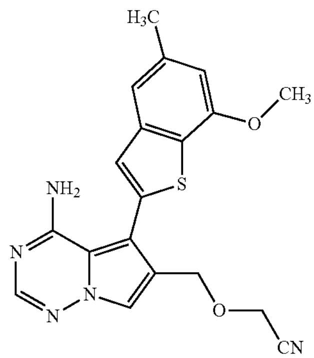 [SMILES: COc1cc(C)cc2cc(-c3c(COCC#N)cn4ncnc(N)c34)sc12] | PM2 | R$_t$ = 1.2 min; MS (ESIneg): m/z = 378 (M − H)$^-$ |
| 41 | 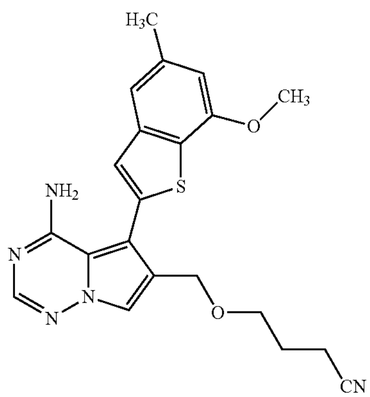 [SMILES: COc1cc(C)cc2cc(-c3c(COCCCC#N)cn4ncnc(N)c34)sc12] | PM2 | R$_t$ = 1.23 min; MS (ESIpos): m/z = 408 (M + H)$^+$ |
| 42 | 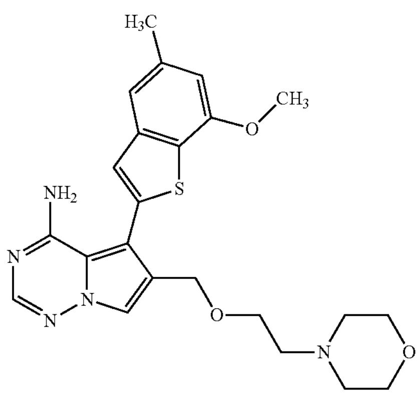 [SMILES: COc1cc(C)cc2cc(-c3c(COCCN4CCOCC4)cn4ncnc(N)c34)sc12] | PM2 | R$_t$ = 0.82 min; MS (ESIpos): m/z = 454 (M + H)$^+$ |
| 43 | 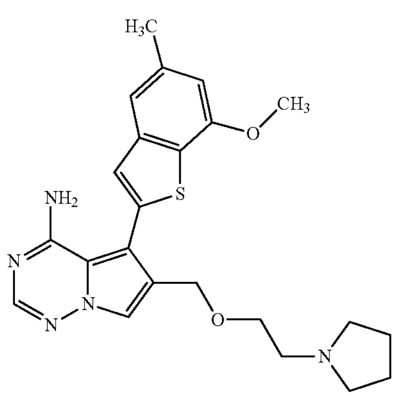 [SMILES: COc1cc(C)cc2cc(-c3c(COCCN4CCCC4)cn4ncnc(N)c34)sc12] | PM2 | R$_t$ = 0.79 min; MS (ESIpos): m/z = 438 (M + H)$^+$ |

TABLE I-continued

| Example No. | Structure | Purification method | LC-MS data (method 7) |
|---|---|---|---|
| 44 | 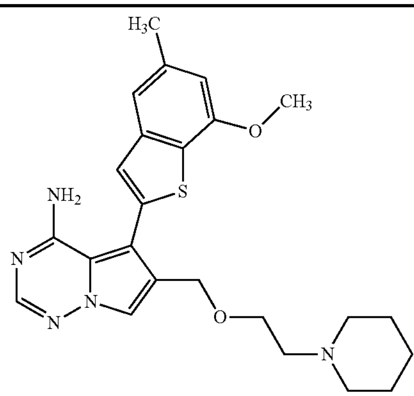 | PM2 | $R_t = 0.81$ min; MS (ESIpos): m/z = 452 (M + H)$^+$ |
| 45 | 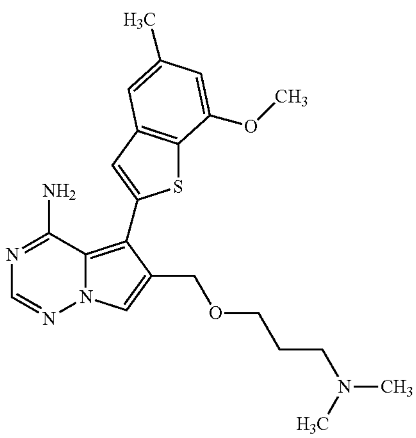 [SMILES: COc1cc(C)cc2cc(-c3c(COCCCN(C)C)cn4ncnc(N)c34)sc12] | PM1 | $R_t = 0.76$ min; MS (ESIpos): m/z = 426 (M + H)$^+$ |

General Procedure for the Preparation of Examples 46-76 in Table II:

1.5 mmol of the respective amine component was treated with a solution of 0.1 mmol of Intermediate 19A in THF followed by 4 eq. of DIPEA. The resulting mixture was shaken at room temperature overnight. Then, the solvent was removed in vacuo, and the residue was treated with DMF and filtered. The product was isolated from the filtrate by the purification method indicated.

TABLE II

| Example No. | Structure | Purification method | LC-MS data (method 7) |
|---|---|---|---|
| 46 | 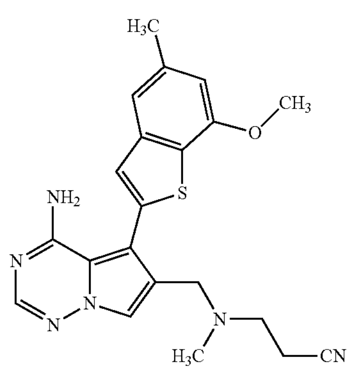 [SMILES: COc1cc(C)cc2cc(-c3c(CN(C)CCC#N)cn4ncnc(N)c34)sc12] | PM2 | $R_t = 0.82$ min; MS (ESIpos): m/z = 406 (M + H)$^+$ |

TABLE II-continued
| Example No. | Structure | Purification method | LC-MS data (method 7) |
|---|---|---|---|
| 47 | 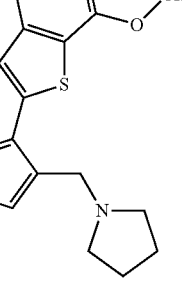 | PM2 | $R_t$ = 0.81 min; MS (ESIpos): m/z = 394 (M + H)$^+$ |
| 48 | 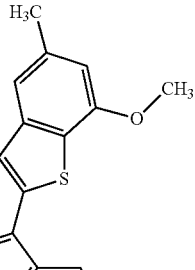 | PM2 | $R_t$ = 0.79 min; MS (ESIpos): m/z = 380 (M + H)$^+$ |
| 49 | 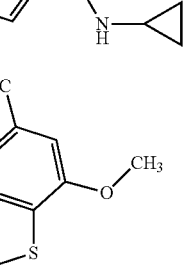 | PM2 | $R_t$ = 0.85 min; MS (ESIpos): m/z = 440 (M + H)$^+$ |
| 50 | 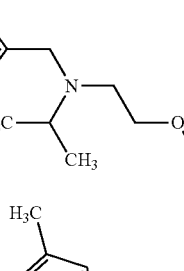 | PM2 | $R_t$ = 0.79 min; MS (ESIpos): m/z = 423 (M + H)$^+$ |

TABLE II-continued

| Example No. | Structure | Purification method | LC-MS data (method 7) |
|---|---|---|---|
| 51 | 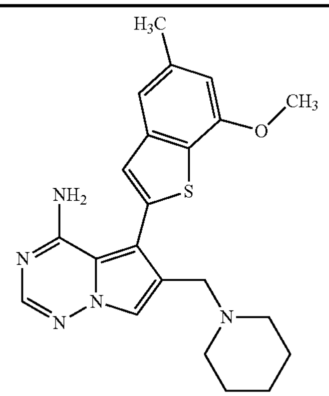 | PM2 | $R_t$ = 0.83 min; MS (ESIpos): m/z = 408 (M + H)$^+$ |
| 52 | 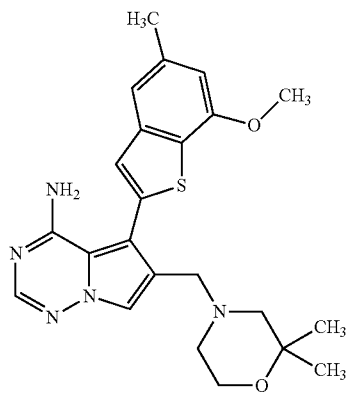 [SMILES: COc1cc(C)cc2cc(-c3c(CN4CCOC(C)(C)C4)cn4ncnc(N)c34)sc12] | PM2 | $R_t$ = 0.85 min; MS (ESIpos): m/z = 438 (M + H)$^+$ |
| 53 | 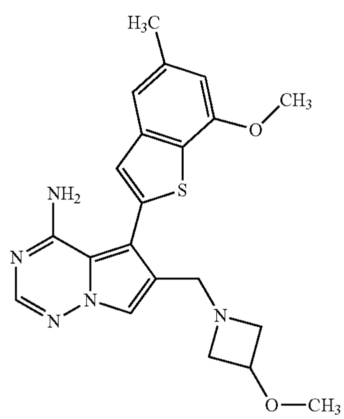 [SMILES: COc1cc(C)cc2cc(-c3c(CN4CC(OC)C4)cn4ncnc(N)c34)sc12] | PM2 | $R_t$ = 1.05 min; MS (ESIpos): m/z = 410 (M + H)$^+$ |
| 54 | 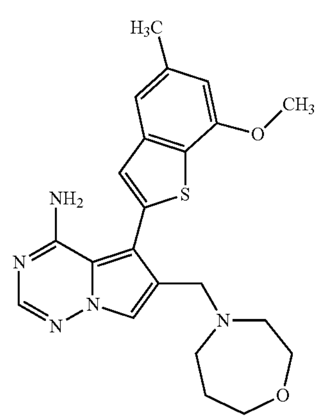 [SMILES: COc1cc(C)cc2cc(-c3c(CN4CCCOCC4)cn4ncnc(N)c34)sc12] | PM2 | $R_t$ = 0.79 min; MS (ESIpos): m/z = 424 (M + H)$^+$ |

TABLE II-continued

| Example No. | Structure | Purification method | LC-MS data (method 7) |
|---|---|---|---|
| 55 | 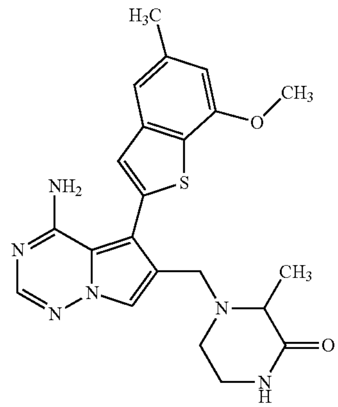 [SMILES: COc1cc(C)cc2cc(-c3c(CN4CCNC(=O)C4C)cn4ncnc(N)c34)sc12] | PM2 | $R_t$ = 0.90 min; MS (ESIpos): m/z = 437 (M + H)⁺ |
| 56 | 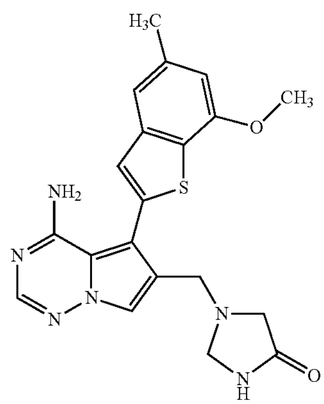 [SMILES: COc1cc(C)cc2cc(-c3c(CN4CNC(=O)C4)cn4ncnc(N)c34)sc12] | PM2 | $R_t$ = 1.01 min; MS (ESIpos): m/z = 409 (M + H)⁺ |
| 57 | 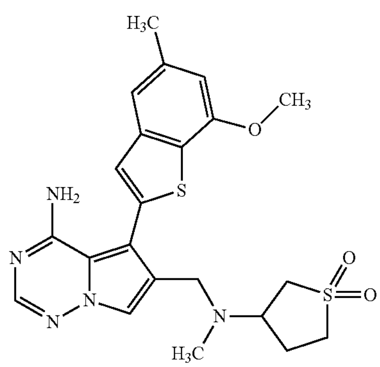 [SMILES: COc1cc(C)cc2cc(-c3c(CN(C)C4CCS(=O)(=O)C4)cn4ncnc(N)c34)sc12] | PM2 | $R_t$ = 0.92 min; MS (ESIpos): m/z = 472 (M + H)⁺ |

TABLE II-continued
| Example No. | Structure | Purification method | LC-MS data (method 7) |
|---|---|---|---|
| 58 | 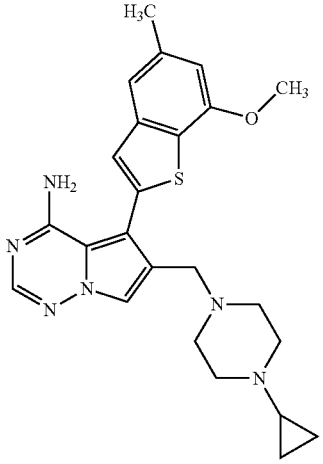 [SMILES: COc1cc(C)cc2cc(-c3c(CN4CCN(C5CC5)CC4)cn4ncnc(N)c34)sc12] | PM2 | $R_t$ = 0.84 min; MS (ESIpos): m/z = 449 (M + H)$^+$ |
| 59 | 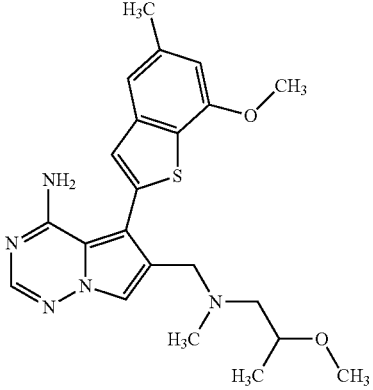 [SMILES: COc1cc(C)cc2cc(-c3c(CN(C)CC(C)OC)cn4ncnc(N)c34)sc12] | PM2 | $R_t$ = 0.84 min; MS (ESIpos): m/z = 426 (M + H)$^+$ |
| 60 | 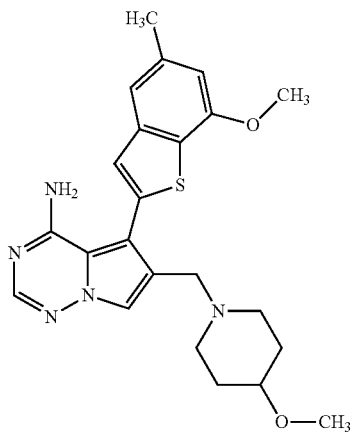 [SMILES: COc1cc(C)cc2cc(-c3c(CN4CCC(OC)CC4)cn4ncnc(N)c34)sc12] | PM2 | $R_t$ = 0.82 min; MS (ESIpos): m/z = 438 (M + H)$^+$ |

TABLE II-continued

| Example No. | Structure | Purification method | LC-MS data (method 7) |
|---|---|---|---|
| 61 | 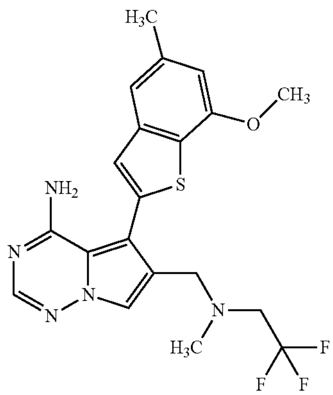 [SMILES: COc1cc(C)cc2cc(-c3c(CN(C)CC(F)(F)F)cn4ncnc(N)c34)sc12] | PM2 | $R_t$ = 1.36 min; MS (ESIpos): m/z = 436 (M + H)$^+$ |
| 62 | 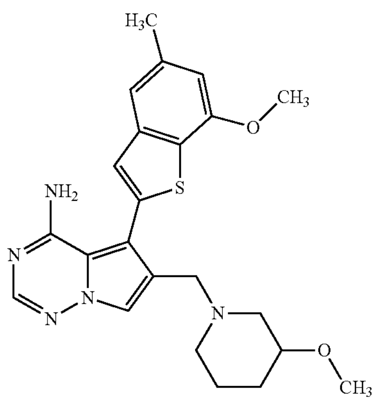 [SMILES: COc1cc(C)cc2cc(-c3c(CN4CCCC(OC)C4)cn4ncnc(N)c34)sc12] | PM2 | $R_t$ = 0.83 min; MS (ESIpos): m/z = 438 (M + H)$^+$ |
| 63 | 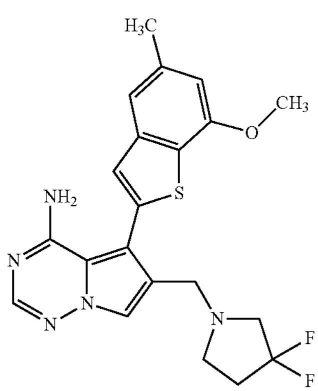 [SMILES: COc1cc(C)cc2cc(-c3c(CN4CCC(F)(F)C4)cn4ncnc(N)c34)sc12] | PM2 | $R_t$ = 1.03 min; MS (ESIpos): m/z = 430 (M + H)$^+$ |

TABLE II-continued

| Example No. | Structure | Purification method | LC-MS data (method 7) |
|---|---|---|---|
| 64 | 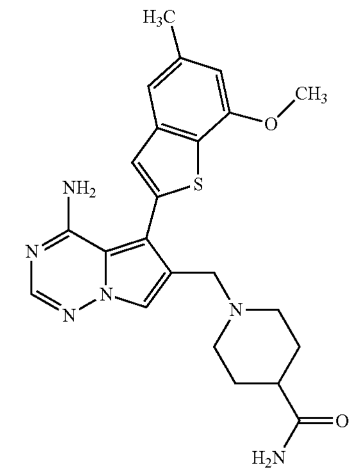 [SMILES: COc1cc(C)cc2cc(-c3c(CN4CCC(C(N)=O)CC4)cn4ncnc(N)c34)sc12] | PM2 | R$_t$ = 0.76 min; MS (ESIpos): m/z = 451 (M + H)$^+$ |
| 65 | 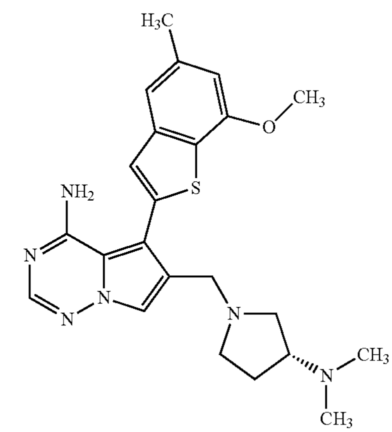 [SMILES: COc1cc(C)cc2cc(-c3c(CN4CC[C@@H](N(C)C)C4)cn4ncnc(N)c34)sc12] | PM2 | R$_t$ = 0.69 min; MS (ESIpos): m/z = 437 (M + H)$^+$ |
| 66 | 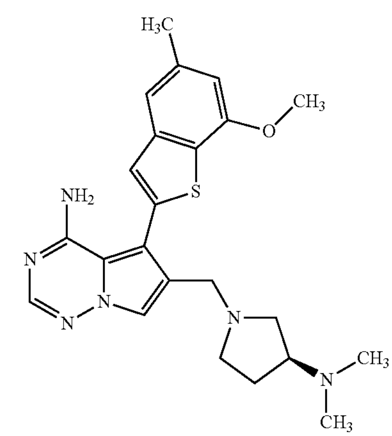 [SMILES: COc1cc(C)cc2cc(-c3c(CN4CC[C@H](N(C)C)C4)cn4ncnc(N)c34)sc12] | PM2 | R$_t$ = 0.69 min; MS (ESIpos): m/z = 437 (M + H)$^+$ |

TABLE II-continued

| Example No. | Structure | Purification method | LC-MS data (method 7) |
|---|---|---|---|
| 67 | 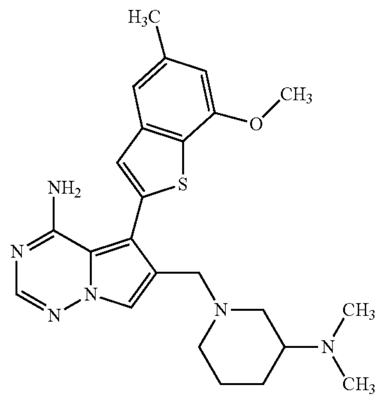 [SMILES: COc1cc(C)cc2cc(-c3c(CN4CCCC(N(C)C)C4)cn4ncnc(N)c34)sc12] | PM2 | $R_t$ = 0.71 min; MS (ESIpos): m/z = 451 (M + H)$^+$ |
| 68 | 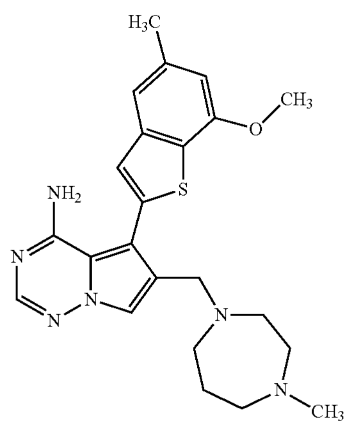 [SMILES: COc1cc(C)cc2cc(-c3c(CN4CCCN(C)CC4)cn4ncnc(N)c34)sc12] | PM2 | $R_t$ = 0.71 min; MS (ESIpos): m/z = 437 (M + H)$^+$ |
| 69 | 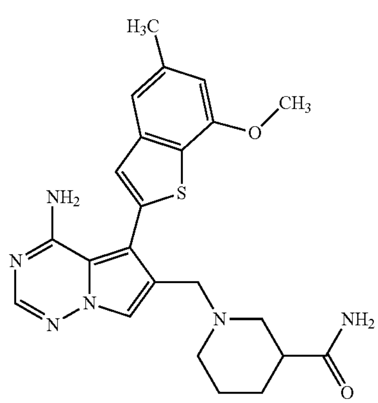 [SMILES: COc1cc(C)cc2cc(-c3c(CN4CCCC(C(N)=O)C4)cn4ncnc(N)c34)sc12] | PM2 | $R_t$ = 0.77 min; MS (ESIpos): m/z = 451 (M + H)$^+$ |

TABLE II-continued

| Example No. | Structure | Purification method | LC-MS data (method 7) |
|---|---|---|---|
| 70 | 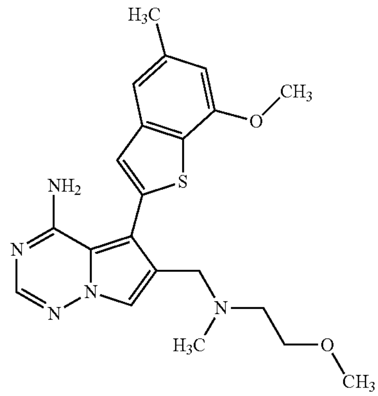 [SMILES: COCCN(C)Cc1cn2ncnc(N)c2c1-c1cc2cc(C)cc(OC)c2s1] | PM2 | R$_t$ = 0.81 min; MS (ESIpos): m/z = 412 (M + H)$^+$ |
| 71 | 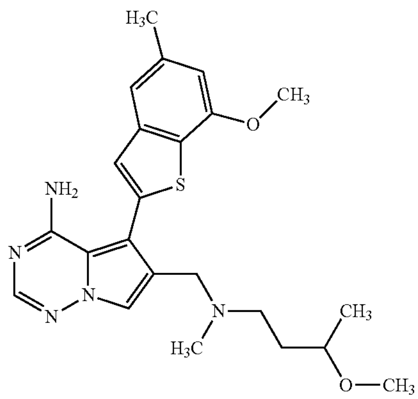 | PM2 | R$_t$ = 0.84 min; MS (ESIpos): m/z = 426 (M + H)$^+$ |
| 72 | 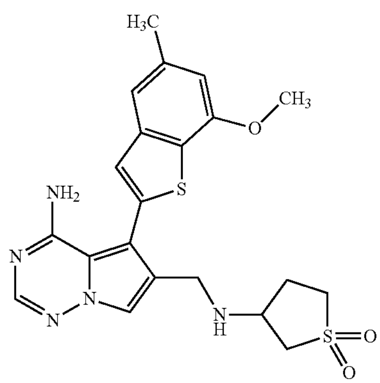 [SMILES: COc1cc(C)cc2cc(-c3c(CNC4CCS(=O)(=O)C4)cn4ncnc(N)c34)sc12] | PM2 | R$_t$ = 0.80 min; MS (ESIpos): m/z = 458 (M + H)$^+$ |
| 73 | 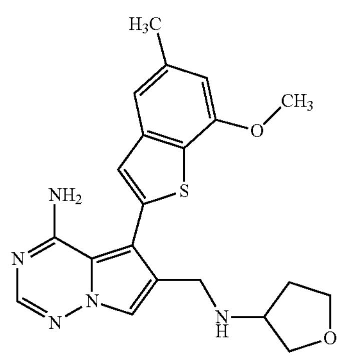 [SMILES: COc1cc(C)cc2cc(-c3c(CNC4CCOC4)cn4ncnc(N)c34)sc12] | PM2 | R$_t$ = 0.77 min; MS (ESIpos): m/z = 410 (M + H)$^+$ |

TABLE II-continued

| Example No. | Structure | Purification method | LC-MS data (method 7) |
|---|---|---|---|
| 74 | 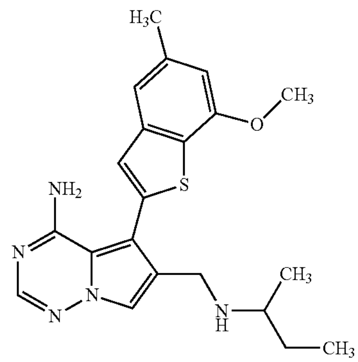 [SMILES: CCC(C)NCc1cn2ncnc(N)c2c1-c1cc2cc(C)cc(OC)c2s1] | PM2 | $R_t$ = 0.83 min; MS (ESIpos): m/z = 396 (M + H)$^+$ |
| 75 | 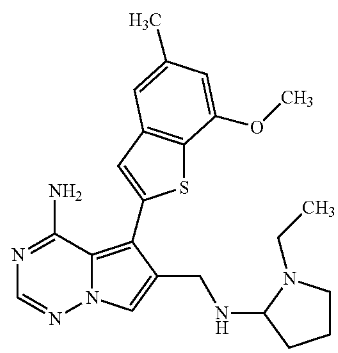 | PM2 | $R_t$ = 0.70 min; MS (ESIpos): m/z = 451 (M + H)$^+$ |
| 76 | 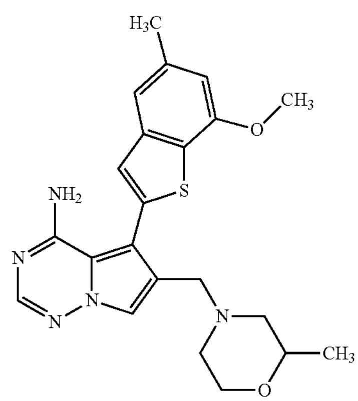 [SMILES: COc1cc(C)cc2cc(-c3c(CN4CCOC(C)C4)cn4ncnc(N)c34)sc12] | PM2 | $R_t$ = 0.81 min; MS (ESIpos): m/z = 424 (M + H)$^+$ |
| 77 | 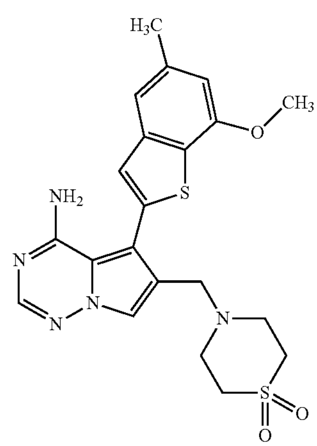 [SMILES: COc1cc(C)cc2cc(-c3c(CN4CCS(=O)(=O)CC4)cn4ncnc(N)c34)sc12] | PM2 | $R_t$ = 1.14 min; MS (ESIpos): m/z = 458 (M + H)$^+$ |

B. EVALUATION OF BIOLOGICAL ACTIVITY

Abbreviations and Acronyms

Ahx 6-aminohexanoic acid
ATP adenosine triphosphate
BSA bovine serum albumin
CREB cAMP-response element-binding protein
DMSO dimethylsulfoxide
EDTA ethylenediaminetetraacetic acid
EGTA ethyleneglycol-bis(2-aminoethylether)-N,N,N',N'-tetraacetic acid
FBS fetal bovine serum
FGF fibroblast growth factor
FGFR fibroblast growth factor receptor
GFP green fluorescent protein
GST glutathione S-transferase
HEPES 4-(2-hydroxyethyl)piperazine-1-ethansulfonic acid
HRTF homogeneous time-resolved fluorescence
MOPS 3-(N-morpholino)propanesulfonic acid
mTOR mammalian target of Rapamycin
PBS phosphate buffered saline
PI3K phosphatidylinositol 3-kinase
RTK receptor tyrosine kinase
SNP single nucleotide polymorphism
TR-FRET time-resolved fluorescence resonance energy transfer
VEGF vascular endothelial growth factor
VEGFR vascular endothelial growth factor receptor Demonstration of the activity of the compounds of the present invention may be accomplished through in vitro, ex vivo, and in vivo assays that are well known in the art. For example, to demonstrate the activity of the compounds of the present invention, the following assays may be used.

B-1. FGFR-1 High ATP Kinase Assay

FGFR-1 inhibitory activity at high ATP concentration of the compounds of the present invention after their pre-incubation with FGFR-1 was quantified employing the TR-FRET based FGFR-1 high ATP assay as described in the following paragraphs:

A recombinant tagged FGFR-1 fusion protein [fusion of glutathione-S-transferase (GST) (N-terminally), His6-tag, thrombin cleavage site, and the intracellular part of human FGFR-1 from amino acids G400 to R800 as in GenBank entry NM_015850], expressed in SF9 insect cells using baculovirus expression system and purified via glutathione-agarose affinity chromatography, was purchased from Proqinase (product no. 0101-0000-1) and used as enzyme. As substrate for the kinase reaction, the biotinylated peptide biotin-Ahx-AAEEEYFFLFAKKK (C-terminus in amide form) was used which can be purchased, e.g., from Biosyntan (Berlin-Buch, Germany).

Usually, test compounds were tested on the same microtiter plate at 11 different concentrations in the range of 20 μM to 0.1 nM (e.g. 20 μM, 5.9 μM, 1.7 μM, 0.51 μM, 0.15 μM, 44 nM, 13 nM, 3.8 nM, 1.1 nM, 0.33 nM, and 0.1 nM) in duplicates for each concentration. The dilution series was prepared separately prior to the assay as 100-fold concentrated stock solutions in DMSO; exact concentrations could vary depending on the pipettor used. For the assay, 50 nl of each stock solution of the test compound in DMSO was pipetted into a black, low-volume 384-well microtiter plate (Greiner Bio-One, Frickenhausen, Germany). 2 μl of a solution of the above FGFR-1 fusion protein in aqueous assay buffer [8 mM MOPS pH 7.0, 10 mM magnesium acetate, 1.0 mM dithiothreitol, 0.05% (w/v) bovine serum albumin (BSA), 0.07% (v/v) Tween-20, 0.2 mM EDTA] was added, and the mixture was incubated for 15 min at 22° C. to allow pre-binding of the test compound to the enzyme. Then, the kinase reaction was started by the addition of 3 μl of a solution of adenosine triphosphate (ATP, 3.3 mM; final concentration in the 5 μl assay volume=2 mM) and substrate (0.16 μM; final concentration in the 5 μl assay volume=0.1 μM) in assay buffer, and the resulting mixture was incubated for a reaction time of 15 min at 22° C. The concentration of FGFR-1 fusion protein was adjusted depending on the activity of the enzyme lot and was chosen appropriately to have the assay in the linear range (typical concentrations were in the range of 0.05 μg/ml). The reaction was stopped by the addition of 5 μl of a solution of HTRF detection reagents [25 nM streptavidin-XL665 (Cis Biointernational) and 1 nM PT66-Eu-chelate, an europium-chelate labelled anti-phosphotyrosine antibody (Perkin-Elmer; PT66-Tb-cryptate from Cis Biointernational may be used instead), in an aqueous EDTA solution (50 mM EDTA, 0.1% (w/v) BSA in 50 mM HEPES/NaOH pH 7.5)].

The resulting mixture was incubated for 1 h at 22° C. to allow formation of the complex between the phosphorylated biotinylated peptide and the detection reagents. Subsequently, the amount of phosphorylated substrate was evaluated by measurement of the resonance energy transfer from the Eu-chelate to the streptavidin-XL665. For this, the fluorescence emissions at 620 nm and 665 nm after excitation at 350 nm were measured in a TR-FRET reader [e.g. Rubystar (BMG Labtechnologies, Offenburg, Germany) or Viewlux (Perkin-Elmer)]. The ratio of the emissions at 665 nm and at 620 nm was taken as the measure for the amount of phosphorylated substrate. Data were normalised (enzyme reaction without inhibitor=0% inhibition, all other assay components but no enzyme=100% inhibition), and $IC_{50}$ values were calculated by a 4-parameter fit using an in-house software.

$IC_{50}$ values for individual compounds of the invention from this assay are listed in Table 1A below:

TABLE 1A

| Example No. | FGFR-1 (high ATP) $IC_{50}$ [nM] |
|---|---|
| 1 | 10.0 |
| 2 | 1.3 |
| 3 | 1.8 |
| 4 | 38.4 |
| 5 | 75.1 |
| 6 | 4.0 |
| 7 | 9.4 |
| 8 | 0.2 |
| 9 | 0.7 |
| 10 | 1.0 |
| 11 | 1.1 |
| 12 | 40.0 |
| 13 | 47.6 |
| 14 | 2.2 |
| 15 | 50.3 |
| 16 | 4.1 |
| 17 | 2.0 |
| 18 | 1.6 |
| 19 | 13.8 |
| 20 | 19.9 |
| 21 | 7.3 |
| 22 | 10.6 |
| 23 | 5.6 |
| 24 | 11.6 |
| 25 | 0.6 |
| 26 | 2.0 |
| 27 | 0.9 |
| 28 | 5.6 |
| 29 | 24.3 |

TABLE 1A-continued

| Example No. | FGFR-1 (high ATP) IC$_{50}$ [nM] |
|---|---|
| 30 | 5.5 |
| 31 | 0.6 |
| 32 | 22.2 |
| 33 | 2.7 |
| 34 | 20.5 |
| 35 | 4.8 |
| 36 | 37.5 |
| 37 | 7.5 |
| 38 | 4.4 |
| 39 | 51.7 |
| 40 | 14.7 |
| 41 | 22.1 |
| 42 | 40.8 |
| 43 | 14.2 |
| 44 | 15.1 |
| 45 | 29.4 |
| 46 | 2.5 |
| 47 | 1.7 |
| 48 | 6.3 |
| 49 | 17.3 |
| 50 | 0.3 |
| 51 | 1.4 |
| 52 | 7.9 |
| 53 | 29.0 |
| 54 | 4.6 |
| 55 | 2.7 |
| 56 | 7.8 |
| 57 | 4.2 |
| 58 | 7.3 |
| 59 | 17.9 |
| 60 | 32.1 |
| 61 | 32.1 |
| 62 | 3.9 |
| 63 | 6.5 |
| 64 | 1.6 |
| 65 | 0.7 |
| 66 | 1.0 |
| 67 | 0.9 |
| 68 | 1.5 |
| 69 | 5.7 |
| 70 | 16.4 |
| 71 | 25.0 |
| 72 | 14.0 |
| 73 | 14.3 |
| 74 | 33.8 |
| 75 | 14.7 |
| 76 | 7.0 |
| 77 | 35.1 |

Selected 8-amino-1-(benzothiophen-2-yl)imidazo[1,5-a]pyrazine derivatives and related compounds which were regarded to be representative of closest prior art (see Int. Pat. Appl. WO 2007/061737-A2 and example compounds described therein) were synthesized following the published procedures and also tested in the FGFR-1 high ATP assay for comparative purposes. IC$_{50}$ values that were obtained for these compounds are listed in Table 1B below:

TABLE 1B

| Structure of comparative compound | Example No. in WO 2007/061737 | FGFR-1 (high ATP) IC$_{50}$ [nM] |
|---|---|---|
| | 4 | 12000 |
| | 5 | 500 |
| | 120 | 985 |
| | 205 | 20000 |

TABLE 1B-continued

| Structure of comparative compound | Example No. in WO 2007/061737 | FGFR-1 (high ATP) IC$_{50}$ [nM] |
|---|---|---|
| 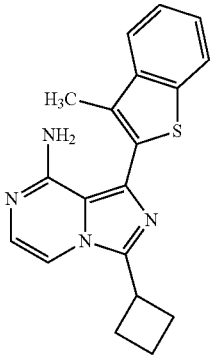 [SMILES: Cc1c(-c2nc(C3CCC3)n3ccnc(N)c23)sc2ccccc12] | 210 | 456 |
| 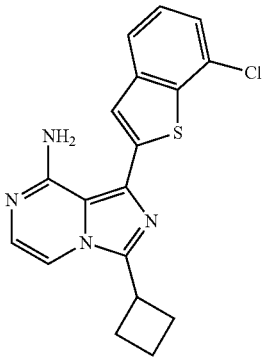 [SMILES: Nc1nccn2c(C3CCC3)nc(-c3cc4cccc(Cl)c4s3)c12] | 233 | 4600 |

The IC$_{50}$ values specified in Table 1A and 1B demonstrate that the compounds of the present invention are about one to three orders of magnitude more potent in inhibiting FGFR-1 kinase activity than the selected prior art compounds.

B-2. FGFR-3 Kinase Assay

FGFR-3 inhibitory activity of the compounds of the present invention after their pre-incubation with FGFR-3 was quantified employing the TR-FRET based FGFR-3 assay as described in the following paragraphs:

A recombinant tagged FGFR-3 fusion protein [fusion of glutathione-S-transferase (GST) (N-terminally), His6-tag, thrombin cleavage site, and the intracellular part of human FGFR-3 from amino acids R397 to T806 as in NCBI/Protein entry NP_000133.1], expressed in SF9 insect cells using baculovirus expression system and purified via glutathione-S-transferase affinity chromatography, was purchased from Proqinase (product no. 1068-0000-1) and used as enzyme. As substrate for the kinase reaction, the biotinylated peptide biotin-Ahx-AAEEEYFFLFAKKK (C-terminus in amide form) was used which can be purchased, e.g., from Biosyntan (Berlin-Buch, Germany).

Usually, test compounds were tested on the same microtiter plate at 11 different concentrations in the range of 20 μM to 0.1 nM (e.g. 20 μM, 5.9 μM, 1.7 μM, 0.51 μM, 0.15 μM, 44 nM, 13 nM, 3.8 nM, 1.1 nM, 0.33 nM, and 0.1 nM) in duplicates for each concentration. The dilution series was prepared separately prior to the assay as 100-fold concentrated stock solutions in DMSO; exact concentrations could vary depending on the pipettor used. For the assay, 50 nl of each stock solution of the test compound in DMSO was pipetted into a black, low-volume 384-well microtiter plate (Greiner Bio-One, Frickenhausen, Germany). 2 μl of a solution of the above FGFR-3 fusion protein in aqueous assay buffer [8 mM MOPS pH 7.0, 10 mM magnesium acetate, 1.0 mM dithiothreitol, 0.05% (w/v) bovine serum albumin (BSA), 0.07% (v/v) Tween-20, 0.2 mM EDTA] was added, and the mixture was incubated for 15 min at 22° C. to allow pre-binding of the test compound to the enzyme. Then, the kinase reaction was started by the addition of 3 μl of a solution of adenosine triphosphate (ATP, 16.7 μM; final concentration in the 5 μl assay volume=10 μM) and substrate (0.8 μM; final concentration in the 5 μl assay volume=0.5 μM) in assay buffer, and the resulting mixture was incubated for a reaction time of 60 min at 22° C. The concentration of FGFR-3 fusion protein was adjusted depending on the activity of the enzyme lot and was chosen appropriately to have the assay in the linear range (typical concentrations were in the range of 0.03 μg/ml). The reaction was stopped by the addition of 5 μl of a solution of HTRF detection reagents [100 nM streptavidin-XL665 (Cis Biointernational) and 1 nM PT66-Tb-cryptate, a terbium-cryptate labelled anti-phosphotyrosine antibody (Cis Biointernational; PT66-Eu-chelate from Perkin-Elmer may be used instead), in an aqueous EDTA solution (50 mM EDTA, 0.1% (w/v) BSA in 50 mM HEPES/NaOH pH 7.5)].

The resulting mixture was incubated for 1 h at 22° C. to allow formation of the complex between the phosphorylated biotinylated peptide and the detection reagents. Subsequently, the amount of phosphorylated substrate was evaluated by measurement of the resonance energy transfer from the Tb-chelate to the streptavidin-XL665. For this, the fluorescence emissions at 620 nm and 665 nm after excitation at 350 nm were measured in a TR-FRET reader [e.g. Rubystar (BMG Labtechnologies, Offenburg, Germany) or Viewlux (Perkin-Elmer)]. The ratio of the emissions at 665 nm and at 620 nm was taken as the measure for the amount of phosphorylated substrate. Data were normalised (enzyme reaction without inhibitor=0% inhibition, all other assay components but no enzyme=100% inhibition), and IC$_{50}$ values were calculated by a 4-parameter fit using an in-house software.

IC$_{50}$ values for individual compounds of the invention from this assay are listed in Table 2A below:

TABLE 2A

| Example No. | FGFR-3 IC$_{50}$ [nM] |
|---|---|
| 1 | 18.2 |
| 2 | 2.2 |
| 3 | 4.2 |
| 4 | 49.9 |
| 5 | 72.4 |
| 6 | 4.4 |
| 7 | 5.8 |
| 8 | 0.2 |
| 9 | 0.2 |
| 10 | 1.4 |
| 11 | 0.4 |
| 12 | 11.6 |
| 13 | 15.1 |
| 14 | 0.8 |
| 15 | 87.1 |
| 16 | 2.3 |
| 17 | 1.8 |
| 18 | 1.3 |
| 19 | 11.2 |
| 20 | 15.2 |
| 21 | 27.9 |
| 22 | 10.8 |
| 23 | 17.4 |
| 24 | 8.7 |
| 25 | 0.4 |

TABLE 2A-continued

| Example No. | FGFR-3 IC$_{50}$ [nM] |
| --- | --- |
| 26 | 2.0 |
| 27 | 0.5 |
| 28 | 14.2 |
| 29 | 18.7 |
| 30 | 3.1 |
| 31 | 0.3 |
| 33 | 1.8 |
| 40 | 9.1 |
| 41 | 12.7 |
| 42 | 30.0 |
| 43 | 10.7 |
| 44 | 9.3 |
| 45 | 24.8 |
| 46 | 1.2 |
| 47 | 1.0 |
| 48 | 3.6 |
| 49 | 14.2 |
| 50 | 0.1 |
| 51 | 0.7 |
| 52 | 3.8 |
| 53 | 15.1 |
| 54 | 2.3 |
| 55 | 1.4 |
| 56 | 3.1 |
| 57 | 3.0 |
| 58 | 6.2 |
| 59 | 4.0 |
| 60 | 12.5 |
| 61 | 14.6 |
| 62 | 2.6 |
| 63 | 3.0 |
| 64 | 1.1 |
| 65 | 0.6 |
| 66 | 0.5 |
| 67 | 0.6 |
| 68 | 0.8 |
| 69 | 4.4 |
| 70 | 7.4 |
| 71 | 2.5 |
| 72 | 5.5 |
| 73 | 2.3 |
| 74 | 5.0 |
| 75 | 5.0 |
| 76 | 4.9 |
| 77 | 15.3 |

Selected 8-amino-1-(benzothiophen-2-yl)imidazo[1,5-a]pyrazine derivatives and related compounds which were regarded to be representative of closest prior art (see Int. Pat. Appl. WO 2007/061737-A2 and example compounds described therein) were synthesized following the published procedures and also tested in the FGFR-3 assay for comparative purposes. IC$_{50}$ values that were obtained for these compounds are listed in Table 2B below:

TABLE 2B

| Structure of comparative compound | Example No. in WO 2007/061737 | FGFR-3 IC$_{50}$ [nM] |
| --- | --- | --- |
| | 4 | 2400 |
| | 5 | 250 |
| | 120 | 506 |
| | 205 | 20000 |

TABLE 2B-continued

| Structure of comparative compound | Example No. in WO 2007/061737 | FGFR-3 IC$_{50}$ [nM] |
|---|---|---|
| (structure shown) | 210 | 554 |
| (structure shown) | 233 | 10000 |

The IC$_{50}$ values specified in Table 2A and 2B demonstrate that the compounds of the present invention are about three to a thousand times more potent in inhibiting FGFR-3 kinase activity than the selected prior art compounds.

B-3. FGFR-4 High ATP Kinase Assay

FGFR-4 inhibitory activity at high ATP concentration of the compounds of the present invention after their pre-incubation with FGFR-4 was quantified employing the TR-FRET based FGFR-4 high ATP assay as described in the following paragraphs:

A recombinant tagged FGFR-4 fusion protein [fusion of glutathione-S-transferase (GST) (N-terminally), His6-tag, thrombin cleavage site, and the intracellular part of human FGFR-4 from amino acids R391 to T802 as in GenBank entry NM_002011], expressed in SF9 insect cells using baculovirus expression system and purified via glutathione-agarose affinity chromatography, was purchased from Proqinase (product no. 0127-0000-3) and used as enzyme. As substrate for the kinase reaction, the biotinylated peptide biotin-Ahx-AAEEEYFFLFAKKK (C-terminus in amide form) was used which can be purchased, e.g., from Biosyntan (Berlin-Buch, Germany).

Usually, test compounds were tested on the same microtiter plate at 11 different concentrations in the range of 20 μM to 0.1 nM (e.g. 20 μM, 5.9 μM, 1.7 μM, 0.51 μM, 0.15 μM, 44 nM, 13 nM, 3.8 nM, 1.1 nM, 0.33 nM, and 0.1 nM) in duplicates for each concentration. The dilution series was prepared separately prior to the assay as 100-fold concentrated stock solutions in DMSO; exact concentrations could vary depending on the pipettor used. For the assay, 50 nl of each stock solution of the test compound in DMSO was pipetted into a black, low-volume 384-well microtiter plate (Greiner Bio-One, Frickenhausen, Germany). 2 μl of a solution of the above FGFR-4 fusion protein in aqueous assay buffer [8 mM MOPS pH 7.0, 10 mM magnesium acetate, 1.0 mM dithiothreitol, 0.05% (w/v) bovine serum albumin (BSA), 0.07% (v/v) Tween-20, 0.2 mM EDTA] was added, and the mixture was incubated for 15 min at 22° C. to allow pre-binding of the test compound to the enzyme. Then, the kinase reaction was started by the addition of 3 μl of a solution of adenosine triphosphate (ATP, 3.3 mM; final concentration in the 5 μl assay volume=2 mM) and substrate (0.8 μM; final concentration in the 5 μl assay volume=0.5 μM) in assay buffer, and the resulting mixture was incubated for a reaction time of 60 min at 22° C. The concentration of FGFR-4 fusion protein was adjusted depending on the activity of the enzyme lot and was chosen appropriately to have the assay in the linear range (typical concentrations were in the range of 0.03 μg/ml). The reaction was stopped by the addition of 5 μl of a solution of HTRF detection reagents [100 nM streptavidin-XL665 (Cis Biointernational) and 1 nM PT66-Tb-cryptate, a terbium-cryptate labelled anti-phosphotyrosine antibody (Cis Biointernational; PT66-Eu-chelate from Perkin-Elmer may be used instead), in an aqueous EDTA solution (50 mM EDTA, 0.1% (w/v) BSA in 50 mM HEPES/NaOH pH 7.5)].

The resulting mixture was incubated for 1 h at 22° C. to allow formation of the complex between the phosphorylated biotinylated peptide and the detection reagents. Subsequently, the amount of phosphorylated substrate was evaluated by measurement of the resonance energy transfer from the Tb-chelate to the streptavidin-XL665. For this, the fluorescence emissions at 620 nm and 665 nm after excitation at 350 nm were measured in a TR-FRET reader [e.g. Rubystar (BMG Labtechnologies, Offenburg, Germany) or Viewlux (Perkin-Elmer)]. The ratio of the emissions at 665 nm and at 620 nm was taken as the measure for the amount of phosphorylated substrate. Data were normalised (enzyme reaction without inhibitor=0% inhibition, all other assay components but no enzyme=100% inhibition), and IC$_{50}$ values were calculated by a 4-parameter fit using an in-house software.

B-4. mTOR Kinase Assay (for Comparative Purposes)

mTOR inhibitory activity of the compounds of the present invention was quantified employing the TR-FRET based mTOR assay as described in the following paragraphs:

Recombinant fusion tagged mTOR protein [glutathione-S-transferase (GST) fused to human mTOR amino acids from 1360 to 2549], expressed in insect cells and purified by glutathione-sepharose affinity chromatography, was purchased from Invitrogen (Cat.-No. 4753) and used as enzyme. As substrate for the kinase reaction, a recombinant fusion protein of GFP and 4E-BP1 (purchased from Invitrogen, Cat.-No. PV4759) was used.

Test compounds were dissolved in DMSO to generate 10 mM stock solutions. These solutions were first 10-fold diluted by 100% DMSO to get 1 mM solutions in 100% DMSO, then 100-fold diluted by 50% DMSO to get 10 μM solutions in 50% DMSO.

For the assay, 0.5 μl of a 10 μM solution of the test compound in 50% DMSO was pipetted into a black, low-volume 384-well microtiter plate (Greiner Bio-One, Frickenhausen, Germany). 2 μl of a solution of the above mTOR fusion protein in aqueous assay buffer [50 mM HEPES/NaOH pH 7.5, 5 mM magnesium chloride, 1.0 mM dithiothreitol, 1 mM EGTA, 0.01% (v/v) Triton-X100, 0.01% (w/v) bovine serum albumin (BSA)] was added, and the mixture was incubated for 15 min at 22° C. to allow pre-binding of the test compound to the enzyme. Then, the kinase reaction was started by the addition of 2.5 μl of a solution of adenosine triphosphate (ATP, 80 μM; final concentration in the 5 μl assay volume=40 μM) and substrate (0.6 μM; final concentration in the 5 μl assay volume=0.3 μM) in assay buffer, and the resulting mixture was incubated for a reaction time of 60 min at 22° C. The concentration of mTOR fusion protein was chosen appropriately to have the assay in the linear range (a typical final concentration in the 5 μl assay volume was 1.25 ng/μl). The reaction was stopped by the addition of 5 μl of 30 mM EDTA (final concentration in the 10 μl assay volume=15 mM) and 2 nM Tb-chelate labelled anti-4E-BP1 [pT46] phosphospecific antibody [Invitrogen Cat.-No. PV4755] (final concentration in the 10 μl assay volume=1 nM) in FRET buffer.

The resulting mixture was incubated for 1 h at 22° C. to allow formation of the complex between the phosphorylated substrate and the Tb-chelate labelled antibody. Subsequently, the amount of phosphorylated substrate was evaluated by measurement of the resonance energy transfer from the Tb-chelate to the GFP. For this, the fluorescence emissions at 495 nm and 520 nm after excitation at 340 nm was measured in an Envision 2104 multilabel reader (Perkin-Elmer). The ratio of the emissions at 520 nm and at 495 nm was taken as the measure for the amount of phosphorylated substrate. Data were normalised (enzyme reaction without inhibitor=0% inhibition, all other assay components but no enzyme=100% inhibition), and either mean values (if tested in replicates at a single concentration) or $IC_{50}$ values (by a 4-parameter fit using an in-house software) were calculated.

Mean inhibition values at 1 μM for individual compounds of the present invention are listed in Table 3 below:

TABLE 3

| Example No. | mTOR % inhibition @ 1 μM |
| --- | --- |
| 1 | 1.9 |
| 2 | 6.1 |
| 3 | 2.5 |
| 4 | 8.4 |
| 5 | 2.7 |
| 6 | 11.3 |
| 7 | 4.7 |
| 8 | 4.7 |
| 9 | no inhib. effect detect. |
| 10 | 10.3 |
| 11 | no inhib. effect detect. |
| 12 | 7.2 |
| 13 | 5.3 |
| 14 | 0.3 |
| 15 | 4.0 |
| 16 | 8.8 |
| 17 | no inhib. effect detect. |
| 18 | no inhib. effect detect. |
| 19 | 1.8 |
| 20 | no inhib. effect detect. |
| 21 | no inhib. effect detect. |
| 22 | 1.6 |
| 23 | 2.0 |
| 24 | 0.3 |
| 25 | no inhib. effect detect. |
| 26 | no inhib. effect detect. |
| 27 | 5.0 |
| 28 | 35.5 |
| 29 | 0.6 |
| 30 | 1.6 |
| 31 | 9.1 |
| 32 | no inhib. effect detect. |

(no inhib. effect detect. = no inhibitory effect detectable at 1 μM).

The data in Table 3 show that the compounds of the present invention only have a weak, if any, inhibitory effect on mTOR kinase which is not considered to contribute to the pharmacological activity observed with these compounds.

B-5. Inhibition of Growth Factor-Mediated Cell Proliferation

Human umbilical vein endothelial cells (HUVEC) were obtained from Cellsystems (FC-0003) and grown in Vasculife VEGF complete medium (Cellsystems, LL-1020) containing 2% fetal bovine serum (FBS) at 37° C. and 5% $CO_2$. The cells were used for proliferation assays up to passage 7.

The HUVEC cells were harvested using accutase (PAA, L11-007) and seeded in columns 2 to 12 of 96-well plates (Falcon MICROTEST tissue culture plate 96-well flat bottom, BD 353075, or μCLEAR-PLATE, black, 96-well, Greiner Bio-One, No. 655090) at a cell density of 2500 cells/well in 100 μl Vasculife VEGF complete medium with column 1 remaining empty as blank. Cells were allowed to incubate at 37° C. and 5% $CO_2$ for at least 6 h. Then, the cells were washed once with PBS and starved overnight in Vasculife basal medium (Cellsystems, LM-0002) containing heparin, ascorbate and L-glutamine (components of the Vasculife Life Factors Kit, Cellsystems, LL-1020) as well as 0.2% FBS.

After about 18 h, the starving medium was discarded, and the cells were exposed for 72 h to 9 consecutive log or half-log concentrations of test compound in the range of 10 pM to 30 μM and to 5, 10 or 20 ng/ml hFGF-2 (recombinant human FGF basic, R&D Systems, 233-FB) in 100 μl starving medium. 10 mM stock solutions of test compounds in DMSO were diluted to 200× final concentration in DMSO resulting in a final DMSO concentration of 0.5% in all wells. Controls consisted of cells grown in starving medium only and of cells grown in hFGF-2 containing starving medium with 0.5% DMSO. To determine cell proliferation, 5 μl Alamar Blue solution (Biosource, DAL1100) was added to each well (1:20 dilution), and the cells were allowed to incubate for further 4 h at 37° C. and 5% $CO_2$ before measuring fluorescence (ex. 535 nm, em. 595 nm) with a Spectrafluor Plus Tecan plate reader (XFLUOR4 version 4.20). In some experiments, an ATP Determination Kit (BIAFFIN GmbH, LBR-T100) was used according to the manufacturer's instructions. In each experiment, samples were assayed in triplicate, and the standard deviations were determined. GraphPad Prism 5 software was used to analyze the data and to obtain $IC_{50}$ values. All test compounds were assayed 2 to 10 times in independent experiments and similar results were obtained.

The data listed in Table 4 below represent the $IC_{50}$ values for representative compounds of the invention resulting from the corresponding averaged $pIC_{50}$ values:

TABLE 4

| Example No. | hFGF-2 mediated HUVEC proliferation, $IC_{50}$ [nM] |
| --- | --- |
| 2 | 5.4 |
| 6 | 16.1 |
| 8 | 6.3 |
| 9 | 0.8 |
| 10 | 39.0 |
| 11 | 1.0 |
| 16 | 3.0 |
| 17 | 15.0 |
| 19 | 0.2 |
| 21 | 30.3 |
| 23 | 19.1 |
| 25 | 0.3 |
| 27 | 1.5 |
| 28 | 20.0 |
| 31 | 0.6 |

Most compounds of the present invention displayed about ten- to hundred-fold reduced inhibitory activity in this proliferation assay when vascular endothelial growth factor (VEGF-A165 isoform) was used as mediating growth factor (instead of FGF-2), indicating a significant selectivity of these compounds for FGFR versus VEGFR kinases.

B-6. Human Xenograft and Syngeneic Tumor Models

Different tumor models have been conducted in order to profile compounds of the present invention in vivo. Human, rat or mouse tumor cells were cultivated in vitro and implanted into either immunodeficient or immunocompetent mice, or immunodeficient rats. Treatment started after tumor establishment, and tumor-bearing animals were treated with substances via different routes (per os, intravenously, intraperitoneally or subcutaneously). Substances were tested as mono-therapy or in combination therapy with other pharmacological substances. Treatment of the tumor-bearing animals was conducted until the tumors reached an average size of 120 mm². Tumors were measured in two dimensions using a caliper, and tumor volume was calculated according to the formula (length×width)/2. Substance efficacy was evaluated at the end of the experiment using the T/C ratio [T=final tumor weight in the treated group; C=final tumor weight in the control group]. Statistical significance of the efficacy between control and treated groups was determined using the ANOVA variance test. All animal studies were conducted according to the German regulatory guidelines.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

C. EXAMPLES RELATING TO PHARMACEUTICAL COMPOSITIONS

Pharmaceutical compositions according to the present invention can be illustrated as follows:

Sterile i.v. Solution:

A 5 mg/mL solution of the desired compound of the invention can be made using sterile, injectable water, and the pH is adjusted if necessary. The solution is diluted for administration to 1-2 mg/mL with sterile 5% dextrose and is administered as an i.v. infusion over about 60 minutes.

Lyophilized Powder for i.v. Administration:

A sterile preparation can be prepared with (i) 100-1000 mg of the desired compound of the invention as a lyophilized powder, (ii) 32-327 mg/mL sodium citrate, and (iii) 300-3000 mg Dextran 40. The formulation is reconstituted with sterile, injectable saline or 5% dextrose to a concentration of 10 to 20 mg/mL, which is further diluted with saline or 5% dextrose to 0.2 to 0.4 mg/mL, and is administered either as i.v. bolus or by i.v. infusion over 15-60 minutes.

Intramuscular Suspension:

The following solution or suspension can be prepared for intramuscular injection:

50 mg/mL of the desired, water-insoluble compound of the invention; 5 mg/mL sodium carboxymethylcellulose; 4 mg/mL Tween 80; 9 mg/mL sodium chloride; 9 mg/mL benzyl alcohol.

Hard Shell Capsules:

A large number of unit capsules are prepared by filling standard two-piece hard gelatin capsules each with 100 mg of the desired, powdered compound of the invention, 150 mg of lactose, 50 mg of cellulose and 6 mg of magnesium stearate.

Soft Gelatin Capsules:

A mixture of the desired compound of the invention in a digestible oil, such as soybean oil, cottonseed oil or olive oil, is prepared and injected by means of a positive displacement pump into molten gelatin to form soft gelatin capsules containing 100 mg of the active ingredient. The capsules are washed and dried. The desired compound of the invention can be dissolved in a mixture of polyethylene glycol, glycerin and sorbitol to prepare a water-miscible medicine mix.

Tablets:

A large number of tablets are prepared by conventional procedures so that the dosage unit is 100 mg of the desired compound of the invention, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability, or delay absorption.

Solution or Suspension for Topical Application to the Eye (Eye Drops):

A sterile formulation can be prepared with 100 mg of the desired compound of the invention as a lyophilized powder reconstituted in 5 mL of sterile saline. As preservative, benzalkonium chloride, thimerosal, phenylmercuric nitrate, or the like may be used in a range of about 0.001% to 1% by weight.

We claim:

1. A compound of formula (I)

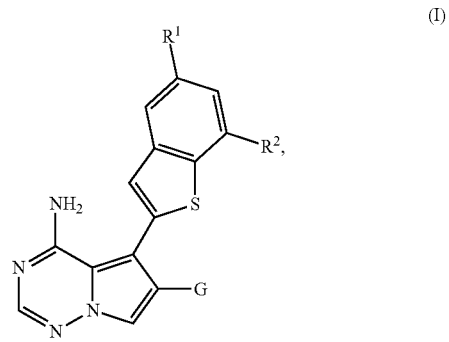

wherein
$R^1$ is hydrogen, chloro, methyl or methoxy,
$R^2$ is hydrogen or methoxy,
with the proviso that at least one of $R^1$ and $R^2$ is other than hydrogen,
and
G represents the group —$CH_2$—$OR^3$, —$C(=O)$—$OR^3$, —$CH_2$—$NR^4R^5$ or —$C(=O)$—$NR^4R^6$, wherein
$R^3$ is hydrogen or ($C_1$-$C_4$)-alkyl optionally substituted with cyano, hydroxy, ($C_1$-$C_4$)-alkoxy, hydroxycarbonyl, ($C_1$-$C_4$)-alkoxycarbonyl, amino, mono-($C_1$-$C_4$)-alkylamino, di-($C_1$-$C_4$)-alkylamino, pyrrolidino, piperidino, morpholino, aminocarbonyl, mono-($C_1$-$C_4$)-alkyl aminocarbonyl, di-($C_1$-$C_4$)-alkylaminocarbonyl or up to three fluoro atoms,
$R^4$ is hydrogen or ($C_1$-$C_4$)-alkyl,
$R^5$ is hydrogen, ($C_1$-$C_4$)-alkyl, ($C_1$-$C_4$)-alkylcarbonyl, ($C_3$-$C_6$)-cycloalkyl or 4- to 6-membered heterocycloalkyl, wherein (i) said $(C_1-C_4)$-alkyl is optionally substituted with cyano, hydroxy, $(C_1-C_4)$-alkoxy, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_1-C_4)$-alkylcarbonylamino or up to three fluoro atoms, and (ii) said $(C_3-C_6)$-cycloalkyl is optionally substituted with one or two substituents independently selected from the group consisting of $(C_1-C_4)$-alkyl, hydroxy, amino and $(C_1-C_4)$-alkylcarbonylamino, and (iii) said 4- to 6-membered heterocycloalkyl is optionally substituted with one or two substituents independently selected from the group consisting of $(C_1-C_4)$-alkyl, hydroxy, oxo, amino and $(C_1-C_4)$-alkylcarbonyl amino, $R^6$ is hydrogen, $(C_1-C_4)$-alkyl, $(C_3-C_6)$-cycloalkyl or 4- to 6-membered heterocycloalkyl, wherein (i) said $(C_1-C_4)$-alkyl is optionally substituted with hydroxy, $(C_1-C_4)$-alkoxy, $(C_1-C_4)$-alkoxycarbonyl, amino, aminocarbonyl, mono-$(C_1-C_4)$-alkylaminocarbonyl, di-$(C_1-C_4)$-alkylaminocarbonyl or $(C_1-C_4)$-alkylcarbonylamino, and (ii) said $(C_3-C_6)$-cycloalkyl is optionally substituted with one or two substituents independently selected from the group consisting of $(C_1-C_4)$-alkyl, hydroxy, amino and $(C_1-C_4)$-alkylcarbonylamino, and (iii) said 4- to 6-membered heterocycloalkyl is optionally substituted with one or two substituents independently selected from the group consisting of $(C_1-C_4)$-alkyl, hydroxy, oxo, amino and $(C_1-C_4)$-alkylcarbonylamino, or $R^4$ and $R^5$, or $R^4$ and $R^6$, respectively, are joined and, taken together with the nitrogen atom to which they are attached, form a monocyclic, saturated 4- to 7-membered heterocycloalkyl ring which may contain a second ring heteroatom selected from $N(R^7)$, O, S and $S(O)_2$, and which may be substituted on ring carbon atoms with up to three substituents independently selected from the group consisting of fluoro, $(C_1-C_4)$-alkyl, oxo, hydroxy, $(C_1-C_4)$-alkoxy, amino, mono-$(C_1-C_4)$-alkylamino, di-$(C_1-C_4)$-alkylamino and aminocarbonyl, and wherein $R^7$ is hydrogen, $(C_1-C_4)$-alkyl, cyclopropyl, cyclobutyl, formyl, $(C_1-C_4)$-alkylcarbonyl or $(C_1-C_4)$-alkoxycarbonyl, or a pharmaceutically acceptable salt, hydrate and/or solvate thereof.

2. The compound of formula (I) according to claim 1, wherein $R^1$ is hydrogen, chloro, methyl or methoxy, $R^2$ is hydrogen or methoxy, with the proviso that at least one of $R^1$ and $R^2$ is other than hydrogen, and G represents the group —$CH_2$—$OR^3$, —$C(=O)$—$OR^3$, —$CH_2$—$NR^4R^5$ or —$C(=O)$—$NR^4R^6$, wherein $R^3$ is hydrogen or $(C_1-C_4)$-alkyl optionally substituted with hydroxy, $(C_1-C_4)$-alkoxy, hydroxycarbonyl, $(C_1-C_4)$-alkoxycarbonyl, amino, aminocarbonyl, mono-$(C_1-C_4)$-alkylaminocarbonyl, di-$(C_1-C_4)$-alkyl aminocarbonyl or up to three fluoro atoms, $R^4$ is hydrogen or $(C_1-C_4)$-alkyl, $R^5$ is hydrogen, $(C_1-C_4)$-alkyl, $(C_1-C_4)$-alkylcarbonyl, $(C_3-C_6)$-cycloalkyl or 4- to 6-membered heterocycloalkyl, wherein (i) said $(C_1-C_4)$-alkyl is optionally substituted with hydroxy, $(C_1-C_4)$-alkoxy, $(C_1-C_4)$-alkoxycarbonyl, aminocarbonyl, mono-$(C_1-C_4)$-alkylaminocarbonyl, di-$(C_1-C_4)$-alkylaminocarbonyl or $(C_1-C_4)$-alkylcarbonyl amino, and (ii) said $(C_3-C_6)$-cycloalkyl is optionally substituted with one or two substituents independently selected from the group consisting of $(C_1-C_4)$-alkyl, hydroxy, amino and $(C_1-C_4)$-alkylcarbonylamino, and (iii) said 4- to 6-membered heterocycloalkyl is optionally substituted with one or two substituents independently selected from the group consisting of $(C_1-C_4)$-alkyl, hydroxy, oxo, amino and $(C_1-C_4)$-alkylcarbonyl amino, $R^6$ is hydrogen, $(C_1-C_4)$-alkyl, $(C_3-C_6)$-cycloalkyl or 4- to 6-membered heterocycloalkyl, wherein (i) said $(C_1-C_4)$-alkyl is optionally substituted with hydroxy, $(C_1-C_4)$-alkoxy, $(C_1-C_4)$-alkoxycarbonyl, amino, aminocarbonyl, mono-$(C_1-C_4)$-alkylaminocarbonyl, di-$(C_1-C_4)$-alkylaminocarbonyl or $(C_1-C_4)$-alkylcarbonylamino, and (ii) said $(C_3-C_6)$-cycloalkyl is optionally substituted with one or two substituents independently selected from the group consisting of $(C_1-C_4)$-alkyl, hydroxy, amino and $(C_1-C_4)$-alkylcarbonylamino, and (iii) said 4- to 6-membered heterocycloalkyl is optionally substituted with one or two substituents independently selected from the group consisting of $(C_1-C_4)$-alkyl, hydroxy, oxo, amino and $(C_1-C_4)$-alkylcarbonylamino, or $R^4$ and $R^5$, or $R^4$ and $R^6$, respectively, are joined and, taken together with the nitrogen atom to which they are attached, form a monocyclic, saturated 4- to 7-membered heterocycloalkyl ring which may contain a second ring heteroatom selected from $N(R^7)$ and O, and which may be substituted on ring carbon atoms with up to three substituents independently selected from the group consisting of $(C_1-C_4)$-alkyl, oxo, hydroxy, amino and aminocarbonyl, and wherein $R^7$ is hydrogen, $(C_1-C_4)$-alkyl, formyl, $(C_1-C_4)$-alkylcarbonyl or $(C_1-C_4)$-alkoxycarbonyl, or a pharmaceutically acceptable salt, hydrate and/or solvate thereof.

3. The compound of formula (I) according to claim 1, wherein $R^1$ is hydrogen, chloro, methyl or methoxy, $R^2$ is methoxy, and G represents the group —$CH_2$—$OR^3$, —$CH_2$—$NR^4R^5$ or —$C(=O)$—$NR^4R^6$, wherein $R^3$ is hydrogen or $(C_1-C_4)$-alkyl optionally substituted with hydroxy, $(C_1-C_4)$-alkoxycarbonyl, amino or aminocarbonyl, $R^4$ is hydrogen or methyl, $R^5$ is $(C_1-C_4)$-alkyl, $(C_1-C_4)$-alkylcarbonyl or 5- or 6-membered heterocycloalkyl, wherein (i) said $(C_1-C_4)$-alkyl is optionally substituted with hydroxy, $(C_1-C_4)$-alkoxycarbonyl, aminocarbonyl, mono-$(C_1-C_4)$-alkylaminocarbonyl or $(C_1-C_4)$-alkylcarbonylamino, and
(ii) said 5- or 6-membered heterocycloalkyl is optionally substituted with oxo $R^6$ is hydrogen or $(C_1-C_4)$-alkyl optionally substituted with hydroxy, amino or aminocarbonyl,
or $R^4$ and $R^5$, or $R^4$ and $R^6$, respectively, are joined and, taken together with the nitrogen atom to which they are attached, form a monocyclic, saturated 4- to 6-membered heterocycloalkyl ring which may contain a second ring heteroatom selected from $N(R^7)$ and O, and which may be substituted on ring carbon atoms with one or two substituents independently selected from the group consisting of methyl, oxo, hydroxy, amino and aminocarbonyl, and wherein $R^7$ is hydrogen, $(C_1-C_4)$-alkyl, $(C_1-C_4)$-alkylcarbonyl or $(C_1-C_4)$-alkoxycarbonyl, or a pharmaceutically acceptable salt, hydrate and/or solvate thereof.

4. The compound of formula (I) according to claim 1, wherein $R^1$ is methyl,
$R^2$ is methoxy,
and
G represents the group $—CH_2—OR^3$ or $—CH_2—NR^4R^5$, wherein $R^3$ is $(C_1-C_4)$-alkyl optionally substituted with hydroxy, amino or aminocarbonyl,
$R^4$ is hydrogen or methyl,
$R^5$ is $(C_1-C_4)$-alkyl substituted with hydroxy or aminocarbonyl, or is acetyl or 2-oxopyrrolidin-3-yl,
or $R^4$ and $R^5$ are joined and, taken together with the nitrogen atom to which they are attached, form a monocyclic, saturated 5- or 6-membered heterocycloalkyl ring which may contain a second ring heteroatom selected from $N(R^7)$ and O, and which may be substituted on a ring carbon atom with oxo, hydroxy or aminocarbonyl, and wherein $R^7$ is hydrogen or acetyl,
or a pharmaceutically acceptable salt, hydrate and/or solvate thereof.

5. A process for preparing a compound of formula (I) as defined in claim 1, comprising coupling a 6-(hydroxymethyl)-substituted 4-amino-5-bromopyrrolo[2, 1-f][1,2,4]triazine of formula (II)

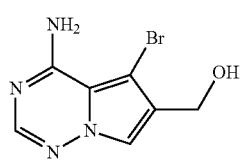

with a benzothiophen-2-yl boronate of formula (III)

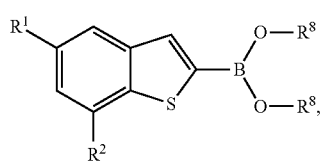

wherein $R^1$ and $R^2$ have the meanings indicated in claim 1,
and $R^8$ represents hydrogen or $(C_1-C_4)$-alkyl, or both $R^8$ residues are linked together to form a $—(CH_2)_2—$, $—C(CH_3)_2—C(CH_3)_2—$, $—(CH_2)_3—$, $—CH_2—C(CH_3)_2—CH_2—$ or $—C(=O)—CH_2—N(CH_3)—CH_2—C(=O)—$ bridge, in the presence of a palladium catalyst and a base to yield a compound of formula (I-A)

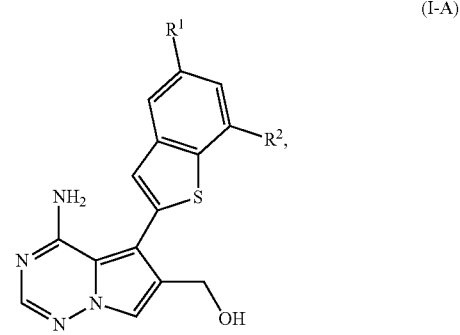

wherein $R^1$ and $R^2$ have the meanings indicated in claim 1,
and optionally either [A] converting the compound of formula (I-A) into a corresponding 6-(halomethyl) derivative of formula (IV)

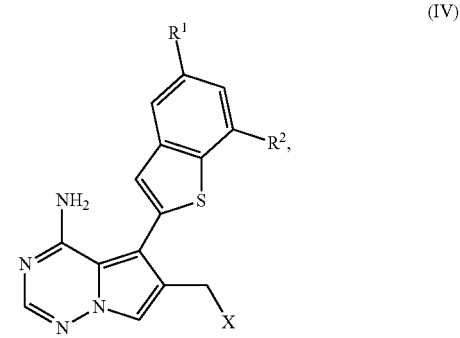

wherein $R^1$ and $R^2$ have the meanings indicated in claim 1,
and
X is chloro, bromo or iodo,
and then reacting the 6-(halomethyl) derivative of formula (IV) in the presence of a base with an alcohol of formula (V) or with an amine of formula (VII-A)

wherein $R^4$ has the meaning indicated in claim 1, and $R^{3A}$ and $R^{5A}$ have the meanings of $R^3$ and $R^5$, respectively, as indicated in claim 1, except for hydrogen, to give a compound of formula (I-B) or formula (I-C1), respectively,

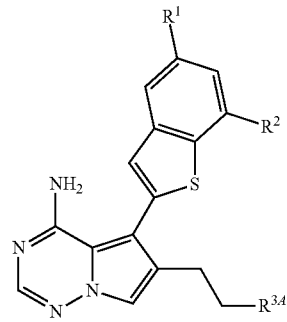
(I-B)

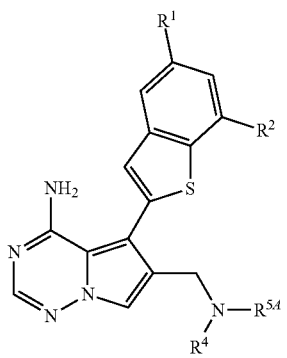
(I-C1)

wherein $R^1$, $R^2$, $R^{3A}$, $R^4$ and $R^{5A}$ have the meanings described above, or

[B] oxidizing the compound of formula (I-A) to an aldehyde of formula (VI)

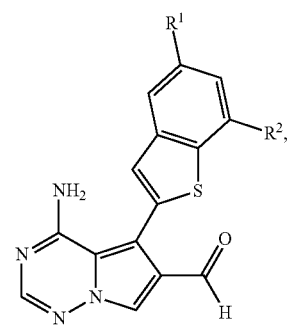
(VI)

wherein $R^1$ and $R^2$ have the meanings indicated in claim 1, and then reacting the aldehyde of formula (VI) with an amine of formula (VII)

(VII)

wherein $R^4$ and $R^5$ have the meanings indicated in claim 1, in the presence of an acid and a reducing agent to give a compound of formula (I-C)

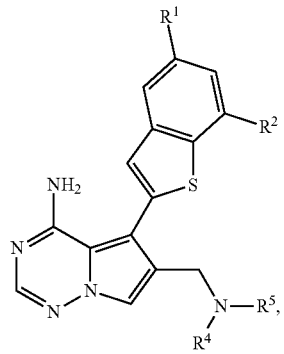
(I-C)

wherein $R^1$, $R^2$, $R^4$ and $R^5$ have the meanings indicated in claim 1, or

[C] oxidizing the compound of formula (I-A) to a carboxylic acid of formula (I-D)

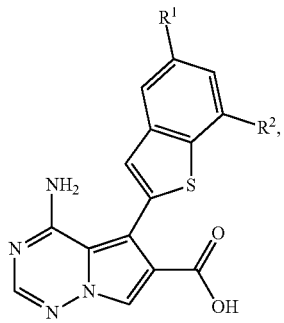
(I-D)

wherein $R^1$ and $R^2$ have the meanings indicated in claim 1, and then coupling the carboxylic acid of formula (I-D) with an alcohol of formula (V) or with an amine of formula (VIII)

(V)

$R^{3A}-OH$

(VIII)

wherein $R^{3A}$ has the meaning described above, and $R^4$ and $R^6$ have the meanings indicated in claim 1, in the presence of a condensing agent to give a compound of formula (I-E) or formula (I-F), respectively,

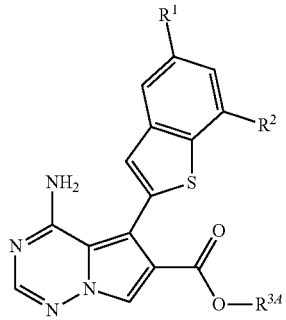
(I-E)

-continued

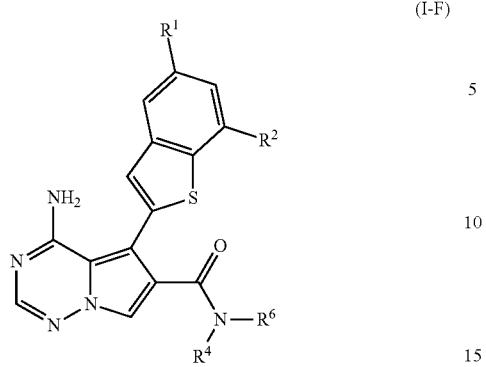
(I-F)

wherein $R^1$, $R^2$, $R^{3,4}$, $R^4$ and $R^6$ have the meanings described above, and optionally separating the compound of formula (I)-A, formula (I)-B, formula (I)-C, formula (I)-D, or formula (I)-E into its enantiomers or diastereomers, and optionally converting the compound of formula (I)-A, formula (I)-B, formula (I)-C, formula (I)-D, or formula (I)-E into a hydrate, solvate, salt or hydrate or solvate of a salt thereof.

6. Pharmaceutical composition comprising a compound as defined in claim 1 and one or more pharmaceutically acceptable excipients.

7. The pharmaceutical composition of claim 6 further comprising one or more additional therapeutic agents.

* * * * *